(12) United States Patent
Minshull

(10) Patent No.: US 12,351,813 B2
(45) Date of Patent: Jul. 8, 2025

(54) TETRACYCLINE-INDUCIBLE EXPRESSION SYSTEM

(71) Applicant: DNA TWOPOINTO INC., Newark, CA (US)

(72) Inventor: Jeremy Minshull, Los Altos, CA (US)

(73) Assignee: DNA TWOPOINTO INC., Newark, CA (US)

( * ) Notice: Subject to any disclaimer, the term of this patent is extended or adjusted under 35 U.S.C. 154(b) by 182 days.

(21) Appl. No.: 18/067,686

(22) Filed: Dec. 16, 2022

(65) Prior Publication Data

US 2023/0323396 A1 Oct. 12, 2023

Related U.S. Application Data

(63) Continuation of application No. 17/700,405, filed on Mar. 21, 2022, now Pat. No. 11,566,262.

(60) Provisional application No. 63/165,484, filed on Mar. 24, 2021.

(51) Int. Cl.
| | |
|---|---|
| *C12N 15/86* | (2006.01) |
| *A01K 67/0275* | (2024.01) |
| *A61K 48/00* | (2006.01) |
| *C12N 5/071* | (2010.01) |
| *C12N 15/85* | (2006.01) |

(52) U.S. Cl.
CPC .......... *C12N 15/86* (2013.01); *A01K 67/0275* (2013.01); *A61K 48/0066* (2013.01); *C12N 5/0682* (2013.01); *C12N 15/8509* (2013.01); *A01K 2217/05* (2013.01); *A01K 2217/203* (2013.01); *A01K 2227/105* (2013.01); *C12N 2710/16142* (2013.01); *C12N 2800/90* (2013.01); *C12N 2830/003* (2013.01); *C12N 2830/50* (2013.01)

(58) Field of Classification Search
None
See application file for complete search history.

(56) References Cited

U.S. PATENT DOCUMENTS

| | | |
|---|---|---|
| 4,736,866 A | 4/1988 | Leder et al. |
| 4,870,009 A | 9/1989 | Evans et al. |
| 5,464,758 A | 11/1995 | Gossen et al. |
| 5,654,168 A | 8/1997 | Bujard et al. |
| 5,789,156 A | 8/1998 | Bujard et al. |
| 5,814,618 A | 9/1998 | Bujard et al. |
| 5,854,310 A | 12/1998 | Maxson |
| 5,866,755 A | 2/1999 | Bujard et al. |
| 5,888,981 A | 3/1999 | Bujard et al. |
| 5,891,665 A | 4/1999 | Wilson |
| 5,912,411 A | 6/1999 | Bujard et al. |
| 6,004,941 A | 12/1999 | Bujard et al. |
| 6,087,166 A | 7/2000 | Baron et al. |
| 6,136,954 A | 10/2000 | Bujard et al. |
| 6,242,667 B1 | 6/2001 | Bujard et al. |
| 6,252,136 B1 | 6/2001 | Bujard et al. |
| 6,271,341 B1 | 8/2001 | Baron et al. |
| 6,271,348 B1 | 8/2001 | Bujard et al. |
| 6,914,124 B2 | 7/2005 | Bujard et al. |
| 7,541,446 B2 | 6/2009 | Hillen et al. |
| 7,745,592 B2 | 6/2010 | Massie et al. |
| 7,935,788 B2 | 5/2011 | Malenfant et al. |
| 8,728,759 B2 | 5/2014 | Xu et al. |
| 9,181,556 B2 | 11/2015 | Bujard et al. |
| 10,563,222 B2 * | 2/2020 | Yang ...................... C12N 15/85 |
| 11,566,262 B2 | 1/2023 | Minshull et al. |
| 11,851,672 B2 * | 12/2023 | Pul ......................... A61K 48/00 |
| 2009/0181424 A1 * | 7/2009 | Albericio ............... C12N 15/85 435/325 |
| 2015/0218584 A1 * | 8/2015 | Payne .................... C12N 15/85 435/325 |
| 2017/0101629 A1 | 4/2017 | Minshull et al. |
| 2017/0101646 A1 * | 4/2017 | Minshull ................ C12N 15/81 |
| 2017/0130244 A1 * | 5/2017 | Yang ...................... C12N 15/85 |
| 2019/0055580 A1 | 2/2019 | McGrew et al. |
| 2020/0149053 A1 * | 5/2020 | Fisher .................... A61K 38/20 |
| 2020/0318135 A1 | 10/2020 | Minshull et al. |

FOREIGN PATENT DOCUMENTS

| | | |
|---|---|---|
| EP | 2352833 B1 | 3/2013 |
| WO | WO 2012/099540 A1 | 7/2012 |
| WO | WO 2019/028273 | 2/2019 |

OTHER PUBLICATIONS

Dorsch-Hasler PNAS 24, 8325-8329 (Year: 1985).*
Backman et al., "Tetracycline-inducible expression systems for the generation of transgenic animals; a comparison of various inducible systems carried in a single vector." Journal of Neuroscience Methods, vol. 139, pp. 257-262, (2004).
Baron et al., "Tetracycline-controlled transcription in eukaryotes: novel transactivators with graded transactivation potential," Nucleic Acids Research, 25(14), 2723-2729, (1997).
Cowell, "Repression versus activation in the control of gene transcription," Trends in Biochemical Sciences, 19:1, 38-42, (1994).
Deuschle et al., "Tetracycline-reversible silencing of eukaryotic promoters," Mol. Cell. Biol., 15:4, 1907-1914, (1995).
Fukushige et al., "Genomic targeting with a positive-selection lox, integration vector allows highly reproducible gene expression in mammalian cells." Proc. Natl. Acad. Sci., vol. 89, pp. 7905-7909, (1992).
Gossen et al., "Tight control of gene expression in mammalian cells by tetracycline- responsive promoters." Proc. Natl. Acad. Sci., vol. 89. pp. 5547-5551, (1992).

(Continued)

*Primary Examiner* — Brian Whiteman
(74) *Attorney, Agent, or Firm* — Alston & Bird LLP

(57) ABSTRACT

The invention provides inducible promoter systems and their components incorporating components of a tetracycline operon. By coordinating expression of different transcriptional units in these systems as a result of selection of promoters and/or linking the units into the same DNA molecule, these systems can achieve higher levels of expression of coding segments of interest, increased differential levels of expression between on- and off-states, and/or greater responsiveness to inducing agents than conventional systems.

29 Claims, 7 Drawing Sheets

Specification includes a Sequence Listing.

(56) References Cited

OTHER PUBLICATIONS

Gossen et al., "Transcriptional activation by tetracyclines in mammalian cells," Science, 268:5218, 1766-1769, (1995).
Gossen, M., et al., Control of gene activity in higher eukaryotic cells by prokaryotic regulatory elements, TIBS, vol. 18, No. 12, pp. 471-475 (1993).
Hillen et al., "Nucleotide sequence of the Tn 10 encoded tetracycline resistance gene." vol. 11, No. 2, Nucleic Acids Res., pp. 525-539 (1983).
Hoffmann et al., "A novel tetracycline-dependent expression vector with low basal expression and potent regulatory properties in various mammalian cell lines." Nucleic Acids Res., vol. 25, No. 5, pp. 1078 1079, (1997).
Lee et al., "Glucocorticoids regulate expression of dihydrofolate reductase cDNA in mouse mammary tumour virus chimaeric plasmids," Nature (London), 294:228-232, (1981).
Loew et al. Improved Tet-responsive promoters with minimized background expression. BMC Biotechnology 10: 1-13, (2010).
Moritz, et al., "CMV promoter mutants with a reduced propensity to productivity loss in CHO cells," Sci Rep, vol. 5, No. 16952, pp. 1-8, (Nov. 19, 2015).
Mullick et al., "The cumate gene-switch: a system for regulated expression in mammalian cells," BMC Biotechnology doi: 10.1186/1472-6750-6-43, (2006).
No et al., "Ecdysone-Inducible Gene Expression in Mammalian Cells and Transgenic Mice," Proc. Natl. Acad. Sci. USA, vol. 93, No. 8, pp. 3346-3351, (Apr. 1996).
Rivera et al., "A humanized system for pharmacologic control of gene expression," Nat Med, 2:1028-1032, (1996).
Saenger et al., "The Tetracycline Repressor—A Paradigm for a Biological Switch," Angew. Chem. Int. Ed., 39, 2042-2052, (2000).
Stieger et al., "In vivo gene regulation using tetracycline-regulatable systems." Advanced Drug Delivery Reviews 61, pp. 527-541, (2009).
Tovar et al., "Identification and nucleotide sequence at the class E tet regulatory elements and operator and inducer binding of the encoded purified Tet repressor." Mol. Gen. Genet., vol. 215, pp. 76-80, (1988).
Urlinger et al., "Exploring the sequence space for tetracycline-dependent transcriptional activators: Novel mutations yield expanded range and sensitivity," PNAS, vol. 97, No. 14, pp. 7963-7968, (2000).
Vigna et al., "Robust and Efficient Regulation of Transgene Expression in Vivo by Improved Tetracycline-Dependent Lentiviral Vectors." Molecular Therapy, vol. 5, No. 3, pp. 252-261, (2002).
Weidenfeld et al., "Inducible expression of coding and inhibitory RNAs from retargetable genomic loci." Nucleic Acids Res., pp. 1-11, (2009).
Yao et al., "Tetracycline Repressor, tetR, rather than the tetR Mammalian Cell Transcription Factor Fusion Derivatives, Regulates Inducible Gene Expression in Mammalian Cells," Human Gene Therapy, No. 9. pp. 1939-1950, (1998).
U.S. Appl. No. 17/700,405, Non-Final Office Action mailed Jul. 27, 2022.
U.S. Appl. No. 17/700,405, Notice of Allowance mailed Oct. 4, 2022.
WIPO Application No. PCT/US/2022/021219, PCT International Search Report and Written Opinion of the International Searching Authority mailed Aug. 18, 2022.
EP Application No. 22776416.4, extended European search report mailed Feb. 19, 2025.

* cited by examiner

```
Human CMV    ------------------------------------------------------------TGCT
Hybrid       AGTCATTGGGTTTTTCCAGCCAATTTATAAAACGCCATGTACTTTCCCACCATTGACGTC
Murine CMV   AGTCATTGGGTTTTTCCAGCCAATTTATAAAACGCCATGTACTTTCCCACCATTGACGTC
                                                                        *

CpG-179
Human CMV    GATGCGGTTTTGGCAGTACACCAATGGG---CGTGGATAGCGGTTT---------GACTC
Hybrid       AATGGGCTATTGAAACTAATGCAACGTGACCTTTAAACGGTACTTTCCCATAGCTGATTA
Murine CMV   AATGGGCTATTGAAACTAATGCAACGTGACCTTTAAACGGTACTTTCCCATAGCTGATTA
              ***  *  * ***   *  **   *** *  *        *  *   ***       ** *

Human CMV    ACGGGGATTTCCAAGTCTCCACCCCATTGACGTCAATGGGAGTTTGTTTTGGCACCAAAA
Hybrid       ATGGGAAAGTACCGTTCTCGAGCCAATACACGTCAATGGGAGTTTGTTTTGGCACCAAAA
Murine CMV   ATGGGAAAGTACCGTTCTCGAGCCAATACACGTCAATGGGAAGTGAAAGGGCAGCCAAAA
              * ***  *  *  **** *  * ** **  **************   *      ******

Human CMV    TCAACGGGACTTTCCAAAATGTCGTAATAACCCCGCCCCGTTGACGCAAATGGGCGGTAG
Hybrid       TCAACGGGACTTTCCAAAATGTCGTAATAACCCCGCCCCGTTGACGCAAATGGGCGGTAG
Murine CMV   CGTAACACCGCCCCGGTTTTCCCCTGGAAATTCCATATTGGC-ACGCATTCTATTGGCTG
                *       *       *  *  **  **     *    *****   ** *

TATA                              +1
Human CMV    GCGTGTACGGTGGGAGGTCTATATAAGCAGAGCTCGTTTAGTGAACCG
Hybrid       GCGTGTACGGTGGGAGGTCTATATAAGCAGAGCTCGTTTAGTGAACCG
Murine CMV   AGCTGCGTTCTACGTGGGTATAAGAGGCGCGACCAGCGTCG-GTACCG
              **    *  *  **    ****   *    *  *  *    ****
```

Fig. 1

TETRACYCLINE-INDUCIBLE EXPRESSION SYSTEM

CROSS-REFERENCE TO RELATED APPLICATION

The present application is a continuation of U.S. application Ser. No. 17/700,405 filed Mar. 21, 2022, now U.S. Pat. No. 11,566,262, which claims priority to and the benefit of 63/165,484 filed Mar. 24, 2021 each of which is incorporated by reference in its entirety for all purposes.

REFERENCE TO A SEQUENCE LISTING

The application includes sequences in an electronic sequence listing named 587230replacementSEQLST.XML of size 269.2 KB, created Dec. 5, 2024, which is incorporated by reference.

BACKGROUND

The tet operon confers tetracycline resistance in bacteria. The operon includes tet-operator sites, a promoter, and a bicistronic transcriptional unit encoding a tet-repressor and a tetracycline-resistance protein. In the absence of tetracycline, the tet-repressor binds to the tet-operator sites inhibiting expression from the promoter of both the tet-repressor and tetracycline-resistance protein. When tetracycline is present it binds to the tet-repressor inhibiting its own binding to the tet-operators. Tetracycline-resistance protein is then expressed as is more tet-repressor, which again shuts downs expression of the tet operon when the tetracycline has been exhausted.

The components of the tet operon have been incorporated into various inducible expression systems for regulating expression of a coding segment of interest (see, e.g., U.S. Pat. Nos. 5,814,618, 5,654,168, 5,650,298 and 5,464,758 and 9,181,556). Generally, such systems have two components. A first construct includes one or more tet-operators, a promoter and a coding segment of interest. A second construct includes a promoter and a tet-repressor (or modified form thereof), sometimes fused to a transcriptional activation domain. The presence of tetracycline controls binding of the tet-repressor to the tet-operators, and consequently expression of the coding segment.

SUMMARY OF THE CLAIMED INVENTION

A hybrid mouse-human CMV promoter effective for transcriptional initiation comprising a segment of a mouse CMV promoter of SEQ ID NO:16 upstream from a segment of a human CMV promoter of SEQ ID NO:13 or 14, wherein the hybrid promoter lacks a CG motif at positions corresponding to positions 42 and 43 of SEQ ID NO:13 (human CMV). Optionally, the hybrid promoter comprises a contiguous segment of the mouse CMV promoter of SEQ ID NO:16 and a contiguous segment of the human CMV promoter of SEQ ID NO:13, wherein the junction between contiguous segments is within the sequence ACGTCAATGGGA (SEQ ID NO:173), which is common to the mouse and human CMV promoter sequences. Optionally, the hybrid promoter of claim 2 having a sequence comprising SEQ ID NO:10. Optionally, the hybrid mouse-human-CMV promoter of claim 3 in operable linkage with first and second tet-operators. Optionally the hybrid mouse-human CMV promoter in in operable linkage with at least one cumate operator. Optionally, each cumate operator has a sequence selected independently from any of SEQ ID NOS: 156-158. Optionally, the hybrid mouse-human CMV promoter is in operable linkage with a coding segment to be expressed, optionally wherein the coding segment comprises an open reading frame encoding a polypeptide. Optionally, at least first and second tet-operators are situated between the promoter and coding segment. Optionally, the coding segment encodes a protein. Optionally, the protein is a membrane protein. Optionally, the protein is a therapeutic protein.

The invention further provides a nucleic acid comprising (a) the hybrid mouse-human CMV promoter as described above and (b) a promoter operably linked to a segment encoding a tet-repressor or cumate repressor. Optionally, the promoter of the second transcriptional unit is a weaker promoter than a human CMV promoter, for example, the promoter of the second construct is selected from SEQ ID NOS: 17-21, 33 or 34.

The invention further provides a transposon comprising a nucleic acid as described above flanked by inverted repeats of the transposon. Optionally, the transposon further comprises target sites flanking the inverted repeats. Optionally, the transposon is a piggyBac™ or piggyBac-like transposon.

The invention further provides a mouse-human-CMV promoter having a sequence comprising SEQ ID NO:12. Optionally, the hybrid mouse-human CMV promoter is in operable linkage with a coding segment to be expressed, optionally wherein the coding segment comprises an open reading frame encoding a polypeptide. Optionally, the coding segment encodes a protein, for example, a therapeutic protein.

The invention further provides a cell transformed with any of the nucleic acids or transposons described above. Optionally, the cell is mammalian.

The invention further provides a non-human animal transformed with any of the nucleic acids or transposons described above. Optionally, the non-human animal is transgenic.

The invention further provides a cell or nonhuman transgenic animal having a genome comprising (a) a hybrid mouse-human CMV promoter operably linked to at least two tet-operators and a coding segment, and (b) a promoter operably linked to a tet-repressor, wherein expression of the coding segment can be regulated by supplying tetracycline or doxycycline to the cell or nonhuman transgenic animal.

The invention further provides a cell or nonhuman transgenic animal having a genome comprising (a) a hybrid mouse-human CMV promoter operably linked to at least one cumate operators and a coding segment, and (b) a promoter operably linked to a cumate repressor, wherein expression of the coding segment can be regulated by supplying cumate or an analog to the cell or nonhuman transgenic animal.

The invention further provides a method for inducible expression of a coding segment comprising, providing a first transcriptional unit comprising in operable linkage a hybrid mouse-human CMV promoter comprising a segment of a mouse CMV promoter of SEQ ID NO: 16 upstream from a segment of a human CMV promoter of SEQ ID NO: 13, wherein the hybrid promoter lacks a CG motif at positions corresponding to positions 42 and 43 of SEQ ID NO:13 (human CMV), at least two tet-operators and a coding segment to be expressed, and a second transcriptional unit comprising in operable linkage a promoter and a segment encoding a tet-repressor, wherein the tet-repressor is expressed and in the absence of tetracycline or doxycycline, the tet-repressor binds to the tet-operators inhibiting expression of the coding segment, and in the presence of tetracycline or doxycycline, the tet-repressor binds to the tetracycline or doxycycline, which inhibits its binding to the tet-operators and thereby increasing expression of the open-reading frame.

The invention further provides a method for inducible expression of a coding segment comprising, providing a first transcriptional unit comprising in operable linkage a hybrid mouse-human CMV promoter comprising a segment of a mouse CMV promoter of SEQ ID NO: 16 upstream from a segment of a human CMV promoter of SEQ ID NO: 13, wherein the hybrid promoter lacks a CG motif at positions corresponding to positions 42 and 43 of SEQ ID NO:13 (human CMV), at least one cumate-operator(s) and a coding segment to be expressed, and a second transcriptional unit comprising in operable linkage a promoter and a segment encoding a cumate-repressor, wherein the cumate-repressor is expressed and in the absence of cumate, the cumate-repressor binds to the cumate-operator(s) inhibiting expression of the coding segment, and in the presence of cumate, the cumate-repressor binds to the cumate, which inhibits its binding to the cumate-operator(s) and thereby increasing expression of the open-reading frame.

Optionally, the first and second transcriptional units are components of the same contiguous DNA molecule. Optionally, the first and second transcriptional units are components of a transposon. Optionally, the transposon is a piggyBac™ or piggyBac-like transposon. Optionally, the method further comprises introducing the contiguous DNA molecule into a cell.

Optionally, the cell is mammalian. Optionally, the first and second transcriptional units integrate into the genome of the cell. Optionally, the method further comprises culturing the cell. Optionally, the method further comprises supplying tetracycline or doxycycline, or analog thereof, or cumate or an analog thereof to culture media of the cell.

The invention further provides a nucleic acid comprising a transcriptional unit comprising a promoter having a sequence comprising SEQ ID NO:24 in operable linkage with a heterologous coding segment.

Optionally, the promoter lacks a 5' flanking sequence from a natural chimpanzee CMV promoter with which it is naturally associated. Optionally, the nucleic acid further comprises at least first and second tet-operators in operable linkage with the promoter. Optionally, the first and second tet-operators are 5' to the promoter. Optionally, the nucleic acid comprises three, six or eight tet-operators 5' to the promoter. Optionally, the nucleic acid further comprises at least one cumate operator in operable linkage with the promoter. Optionally, the at least one cumate operators is 5' to the promoter. Optionally, the nucleic acid comprises three, six or eight cumate-operator 5' to the promoter.

Optionally, the nucleic acid comprises any of SEQ ID NOS: 164-166 providing the promoter and cumate operators. Optionally, the nucleic acid comprises any of SEQ ID NOS: 167-169 providing the promoter, the operators and a 5' UTR. Optionally, the three, six or eight tet-operators are separated by spacers of 10-25 nucleotides. Optionally, at least some of the spacers differ from one another. Optionally, the nucleic acid further comprises a segment encoding a 5' UTR, for example a 5' UTR having a sequence comprising SEQ ID NO:29. Optionally, the nucleic acid further comprises a second transcriptional unit comprising a second promoter operably linked to a segment encoding a tet-repressor effective to bind a tet-operator in the absence of tetracycline or doxycycline or modified-tet-repressor effective to bind a tet-operator in the presence of tetracycline or doxycycline, wherein the tet-repressor or modified tet-repressor is fused to a transcriptional activator. Optionally, the nucleic acid further comprises a second transcriptional unit comprising a second promoter operably linked to a segment encoding a cumate-repressor effective to bind a cumate-operator in the absence of cumate or modified-cumate-repressor effective to bind a cumate-operator in the presence of cumate, wherein the cumate-repressor or modified cumate-repressor is fused to a transcriptional activator. Optionally, the second transcriptional unit further comprises a polyadenylation sequence. Optionally, the tet-repressor has an amino acid sequence comprising SEQ ID NO:5. Optionally, the modified tet-repressor has an amino acid sequence comprising SEQ ID NO: 6. Optionally, the cumate repressor has an amino acid sequence comprising SEQ ID NO:170. Optionally, the modified cumate-repressor linked to the transcriptional activator has an amino acid sequence comprising SEQ ID NO:172. Optionally, the coding segment encodes a protein, for example a membrane protein, or a therapeutic protein.

The invention further provides a transposon comprising a nucleic acid as described above flanked by inverted repeats of the transposon. Optionally, the transposon further comprises target sites flanking the inverted repeats. Optionally, the transposon is a piggyBac™ or piggyBac-like transposon.

The invention further provides a cell transformed with the nucleic acid or transposon as described above. Optionally, the cell is mammalian.

The invention further provides a non-human animal transformed with a nucleic acid or transposon as described above. Optionally, the non-human animal is transgenic.

The invention further provides a cell or nonhuman transgenic animal having a genome comprising (a) a promoter having a sequence comprising SEQ ID NO:24 operably linked to at least two tet operons and a coding segment, and (b) a promoter operably linked to a tet-repressor or modified tet-repressor fused to transcriptional activation domain, wherein expression of the coding segment can be regulated by supplying tetracycline or doxycycline to the cell or nonhuman transgenic animal. The invention further provides a cell or nonhuman transgenic animal having a genome comprising (a) a promoter having a sequence comprising SEQ ID NO:24 operably linked to at least two cumate operators and a coding segment, and (b) a promoter operably linked to a cumate-repressor or modified cumate-repressor fused to transcriptional activation domain, wherein expression of the coding segment can be regulated by supplying cumate to the cell or nonhuman transgenic animal.

The invention further provides a method for inducible expression of a coding segment comprising; providing a first transcriptional unit comprising in operable linkage with a least two tet-operators, a promoter having a nucleotide sequence comprising SEQ ID NO: 24 and a coding segment, and a second transcriptional unit comprising in operable linkage a promoter, and a segment encoding a tet-repressor or modified tet-repressor fused to a transcriptional activator, wherein the tet-repressor fused to the transcriptional activator is expressed and in the absence of tetracycline or doxycycline the tet-repressor binds to the at least two tet-operators and expression of the coding segment is increased, or the modified tet-repressor fused to the transcriptional activator is expressed and in the presence of tetracycline or doxycycline the modified tet-repressor binds to the at least two tet-operators and expression of the coding segment is increased. The invention further provides a method for inducible expression of a coding segment comprising; providing a first transcriptional unit comprising in operable linkage with a least two cumate-operators, a promoter having a nucleotide sequence comprising SEQ ID NO: 24 and a coding segment, and a second transcriptional unit comprising in operable linkage a promoter, and a segment encoding a cumate-repressor or modified cumate-repressor fused to a transcriptional activator, wherein the cumate-repressor fused to the transcriptional activator is expressed and in the absence of cumate the cumate-repressor binds to the at least two tet-operators and expression of the coding segment is increased, or the modified cumate-repressor fused to the transcriptional activator is expressed and in the presence of tetracycline or doxycycline the modified cumate-repressor binds to the at least two cumate-operators and expression of the coding segment is increased. Optionally, the first and second transcriptional units are components of the same contiguous DNA molecule. Optionally, the first and second transcriptional units are components of a transposon. Optionally, the transposon is a piggyBac™ or piggyBac-like transposon. Optionally, the method further comprises comprising introducing the contiguous DNA molecule into a cell. Optionally, the cell is a mammalian cell. Optionally, the first and second transcriptional units integrate into the genome of the cell. Optionally, the method further comprises culturing the cell.

Optionally, the method further comprises supplying tetracycline or doxycycline or analog thereof, or cumate or an analog thereof to culture media of the cell.

BRIEF DESCRIPTION OF THE FIGURES

FIG. 1 shows alignments of mouse (SEQ ID NO:16), human (SEQ ID NO:13) and hybrid (SEQ ID NO:12) CMV promoters. The transcriptional start site is indicated as the underlined G labelled +1. The methylation-sensitive CG dinucleotide in the human sequence is underlined and labelled CpG-179. The TATA boxes of each promoter is underlined.

DEFINITIONS

Figure 2:
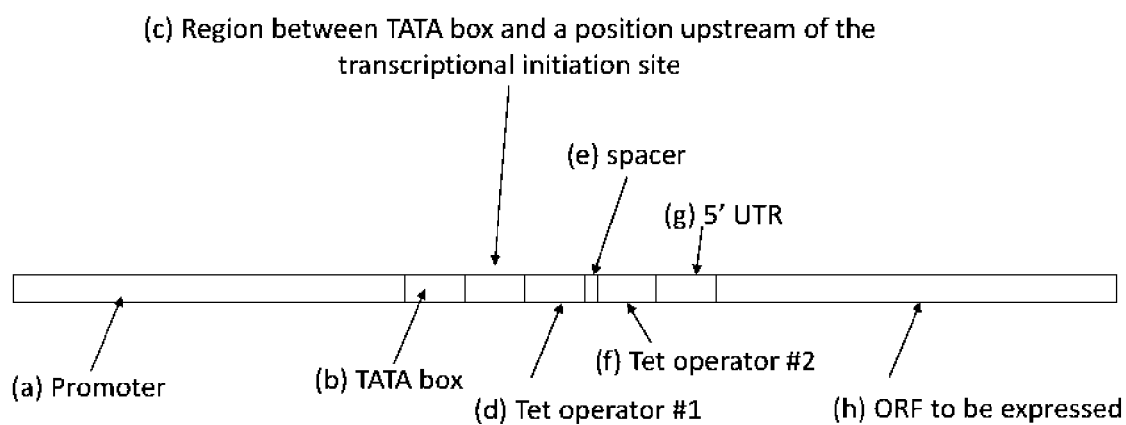
FIGS. 2 and 3 show first and second transcriptional units respectively for a system for tet-inducible expression of an open reading frame ("tet-off").

The singular forms "a," "an," and "the" include plural references unless the context clearly dictates otherwise. Thus, for example, reference to "a nucleic acid" includes a plurality of nucleic acids, reference to "a substrate" includes a plurality of such substrates, reference to "a variant" includes a plurality of variants, and the like.

Terms such as "connected," "attached," "linked," and "conjugated" are used interchangeably to encompass direct as well as indirect connection, attachment, linkage or conjugation unless the context indicates otherwise.

When a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. When a value being discussed has inherent limits, for example where a component can be present at a concentration of from 0 to 100%, or where the pH of an aqueous solution can range from 1 to 14, those inherent limits are specifically disclosed. When a value is explicitly recited, it is to be understood that values which are about the same quantity or amount as the recited value are also within the scope of the invention. When a combination is disclosed, each sub combination of the elements of that combination is also specifically disclosed and is within the scope of the invention. Conversely, when different elements or groups of elements are individually disclosed, combinations thereof are also disclosed. When any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise, all technical and scientific terms used have their ordinary meaning. Singleton, et. al., Dictionary of Microbiology and Molecular Biology, 2nd Ed., John Wiley and Sons, New York (1994), and Hale & Marham, The Harper Collins Dictionary of Biology, Harper Perennial, NY, 1991 provide guidance as to ordinary meaning.

Unless otherwise indicated, nucleic acids are written left to right in 5' to 3' orientation; amino acid sequences are written left to right in amino to carboxy orientation, respectively.

If a DNA sequence is provided, the specification should be understood as additional disclosing the sequence of the RNA, which will be the same with the exception that thymine (T) is replaced with uracil (U), and vice versa.

Nucleic acids are preferably provided with codon preferences for a cell in which expression is intended. The term "codon usage" or "codon bias" refers to the relative frequencies with which different synonymous codons are used to encode an amino acid within an open reading frame. A nucleic acid sequence having codon preferences for a particular target cell has a balance of synonymous codon choices that result in efficient translation in that cell type. This balance is often not calculable from observed genomic codon frequencies, but must be empirically determined, for example as described in U.S. Pat. Nos. 7,561,972 and 7,561,973 and 8,401,798 and in Welch et. al. (2009) "Design Parameters to Control Synthetic Gene Expression in *Escherichia coli*". PLoS ONE 4(9): e7002. doi.org/10.1371/journal.pone.0007002. A nucleic acid originally isolated from one cell type to be introduced into a target cell of another type can undergo selection of codon preferences for the target site cell such that at least 1 and sometimes, 5, 20, 15, 20, 50, 100 or more choices among synonymous codons differ between the nucleic acid introduced into the target cell from the original nucleic acid.

Two nucleic acids are "complementary" if the bases of one hydrogen bond to the bases of the other. For perfect complementarity, adenine (A) in the first nucleic acid must correspond with thymine (T) (or uracil for RNA) in the second (and vice versa), and cytosine (C) in the first nucleic acid must correspond with guanine (G) in the second (and vice versa). The two nucleic acid s must also be antiparallel. If two nucleic acid are complementary, one may be described as the "reverse complement" of the other to indicate that their bases are complementary when one is in the 5' to 3' direction and the other is in the 3' to 5' direction. When one nucleic acid sequence is described as complementary to another, it is intended to indicate that the sequences are antiparallel and able to base-pair with one another.

The "configuration" of a nucleic acid refers to the presence, order and direction of functional segments with the nucleic acid.

A 'transposase' is a polypeptide that catalyzes the excision of a corresponding transposon from a donor nucleic acid, for example a vector, and (providing the transposase is not integration-deficient) the subsequent integration of the transposon into a target nucleic acid.

"Transposition" refers to action of a transposase in excising a transposon from one nucleic acid and then integrating it, either into a different site in the same nucleic acid, or into a second nucleic acid.

A "transposon" means a nucleic acid that can be excised from a first nucleic acid, for instance, a vector, and be integrated into a second position in the same nucleic acid, or into a second nucleic acid, for instance, the genomic or extrachromosomal DNA of a cell, by the action of a corresponding trans-acting transposase. A transposon comprises a first transposon end and a second transposon end, which are nucleic acid sequences recognized by and transposed by a transposase. The first and second transposon ends include inverted terminal repeats. Two copies of a transposon target site are usually present on the outside of the transposon ends (one on each side). A transposon usually further comprises a nucleic acid between the two transposon ends, which along with the two transposon ends is transposed by the action of the transposase. In natural transposons, the nucleic acid between the transposon ends is typically a corresponding transposase. Transposons of the present invention are "synthetic transposons" comprising a heterologous nucleic acid, which is transposable by virtue of its juxtaposition between two transposon ends. Synthetic transposons may or may not further comprise flanking nucleic acid sequence(s) outside the transposon ends, such as a sequence encoding a transposase, a vector sequence or sequence encoding a selectable marker.

A "transposon end" means the cis-acting nucleotide sequences that are sufficient for recognition by and transposition by a corresponding transposase. Transposon ends of piggyBac-like transposons comprise perfect or imperfect repeats such that the respective repeats in the two transposon ends are reverse complements of each other. These are referred to as inverted terminal repeats (ITR) or terminal inverted repeats (TIR). A transposon end may or may not include additional sequence proximal to the ITR that promotes or augments transposition.

The terms "corresponding transposon" and "corresponding transposase" are used to indicate an activity relationship between a transposase and a transposon. A transposase transposes its corresponding transposon. Many transposases correspond with a single transposon, and many transposons correspond with a single transposase. The term "orthogonal" refers to a lack of interaction between two systems. A first transposon and its corresponding first transposase and a second transposon and its corresponding second transposase are orthogonal if the first transposase does not excise or transpose the second transposon and the second transposase does not excise or transpose the first transposon.

A "target site" for a transposon is a site or sequence in a molecule into which a transposon can be inserted by a transposase. The piggyBac transposase from *Trichoplusia ni* inserts its transposon predominantly into the target sequence 5'-TTAA-3'. Other useable target sequences for piggyBac transposons are 5'-CTAA-3', 5'-TTAG-3, 5'-ATAA-3', 5'-TCAA-3, 5'-AGTT-3', 5'-ATTA-3, 5'-GTTA-3', 5'-TTGA-3', 5'-TTTA-3', 5'-TTAC-3, 5'-ACTA-3, 5'-AGGG-3, 5'-CTAG-3, 5'-GTAA-3', 5'-AGGT-3', 5'-ATCA-3, 5'-CTCC-3', 5'-TAAA-3', 5'-TCTC-3', 5'-TGAA-3', 5'-AAAT-3', 5'-AATC-3', 5'-ACAA-3', 5'-ACAT-3, 5'-ACTC-3', 5'-AGTG-3', 5'-ATAG-3', 5'-CAAA-3, 5'-CACA-3', 5'-CATA-3', 5'-CCAG-3', 5'-CCCA-3', 5'-CGTA-3', 5'-CTGA-3', 5'-GTCC-3', 5'-TAAG-3', 5'-TCTA-3', 5'-TGAG-3', 5'-TGTT-3', 5'-TTCA-3', 5'-TTCT-3' and 5'-TTTT-3' (Li et al., 2013. Proc. Natl. Acad. Sci vol. 110, no. 6, E478-487) and 5'-TTAT. PiggyBac-like transposases transpose their transposons using a cut-and-paste mechanism, which results in duplication of their 4 base pair target sequence on insertion into a DNA molecule. The target sequence is thus found on each side of an integrated piggyBac-like transposon.

A "coupling element" or "translational coupling element" means a DNA sequence that allows the expression of a first polypeptide to be linked to the expression of a second polypeptide. Internal ribosome entry site elements (IRES elements) and cis-acting hydrolase elements (CHYSEL elements) are examples of coupling elements.

A DNA sequence, segment of DNA, RNA sequence or RNA sequence means a contiguous nucleic acid sequence, which can be an oligonucleotide of 2 to 20 nucleotides in length to a full-length genomic sequence of thousands or hundreds of thousands of base pairs.

A vector is a nucleic acid that facilitates any of transfection, integration, replication or expression of a coding segment incorporated into the vector. An expression vector is a vector comprising a promoter which has been or can be operably linked to a coding segment to be expressed. Transfection of the expression vector into a cell allows the cell to express the coding segment. An expression vector can be a genetically engineered plasmid, virus, recombinant virus, or an artificial chromosome derived from, for example, a bacteriophage, adenovirus, adeno-associated virus, retrovirus, lentivirus, poxvirus, or herpesvirus. Such expression vectors can include sequences from bacteria, viruses or phages. Such vectors include chromosomal, episomal and virus-derived vectors, for example, vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids.

A "gene" refers to a transcriptional unit including a promoter and sequence to be expressed from it as an RNA or polypeptide. The sequence to be expressed can be genomic or cDNA or one or more non-coding RNAs including siRNAs or microRNAs among other possibilities. Other elements, such as introns, and other regulatory sequences may or may not be present.

A gene transfer system refers to an expression vector and optionally one or more other features to facilitate gene transfer. For example, a gene transfer system may comprise an expression vector and a lipid or viral packaging mix for enabling a first nucleic acid to enter a cell, or it may comprise a nucleic acid that includes a transposon and a second nucleic acid encoding a corresponding transposase for genomic integration of the transposon. A transposase and transposon of a gene transfer system may be on the same nucleic acid molecule or on different nucleic acid molecules.

Two elements are "heterologous" to one another if not naturally associated. For example, a coding segment linked to a heterologous promoter means a promoter other than that which naturally drives expression of the coding segment. A heterologous nucleic acid flanked by transposon ends or ITRs means a heterologous nucleic acid not naturally flanked by those transposon ends or ITRs, such as a nucleic acid encoding a polypeptide other than a transposase, including an antibody heavy or light chain. A nucleic acid is heterologous to a cell if not naturally found in the cell or if naturally found in the cell but in a different location (e.g., episomal or different genomic location) than the location described.

A "hyperactive" transposase is a transposase that is more active than the naturally occurring transposase from which it is derived. "Hyperactive" transposases are thus not naturally occurring sequences.

An "IRES" or "internal ribosome entry site" means a specialized sequence that directly promotes ribosome binding, independent of a cap structure.

An 'isolated' object, such as a polypeptide or nucleic acid, means the object has been either removed from its natural environment, produced using recombinant techniques, or chemically or enzymatically synthesized. Objects can also be purified, that is, provided at least 90%, 95% or 99% free w/w of other materials with which they are naturally associated or are used in their production or purification. The terms isolated and purified do not exclude presence of other components not naturally associated with the object that facilitate its use, such as a heterologous promoter for a coding segment, or pharmaceutical excipient.

Unless otherwise apparent from the context, the terms "nucleoside" and "nucleotide" include those moieties which contain not only the standard purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, for example, where one or more of the hydroxyl groups are replaced with halogen, aliphatic groups, or is functionalized as ethers, amines, or the like. The term "nucleotidic unit" encompasses nucleosides and nucleotides.

An "Open Reading Frame" or "ORF" means a portion of a nucleic acid that, when translated into amino acids, contains no stop codons. An open reading frame presumptively encodes a polypeptide. The genetic code reads DNA sequences in groups of three base pairs, which means that a double-stranded DNA molecule can read in any of six possible reading frames-three in the forward direction and three in the reverse. An ORF typically also includes an initiation codon at which translation may start.

The term "operably linked" refers to functional linkage between two sequences such that one sequence operationally modifies the behavior of the other. For example, a promoter is operably linked to a coding segment when the promoter can initiate transcription of the coding segment, optionally with subsequent translation of the transcript. A promoter is operably linked to one or more tet-operators, when initiation of transcription by the promoter can be regulated by binding of a tet-repressor or modified tet-repressor to the tet-operon. A mature polypeptide and signal peptide are operably linked when the signal peptide regulates secretion or subcellular location of the mature polypeptide.

The term "overhang" or "DNA overhang" means the single-stranded portion at the end of a double-stranded DNA molecule. Complementary overhangs are those which will base-pair with each other.

A "piggyBac-like transposase" means a transposase with at least 20% amino acid sequence identity as identified using the TBLASTP algorithm to the piggyBac transposase from *Trichoplusia ni* (SEQ ID NO:116), and as more fully described in Sakar, A. et. al., 2003. Mol. Gen. Genomics 270: 173-180. "Molecular evolutionary analysis of the widespread piggyBac transposon family and related 'domesticated' species", and further characterized by a DDE-like DDD motif, with aspartate residues at positions corresponding to D268, D346, and D447 of *Trichoplusia ni* piggyBac transposase on maximal alignment. PiggyBac-like transposases are also characterized by their ability to excise their transposons precisely with a high frequency. A "piggyBac-like transposon" means a transposon having transposon ends which are the same or at least 80% and preferably at least 90, 95, 96, 97, 98, 99% or 100% identical to the nucleotide sequences of the transposon ends of a naturally occurring transposon that encodes a piggyBac-like transposase. A piggyBac-like transposon includes an inverted terminal repeat (ITR) sequence of approximately 12-16 bases at each end. These repeats may be identical at the two ends, or the repeats at the two ends may differ at 1 or 2 or 3 or 4 positions in the two ITRs. The transposon is flanked on each side by a 4 base sequence corresponding to the integration target sequence which is duplicated on transposon integration (the Target Site Duplication or Target Sequence Duplication or TSD). PiggyBac-like transposons and transposases occur naturally in a wide range of organisms including *Argyrogramma agnate* (GU477713), *Anopheles gambiae* (XP_312615; XP_320414; XP_310729), *Aphis gossypii* (GU329918), *Acyrthosiphon pisum* (XP_001948139), *Agrotis ipsilon* (GU477714), *Bombyx mori* (BAD11135), *Ciona intestinalis* (XP_002123602), *Chilo suppressalis* (JX294476), *Drosophila melanogaster* (AAL39784), *Daphnia pulicaria* (AAM76342), *Helicoverpa armigera* (ABS18391), *Homo sapiens* (NP_689808), *Heliothis virescens* (ABD76335), *Macdunnoughia crassisigna* (EU287451), *Macaca fascicularis* (AB179012), *Mus musculus* (NP_741958), *Pectinophora gossypiella* (GU270322), *Rattus norvegicus* (XP_220453), Tribolium castaneum (XP_001814566) and *Trichoplusia ni* (AAA87375) and *Xenopus tropicalis* (BAF82026), although transposition activity has been described for almost none of these.

A regulatory element such as promoter is active in a specified target cell, such as a mammalian cell, means a regulatory element configurable to result in a level of expression of at least 1 transcript and optionally at least ten, 100 or 1000 transcripts per cell in a mammalian cell into which the regulatory element has been introduced.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the longer of (a) entire length of the shorter of the two sequences being compared, or (b) at least 25 contiguous nucleotides. Matched positions in maximally aligned sequences can be referred to as corresponding to one another.

Specific binding between two entities refers to binding detectably higher in magnitude and distinguishable from non-specific binding of each of the entities to at least one unrelated target. Specific binding can be the result of formation of bonds between particular functional groups or particular spatial fit (e.g., lock and key type) whereas nonspecific binding is usually the result of van der Waals forces. Exemplary specific binding affinity can be at least $10^7$, $10^8$, $10^9$, or $10^{10}$ $M^{-1}$.

Preferential binding between two entities refers to a substantial difference in binding affinity between two different conditions, such as presence or absence of tetracycline. For example, the affinities can differ by a factor of a least 5, 10, 25, 50 or 100. Preferential expression in one condition compared with another likewise refers to variation in expression by a factor of at least 5, 10, 25, 50 or 100 between the conditions.

A polypeptide refers to any polymer of amino acids natural or synthetic regardless of length and thus includes full length proteins, fragments thereof, and peptides.

A promoter can be represented by a single-stranded sequence of nucleotides present on a transcribed strand or a double-stranded sequence of nucleotide formed of the single-stranded sequence of nucleotides just described duplexed with its complement. Depending on the context, reference to a promoter may refer to either single- or double-stranded forms or both.

Transfection is used generically for any process for introducing a nucleic into cells.

The term "comprising" indicates that other features besides those recited may or may not be present. Thus, for example, reference to a nucleic acid comprising a tet-operator comprising SEQ ID NO:5 means that additional flanking residues can be present on either or both sides of SEQ ID NO:5. The term "consisting essentially of" is used in accordance with convention to refer to the basic and novel features of an invention.

DETAILED DESCRIPTION

I. General

The invention provides inducible promoter systems and their components incorporating components of a tetracycline operon. By coordinating expression of different transcriptional units in these systems as a result of selection of promoters and/or linking the units into the same DNA molecule, these systems can achieve higher levels of expression of coding segments of interest, increased differential levels of expression between on- and off-states, and/or greater responsiveness to inducing agents than conventional systems.

II. Promoters

The invention provides a hybrid mouse-human CMV promoter. The sequences of mouse and human CMV promoters are set out aligned in FIG. 1 with the transcriptional start site (first transcribed nucleotide) indicated as the underlined G annotated as +1. The human CMV promoter is a constitutive promoter often used for expression in mammalian cells. However, this promoter contains several CG dinucleotide motifs, which may reduce transcriptional efficiency, particularly a CG motif occupying positions −178 and −179 counted from the transcriptional start site of human CMV promoter (corresponding to positions 42 and 43 of SEQ ID NO:13, or corresponding positions of any mouse-human chimeric promoter sequence maximally aligned with SEQ ID NO:13). CG motifs can be eliminated by replacing sequence from the human CMV promoter with aligned sequence from the mouse CMV promoter lacking one or more of the CG motifs, particularly the CG motif occupying positions −178 and −179 of the human CMV promoter sequence (SEQ ID NO:13). Among other possibilities, replacement can be effected by combining an upstream segment of a mouse CMV promoter of SEQ ID NO:16 and a downstream segment of a human CMV promoter of SEQ ID NO:13 or 14. The junction between the segments is preferably within a segment of nucleotides ACGTCAATGGGA (SEQ ID NO:173), which is common to the human and mouse CMV promoter sequences. One hybrid comprises 149 bp of the mouse CMV sequence of SEQ ID NO:16 upstream of 114 bp of the human CMV sequence of SEQ ID NO:13. Preferred promoters have sequences comprising, consisting of or consisting essentially of the sequence of SEQ ID NO:10. SEQ ID NO:10 lacks a 13 nucleotide sequence (SEQ ID NO:35) immediately upstream of the human CMV transcription initiation site. The omitted sequence can be replaced by regulatory elements, such as tet operons as further described below. Another preferred promoter sequence comprises, consists essentially of or consists of SEQ ID NO:12. SEQ ID NO:12 includes the 13 nucleotide sequence of SEQ ID NO:35 omitted in SEQ ID NO:10. Although exemplified for a combination of human and mouse CMV promoters, the same principles can be applied in forming a hybrid promoter between a human CMV promoter and CMV promoters of other species, particularly rodent species, such as rat CMV. Hybrid promoters, as described above, preferably confer enhanced transcription compared with either or both of the component promoters forming the hybrid.

The invention also provides a minimal chimpanzee CMV promoter. A minimal promoter is a promoter that by itself shows no or minimal transcription (e.g., a mean of <1, 5 or 10 transcripts per cell), but which can show substantially enhanced transcription (e.g., at least 10-fold, 50-fold or 100-fold), when combined with an upstream regulatory sequence, which serves to recruit a polymerase and transcriptional factors. A minimal promoter sequence is typically a contiguous sequence of nucleotides starting at or near the first nucleotide upstream of the transcriptional initiation site and including a TATA box. An exemplary minimal chimpanzee CMV promoter has a sequence comprising, consisting of or consisting essentially of SEQ ID NO:24. Optionally, up to 1, 2, 3, 4 or 5 nucleotides can be deleted from either end. Optionally, a few, e.g., up to 1, 2, 3, 4, 5, 6, 7, 8, 9, or 10 nucleotides from the chimpanzee CMV promoter can be included upstream from the minimal promoter sequence, but inclusion of additional nucleotides is not preferred because this may reduce the differential levels of expression in the presence and absence of upstream activation.

The invention also uses intermediate strength promoters. Such promoters have reduced transcriptional activity relative to the hybrid promoters described above or their component promoters but greater activity than a minimal promoter. For example, the transcriptional activity can be reduced by 2-20 fold relative to the hybrid promoters described above or their components. Examples of such promoters have sequences comprising, consisting of or consisting essentially of any of SEQ ID NOS:17-21.

The invention can also make use of other strong promoters besides the hybrid promoters and their components described above. Such promoters are preferably active in eukaryotic cells, more preferably in mammalian cells. Examples of such strong promoters are CMV, EF1a (human elongation factor 1-alpha), SV40, PGK1 (phosphoglycerate kinase), human ubiquitin C, and human beta actin.

The promoters described above can be incorporated into transcriptional units, which in addition to the promoter include a coding segment, and sometimes other regulatory sequences, such as tet-operators as described further below or an enhancer, among other components. The heterologous coding segment can encode a polypeptide or RNA and can include a 5'UTR and/or a 3' UTR and a polyadenylation sequence among other components. Such transcriptional units can be transformed into cells for expression.

Promoters can be compared by forming otherwise identical transcriptional units between promoters to be compared, transforming into the same cell type, e.g., CHO, HeLa, 293, COS, U2OS, 3T3, or other mammalian cell and comparing transcription levels.

III. Components of Tet Regulatory Systems

Some of the components of the present systems can be the same as those of conventional tet-dependent regulatory systems. Such components include tet-operators, tet-repressors, which bind tet-operators in the absence of tetracycline or other analogs thereof, modified tet-repressors, which bind tet-operators in the presence of tetracycline or other analogs thereof, and inducers, such as tetracycline and analogs thereof.

An exemplary tet-operator comprises, consists of, or consists essentially of the sequence of SEQ ID NO:1 Other tet-operators can have up to 1, 2, 3 or 4 substitutions, deletions or additions and/or have at least 90, 95, 97, 98 or 99% identity relative to the exemplified sequence and retain the ability of the exemplified sequence for preferential binding of a tet-repressor in the absence of tetracycline and preferential binding of a modified tet-repressor in the presence of tetracycline. Examples of other tet-operator sequences include 5'-TCGCTATCAGTGATAGAGA-3' (SEQ ID NO:174) and 5'-ACTCTATCATTGATAGAGT-3' (SEQ ID NO:175) (Wissmann et al, 1986, Nucl. Acids Res. 14: 4253-4266). Tet-operators are typically used in tandem arrays (i.e, including at least two tet operator sequences). Some arrays include 2 to 10 tet-operator sequences. Some such arrays include 2, 3, 4, 5, 6, 7, 8, 9 or 10 operator sequences. Some arrays have at least 2, 3, 4, 5, 6, 7, 8, 9 or 10 operator sequences. Some arrays have more than 10 operator sequences. The multiple operator sequences in such a tandem array are typically the same sequence. The operators are typically separated by spacers of e.g., 1-25 nucleotides. The identity and length of spacers can vary between different operators in an array. The number of operators and length of spacer can vary depending on the location of the operators relative to other components of a transcriptional unit as further described below.

An exemplary tet-repressor polypeptide comprises or consists of the amino acid sequence SEQ ID NO:5. Other tet-repressor polypeptides can have up to 1, 2, 3, 4, 5, 6, 7, 8, 9 or 10 substitutions, deletions or additions and/or have at least 90, 95, 97, 98 or 99% identity relative to this sequence. Examples of variants include those described in Gossen and Bujard, Proc. Natl. Acad. Sci. USA Vol. 89, pp. 5547-5551, 1992 and a T40A substitution described by Altschmied et al., EMBO J. 7:4011-4017, (1988). Substitutions are numbered according to position in SEQ ID NO:5 or if present in a sequence with a different number of residues than SEQ ID NO:5, the position of SEQ ID NO:5 corresponding to the substitution when the sequences are maximally aligned. A tet-repressor polypeptide has the property of specifically binding to a tet-operator or an array thereof in the absence of tetracycline. A tet-repressor shows at least preferential binding to a tet-operator or array thereof in the absence of tetracycline compared with the presence of tetracycline.

An exemplary modified tet-repressor polypeptide comprises or consists of the amino acid sequence SEQ ID NO:6. Other modified tet-repressor polypeptides can have up to 1, 2, 3, 4, 5, 6, 7, 8, 9 or 10 substitutions, deletions or additions and/or have at least 90, 95, 97, 98 or 99% identity relative to this sequence. Examples of variants include those described in Das et al. Current Gene Therapy, 2016, 16, 156-167, including tTA (E71K D95N L101S G102D), S2 (E19G A56P D148E H179R), M2 (S12G E19G A56P D148E H179R), 25-S2 (E19G A56P D148E H179R), 25-M2 (S12G E19G A56P D148E H179R), V1 (E19G A56P F86Y D148E H179R), rtTA3 (S12G E19G A56P F86Y D148E H179R), V10 (E19G A56P F67S F86Y D148E R171K H179R), V16 (V9I E19G A56P F67S F86Y D148E R171K H179R). Substitutions are numbered according to position in SEQ ID NO:6 or if present in a sequence with a different number of residues than SEQ ID NO:6, the position of SEQ ID NO:6 corresponding to the substitution when the sequences are maximally aligned. In contrast to a tet-repressor polypeptide, a modified tet-repressor polypeptide has the property of specifically binding to a tet-operator or an array thereof in the presence of tetracycline. A modified tet-repressor shows at least preferential binding to a tet-operator or array thereof in the presence of tetracycline compared with the absence of tetracycline.

Inducers of expression used in the present system include tetracycline itself, doxycycline and other tetracycline analogs. Unless otherwise apparent from the context, reference to tetracycline should be understood as alternatively disclosing that tetracycline analogs can be used. A tetracycline analog is a compound structurally related to tetracycline and which specifically binds to a tet-repressor or modified tet-repressor as described herein. Examples of tetracycline analogs are anhydrotetracycline (atc), chlorotetracycline, oxytetracycline, or deoxytetracycline and minocycline. Further analogs are disclosed by Hlavka and Boothe, "The Tetracyclines," in Handbook of Experimental Pharmacology 78, R. K. Blackwood et al. (eds.), Springer-Verlag, Berlin, N.Y., 1985; Mitscher, "The Chemistry of the Tetracycline Antibiotics", Medicinal Research 9, Dekker, N.Y., 1978; Noyee Development Corporation, "Tetracycline Manufacturing Processes" Chemical Process Reviews, Park Ridge, N.J., 2 volumes, 1969; Evans, "The Technology of the Tetracyclines," Biochemical Reference Series 1, Quadrangle Press, New York, 1968; and Dowling, "Tetracycline," Antibiotic Monographs, no. 3, Medical Encyclopedia, New York, 1955 and WO2007/133797 and WO2007/133798.

III. Components of Cumate Regulatory Systems

A cumulate regulatory system has analogous compounds and mode of operation to a tetracycline regulatory system. These include cumate operators, cumate repressors, which bind a cumate operator in the absence of cumate and modified cumate repressors, which bind cumate operators in the presence of cumate. The description in relation to tetracycline regulatory sequences applies mutatis mutandis to cumate operator systems.

An exemplary cumate operator comprises, consists of, or consists essentially of the sequence of any of SEQ ID NOS:156-158. Other cumate operators can have up to 1, 2, 3 or 4 substitutions, deletions or additions and/or have at least 90, 95, 97, 98 or 99% identity relative to the exemplified sequence and retain the ability of the exemplified sequence for preferential binding of a cumate repressor in the absence of cumate and preferential binding of a modified cumate repressor in the presence of cumate. Cumate operators can be used individually or in tandem arrays (i.e., including at least two cumate operators). Some arrays include 2 to 10 cumate operators. Some such arrays include 2, 3, 4, 5, 6, 7, 8, 9 or 10 operator sequences. Some arrays have at least 2, 3, 4, 5, 6, 7, 8, 9 or 10 operator sequences. Some arrays have more than 10 operator sequences. The multiple operators in such a tandem array can have the same or different sequences. The operators may be separated by spacers of e.g., 1-25 nucleotides. The identity and length of spacers can vary between different operators in an array. The number of operators and length of spacer can vary depending on the location of the operators relative to other components of a transcriptional unit as further described below.

An exemplary cumate repressor polypeptide comprises or consists of the amino acid sequence SEQ ID NO:170. Other cumate-repressor polypeptides can have up to 1, 2, 3, 4, 5, 6, 7, 8, 9 or 10 substitutions, deletions or additions and/or have at least 90, 95, 97, 98 or 99% identity relative to this sequence. A cumate repressor polypeptide has the property of specifically binding to a cumate operator or an array thereof in the absence of cumate. A cumate-repressor shows at least preferential binding to a cumate operator or array thereof in the absence of cumate compared with the presence of cumate.

An exemplary modified cumate repressor polypeptide comprises or consists of the amino acid sequence SEQ ID NO:171. Other modified cumate repressor polypeptides can have up to 1, 2, 3, 4, 5, 6, 7, 8, 9 or 10 substitutions, deletions or additions and/or have at least 90, 95, 97, 98 or 99% identity relative to this sequence. SEQ ID NO:171 includes three mutations relative to SEQ ID NO:170: E142G, I144M and V125A In contrast to a cumate repressor polypeptide, a modified cumate repressor polypeptide has the property of specifically binding to a cumate-operator or an array thereof in the presence of cumate. A modified cumate repressor shows at least preferential binding to a cumate-operator or array thereof in the presence of cumate compared with the absence of cumate.

Inducers of expression used in the present system include cumate itself and analogs. An analog is a compound structurally related to cumate and which specifically binds to a cumate-repressor or modified cumate-repressor as described herein. Examples of cumate analogs include di-methyl p-aminobenzoic acid (DM PABA), trimethyl cumate, and ethylbenzoate, or a salt thereof, mainly para- or 4-substituted benzoate consisting of a bulky group of heteroatom, such as those selected from the group consisting of 3,4-dimethylbenzoate, 4-ethylbenzoate, 4-t-butylbenzoate, 4-phenylbenzoate, 4-benzylbenzoate, 4-ethoxybenzoate, 4-propyloxybenzoate, 4-n-butyloxybenzoate, 4-chlorobenzoate, 4-bromobenzoate, 4-iodobenzoate, 4-bromomethylbenzoate, 3,4-dichlorobenzoate, 4-trifluoromethylbenzoate, 4-ethyl-m-xylene, 4-vinyltoluene, 4-n-propyltoluene, 4-allytoluene, 4-fluoro-p-toluate, 3-chloro-p-toluate, and 4-bromo-m-toluate, an analogue of cumate such as Benzoic acid, p-methylbenzoic acid, p-ethylbenzoic acid, p-Propylbenzoic acid, cumic acid, p-isobutylbenzoic acid, p-tert-butylbenzoic acid, ibuprofen, p-aminobenzoic acid, p-N-methylaminobenzoic acid, p-N-dimethylaminobenzoic acid, p-N-methyl-N-ethylaminobenzoic acid and p-N-ethylaminobenzoic acid.

IV. Transcriptional Activation Domains

Some of the present systems include a transcriptional activation domain. Such a domain is expression as a fusion protein with a tet-repressor polypeptide or modified tet-repressor polypeptide. Fusion is preferably between the C-terminus of the tet-repressor or modified-tet-repressor and the N-terminus of the transcriptional activation domain. More than one transcriptional domain can be included as a tandem array of such domains in a fusion protein. Examples of transcriptional activations domains include the HSV VP16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)). Other transcriptional activation domains include VP64, p300, CBP, PCAF, SRC1 PvALF, AtHD2A and ERF-2. See, for example, Robyr et al. (2000) Mol. Endocrinol. 14:329-347; Collingwood et al. (1999) J. Mol. Endocrinol. 23:255-275; Leo et al. (2000) Gene 245:1-11; Manteuffel-Cymborowska (1999) Acta Biochim. Pol. 46:77-89; McKenna et al. (1999) J. Steroid Biochem. Mol. Biol. 69:3-12; Malik et al. (2000) Trends Biochem. Sci. 25:277-283; and Lemon et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) Gene 245:21-29; Okanami et al. (1996) Genes Cells 1:87-99; Goff et al. (1991) Genes Dev. 5:298-309; Cho et al. (1999) Plant Mol. Biol. 40:419-429; Ulmason et al. (1999) Proc. Natl. Acad. Sci. USA 96:5844-5849; Sprenger-Haussels et al. (2000) Plant J. 22:1-8; Gong et al. (1999) Plant Mol. Biol. 41:33-44; and Hobo et al. (1999) Proc. Natl. Acad. Sci. USA 96:15,348-15,353. Exemplary VP16 activation domains comprises or consists of a sequence selected from SEQ ID NOS:7 or 40. Exemplary fusions of a modified tet-repressor to a VP16 activation domain comprises or consists of a sequence selected from SEQ ID NOS:8 or 9.

V. Coding Segments

Coding segments can encode any polypeptide or RNA of interest. Coding segments can include an open reading frame encoding a polypeptide. Coding segments can also include a segment encoding a 5' UTR, 3' UTR or polyadenylation region. Examples of polypeptides includes therapeutic proteins, proteins associated with a disease phenotype, enzymes, proteins used as selection markers or counter-selection markers, or suicide proteins. Examples of RNA include mRNA, tRNA, rRNA as well as various RNA molecules used for interference of expression, such as anti-sense, siRNA, shRNA or micro-RNA including artificial micro-RNA. Some examples of therapeutic proteins include antibodies or their component heavy and light chains, or heavy and light chain fused to one another as a single-chain antibody, antibodies engineered to produce heteromeric multi-chain molecules capable of binding more than one target protein (e.g. bispecific or multi-specific antibodies), T cell engagers, chimeric antigen receptors combining an antigen binding region with transmembrane and T cell signalling domains, Fc fusion proteins, antigens from pathogens (e.g. for use in vaccines), anticoagulants, blood factors, bone morphogenetic proteins, enzymes, growth factor hormones, interferons, interleukins and thrombolytics. Proteins associated with disease are often mutated forms of human proteins. Some examples of such proteins are huntingtin, cystic fibrosis trans-membrane regulator, hemoglobin, alpha-1 antitrypsin, phenylalanine hydroxylase, beta-hexosaminidase, amyloid precursor protein, alpha-synuclein prion protein, transthyretin, crystallin and p53. It is particularly useful to be able to control the timing of expression of coding segments whose expression can be toxic for the cell that expresses them, for example so that the growth phase of an expression host can be decoupled from the expression phase. Examples of potentially toxic coding segments include open reading frames encoding membrane proteins such as ion channels, G-protein coupled receptors (GPCRs) and viral membrane proteins (such as the coronavirus spike proteins). Other examples of potentially toxic coding segments include open reading frames encoding proteins normally targeted to the lysozome, kinases and cytokines.

A selection marker is a nucleic acid or expression product that allows for selection of a molecule or cell containing the marker often under particular conditions. These markers can encode an activity, such as, production of RNA, peptide, or protein, or can provide a binding site for RNA, peptides, proteins, inorganic and organic compounds or compositions. Examples of selectable markers include: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds. Some examples of selection markers include glutamine synthetase, dihydrofolate reductase, blasticidin-resistance, neo-resistance, hygromycin-resistance, puromycin-resistance and zeocin-resistance.

The term "counter-selectable marker" means a polynucleotide sequence that confers a selective disadvantage on a host cell. Examples of counter-selectable markers include sacB, rpsL, tetAR, pheS, thyA, gata-1, ccdB, kid and barnase (Bernard, 1995, Journal/Gene, 162: 159-160; Bernard et. al., 1994. Journal/Gene, 148: 71-74; Gabant et. al., 1997, Journal/Biotechniques, 23: 938-941; Gababt et. al., 1998, Journal/Gene, 207: 87-92; Gababt et. al., 2000, Journal/Biotechniques, 28: 784-788; Galvao and de Lorenzo, 2005, Journal/Appl Environ Microbiol, 71: 883-892; Hartzog et. al., 2005, Journal/Yeat, 22:789-798; Knipfer et. al., 1997, Journal/Plasmid, 37: 129-140; Reyrat et. al., 1998, Journal/Infect Immun, 66: 4011-4017; Soderholm et. al., 2001, Journal/Biotechniques, 31: 306-310, 312; Tamura et. al., 2005, Journal/Appl Environ Microbiol, 71: 587-590; Yazynin et. al., 1999, Journal/FEBS Lett, 452: 351-354).

A suicide gene is a gene that causes a cell to kill itself e.g., by inducing apoptosis or by metabolizing a pro-drug into a drug that is toxic to a cell, e.g., caspase-9 (see Yagyu et al., Mol. Ther. 23: 1475-85 (2015)). The present systems are particularly useful for regulated expression of coding segments whose expression is detrimental or lethal to a cell.

VI. Gene Transfer Systems

The present transcription units can be incorporated into one or more gene transfer systems. For inducible control systems including two transcriptional units, both are preferably included in the same gene transfer system as part of the same contiguous nucleic acid.

A gene transfer systems comprises a nucleic acid to be transferred into a host cell and one or more other elements to facilitate uptake, integration, expression or election of the nucleic acid. A gene transfer system can include a transposon and corresponding transposase. Although transposons are preferred gene transfer systems because of their large cargo sizes and because multiple different coding segments with all of their associated regulatory elements can be incorporated without compromising packaging and delivery of the gene transfer system, other genes transfer systems including a lentiviral system, an adenoviral system or an adeno-associated viral system, or other expression vector can be used.

A gene transfer system or one or more if its components can be transfected into one or more cells by techniques such as particle bombardment, electroporation, microinjection, combining the components with lipid-containing vesicles, such as cationic lipid vesicles, DNA condensing reagents (example, calcium phosphate, polyline or polyethyleneimine)

After transfection, introduced nucleic acids can remain the cytoplasm (e.g., as an episome) or can be integrated into the genome. Integration of a nucleic acid into the genome of a host cell generally makes it stably heritable, by subjecting it to the same mechanisms that ensure the replication and division of genomic DNA. Such stable heritability is desirable for achieving good and consistent expression over long growth periods.

Nucleic acid can be efficiently integrated into nucleic acids, such as a genome, by a transposase system. The nucleic acid into which a transposed nucleic acid is integrated is sometimes referred to as a target nucleic acid. A transposase system includes a transposon and a corresponding transposase. The transposon includes a heterologous nucleic acid to be transposed flanked by inverted transposon repeats (ITRs). The ITR on one side of the heterologous nucleic acid is a perfect or substantial (e.g., one or two mismatched nucleotides) reverse complement of the ITR on the other side. Between the ITRs and heterologous nucleic acids, additional transposon sequences may be present. Outside the ITRs (distal to the heterologous nucleic acid) are two copies, one for each side, of a target site, typically of four nucleotides. A benefit of a transposon is that the entire nucleic acid between transposon inverted terminal repeats (ITRs) can be integrated. There are several different classes of transposon. piggyBac and piggyBac-like transposons include the piggyBac transposon from the looper moth *Trichoplusia ni*, *Xenopus* piggyBac-like transposons, *Bombyx* piggyBac-like transposons, *Heliothis* piggyBac-like transposons, *Helicoverpa* piggyBac-like transposons, *Agrotis* piggyBac-like transposons, *Amyelois* piggyBac-like transposons, piggyBat piggyBac-like transposons and *Oryzias* piggyBac-like transposons. hAT transposons include TcBuster. Mariner transposons include Sleeping Beauty. Each of these transposons can be integrated into the genome of a mammalian cell by a corresponding transposase. A transposase can be provided as a protein or encoded by a nucleic acid. A transposon comprising a heterologous nucleic acid and its corresponding transposase can be transfected into a cell at the same time, or sequentially. For example, a transposase protein or its encoding nucleic acid may be transfected into a cell prior to, simultaneously with or subsequently to transfection of a corresponding transposon. Additionally, administration of either component of the gene transfer system may occur repeatedly, for example, by administering at least two doses of this component.

A nucleic acid encoding a transposase protein can be transfected into a cell as a nucleic acid vector such as a plasmid, a viral vector or as an mRNA molecule. The nucleic acid can be circular or linear. The nucleic acid encoding the transposase protein can be stably inserted into the genome of the cell or can remain in the cytoplasm. The transposase can be expressed constitutively or from an inducible system. DNA encoding a transposase is preferably linked to a promoter. A variety of promoters can be used including constitutive promoters, tissue-specific promoters, inducible promoters, species-specific promoters, cell-type specific promoters and the like. Alternatively, a transposase can be introduced into a cell directly as protein, for example using cell-penetrating peptides (e.g. as described in Ramsey and Flynn, 2015. Pharmacol. Ther. 154: 78-86 "Cell-penetrating peptides transport therapeutics into cells"); using small molecules including salt plus propane betaine (e.g. as described in Astolfo et. al., 2015. Cell 161: 674-690); or electroporation (e.g. as described in Morgan and Day, 1995. Methods in Molecular Biology 48: 63-71 "The introduction of proteins into mammalian cells by electroporation").

Transposase proteins can be introduced into cells encoded as an mRNA molecule. RNA molecules can include substitutions to reduce toxicity effects on the cell, for example substitution of uridine with pseudouridine, and substitution of cytosine with 5-methyl cytosine. mRNA encoding the transposase can be prepared with a 5'-cap structure to improve expression in a target cell. Exemplary cap structures are a cap analog (G(5')ppp(5')G), an anti-reverse cap analog (3'-O-Me-m.sup.7G(5')ppp(5')G, a clean cap(m7G (5')ppp(5')(2'OMeA)pG), an mCap (m7G(5')ppp(5)G). mRNA encoding the transposase may be prepared such that some bases are partially or fully substituted, for example uridine may be substituted with pseudo-uridine, cytosine may be substituted with 5-methyl-cytosine. Any combinations of these caps and substitutions may be made. Similarly, a nucleic acid encoding a transposase protein or the transposon of this invention can be transfected into the cell as a linear fragment or as a circularized fragment, either as a plasmid or as recombinant viral DNA. If the transposase is introduced as a DNA sequence encoding the transposase, then the coding segment encoding the transposase is preferably operably linked to a promoter suitable for use in the intended target cell.

An exemplary piggyBac-like transposon for modifying the genome of a mammalian cell is a *Xenopus* transposon which comprises an ITR with the with sequence given by SEQ ID NO:41, a heterologous nucleic acid to be transposed and a second ITR with sequence given by SEQ ID NO:42. The transposon may further be flanked by a copy of the tetranucleotide5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:43 or 44 on one side of the heterologous nucleic acid, preferably the left side, and a sequence immediately adjacent to the ITR and proximal to the heterologous nucleic acid that is at least 95% or 100% identical to SEQ ID NO:45 or 46 on the other side of the heterologous nucleic acid, preferably the right side. This transposon may be transposed by a corresponding *Xenopus* transposase comprising a sequence at least 90% or 100% identical to the sequence given by SEQ ID NO:47 or 48, for example, any of SEQ ID NOS:47-79. Preferably the transposase is a hyperactive variant of a naturally occurring transposase. Preferably the hyperactive variant transposase comprises one or more of the following amino acid changes, relative to the sequence of SEQ ID NO:47: Y6L, Y6H, Y6V, Y6I, Y6C, Y6G, Y6A, Y6S, Y6F, Y6R, Y6P, Y6D, Y6N, S7G, S7V, S7D, E9W, E9D, E9E, M16E, M16N, M16D, M16S, M16Q, M16T, M16A, M16L, M16H, M16F, M16I, S18C, S18Y, S18M, S18L, S18Q, S18G, S18P, S18A, S18W, S18H, S18K, S18I, S18V, S19C, S19V, S19L, S19F, S19K, S19E, S19D, S19G, S19N, S19A, S19M, S19P, S19Y, S19R, S19T, S19Q, S20G, S20M, S20L, S20V, S20H, S20W, S20A, S20C, S20Q, S20D, S20F, S20N, S20R, E21N, E21W, E21G, E21Q, E21L, E21D, E21A, E21P, E21T, E21S, E21Y, E21V, E21F, E21M, E22C, E22H, E22R, E22L, E22K, E22S, E22G, E22M, E22V, E22Q, E22A, E22Y, E22W, E22D, E22T, F23Q, F23A, F23D, F23W, F23K, F23T, F23V, F23M, F23N, F23P, F23H, F23E, F23C, F23R, F23Y, S24L, S24W, S24H, S24V, S24P, S24I, S24F, S24K, S24Y, S24D, S24C, S24N, S24G, S24A, S26F, S26H, S26V, S26Q, S26Y, S26W, S28K, S28Y, S28C, S28M, S28L, S28H, S28T, S28Q, V31L, V31T, V31I, V31Q, V31K, A34L, A34E, L67A, L67T, L67M, L67V, L67C, L67H, L67E, L67Y, G73H, G73N, G73K, G73F, G73V, G73D, G735, G73W, G73L, A76L, A76R, A76E, A76I, A76V, D77N, D77Q, D77Y, D77L, D77T, P88A, P88E, P88N, P88H, P88D, P88L, N91D, N91R, N91A, N91L, N91H, N91V, Y141I, Y141M, Y141Q, Y141S, Y141E, Y141W, Y141Y, Y141F, Y141A, Y141C, Y141K, Y141L, Y141H, Y141R, N145C, N145M, N145A, N145Q, N145I, N145F, N145G, N145D, N145E, N145V, N145H, N145W, N145Y, N145L, N145R, N145S, P146V, P146T, P146W, P146C, P146Q, P146L, P146Y, P146K, P146N, P146F, P146E, P148M, P148R, P148V, P148F, P148T, P148C, P148Q, P148H, Y150W, Y150A, Y150F, Y150H, Y150S, Y150V, Y150C, Y150M, Y150N, Y150D, Y150E, Y150Q, Y150K, H157Y, H157F, H157T, H157S, H157W, A162L, A162V, A162C, A162K, A162T, A162G, A162M, A162S, A162I, A162Y, A162Q, A179T, A179K, A179S, A179V, A179R, L182V, L182I, L182Q, L182T, L182W, L182R, L182S, T189C, T189N, T189L, T189K, T189Q, T189V, T189A, T189W, T189Y, T189G, T189F, T189S, T189H, L192V, L192C, L192H, L192M, L192I, S193P, S193T, S193R, S193K, S193G, S193D, S193N, S193F, S193H, S193Q, S193Y, V196L, V196S, V196W, V196A, V196F, V196M, V196I, S198G, S198R, S198A, S198K, T200C, T200I, T200M, T200L, T200N, T200W, T200V, T200Q, T200Y, T200H, T200R, S202A, S202P, L210H, L210A, F212Y, F212N, F212M, F212F, F212A, N218V, N218R, N218T, N218C, N218G, N218I, N218P, N218D, N218E, A248S, A248L, A248H, A248C, A248N, A248I, A248Q, A248Y, A248M, A248D, L263V, L263A, L263M, L263R, L263D, Q270V, Q270K, Q270A, Q270C, Q270P, Q270L, Q270I, Q270E, Q270G, Q270Y, Q270N, Q270T, Q270W, Q270H, S294R, S294N, S294G, S294T, S294C, T297C, T297P, T297V, T297M, T297L, T297D, E304D, E304H, E304S, E304Q, E304C, S308R, S308G, L310R, L310I, L310V, L333M, L333W, L333F, Q336Y, Q336N, Q336M, Q336A, Q336T, Q336L, Q336I, Q336G, Q336F, Q336E, Q336V, Q336C, Q336H, A354V, A354W, A354D, A354C, A354R, A354E, A354K, A354H, A354G, C357Q, C357H, C357W, C357N, C357I, C357V, C357M, C357R, C357F, C357D, L358A, L358F, L358E, L358R, L3584, L358V, L358H, L358C, L358M, L358Y, L358K, L358N, L358I, D359N, D359A, D359L, D359H, D359R, D359S, D359Q, D359E, D359M, L377V, L377I, V423N, V423P, V423T, V423F, V423H, V423C, V423S, V423G, V423A, V423R, V423L, P426L, P426K, P426Y, P426F, P426T, P426W, P426V, P426C, P426S, P4264, P426H, P426N, K428R, K428Q, K428N, K428T, K428F, S434A, S434T, S438Q, S438A, S438M, T447S, T447A, T447C, T447Q, T447N, T447G, L450M, L450V, L450A, L450I, L450E, A462M, A462T, A462Y, A462F, A462K, A462R, A462Q, A462H, A462E, A462N, A462C, V467T, V467C, V467A, V467K, I469V, I469N, I472V, I472L, I472W, I472M, I472F, L476I, L476V, L476N, L476F, L476M, L476C, L476Q, P488E, P488H, P488K, P4884, P488F, P488M, P488L, P488N, P488D, Q498V, Q498L, Q498G, Q498H, Q498T, Q498C, Q498E, Q498M, L502I, L502M, L502V, L502G, L502F, E517M, E517V, E517A, E517K, E517L, E517G, E517S, E517I, P520W, P520R, P520M, P520F, P520Q, P520V, P520G, P520D, P520K, P520Y, P520E, P520L, P520T, S521A, S521H, S521C, S521V, S521W, S521T, S521K, S521F, S521G, N523W, N523A, N523G, N523S, N523P, N523M, N523Q, N523L, N523K, N523D, N523H, N523F, N523C, I533M, I533V, I533T, I533S, I533F, I533G, I533E, D534E, D5344, D534L, D534R, D534V, D534C, D534M, D534N, D534A, D534G, D534F, D534T, D534H, D534K, D534S, F576L, F576K, F576V, F576D, F576W, F576M, F576C, F576R, F576Q, F576A, F576Y, F576N, F576G, F576I, F576E, K577L, K577G, K577D, K577R, K577H, K577Y, K577I, K577E, K577V, K577N, I582V, I582K, I582R, I582M, I582G, I582N, I582E, I582A, I582Q, Y583L, Y583C, Y583F, Y583D, Y583Q, L587F, L587D, L587R, L587I, L587P, L587N, L587E, L587S, L587Y, L587M, L587Q, L587G, L587W, L587K or L587T.

Another exemplary piggyBac-like transposon for modifying the genome of a cell is a *Bombyx* transposon which comprises an ITR with the sequence of SEQ ID NO:80, a heterologous nucleic acid to be transposed and a second ITR with the sequence of SEQ ID NO:81. The transposon may further be flanked by a copy of the tetranucleotide 5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:82 on one side of the heterologous nucleic acid, preferably the left side, and a sequence immediately adjacent to the ITR and proximal to the heterologous nucleic acid that is at least 95% or 100% identical to SEQ ID NO:83 on the other side of the heterologous nucleic acid, preferably the right side. This transposon may be transposed by a corresponding *Bombyx* transposase comprising a sequence at least 90% or 100% identical to SEQ ID NO:84, for example, any of SEQ ID NOS:84-106. Preferably the transposase is a hyperactive variant of a naturally occurring transposase of SEQ ID NO:84 including one or more of the following mutations: Q92A, Q92P, Q92N, Q92I, Q92Y, Q92H, Q92F, Q92R, Q92D, Q92M, Q92W, Q92C, Q92G, Q92L, Q92V, Q92T, V93P, V93K, V93M, V93F, V93W, V93L, V93A, V93I, V93Q, P96A, P96T, P96M, P96R, P96G, P96V, P96E, P96Q, P96C, F97Q, F97K, F97H, F97T, F97C, F97W, F97V, F97E, F97P, F97D, F97A, F97R, F97G, F97N, F97Y, H165E, H165G, H165Q, H165T, H165M, H165V, H165L, H165C, H165N, H165D, H165K, H165W, H165A, E178S, E178H, E178Y, E178F, E178C, E178A, E178Q, E178G, E178V, E178D, E178L, E178P, E178W, C189D, C189Y, C189I, C189W, C189T, C189K, C189M, C189F, C189P, C189Q, C189V, A196G, L200I, L200F, L200C, L200M, L200Y, A201Q, A201L, A201M, L203V, L203D, L203G, L203E, L203C, L203T, L203M, L203A, L203Y, N207G, N207A, L211G, L211M, L211C, L211T, L211V, L211A, W215Y, T217V, T217A, T217I, T217P, T217C, T217Q, T217M, T217F, T217D, T217K, G219S, G219A, G219C, G219H, G219Q, Q235C, Q235N, Q235H, Q235G, Q235W, Q235Y, Q235A, Q235T, Q235E, Q235M, Q235F, Q238C, Q238M, Q238H, Q238V, Q238L, Q238T, Q238I, R242Q, K246I, K253V, M258V, F261L, S263K, C271S, N303C, N303R, N303G, N303A, N303D, N303S, N303H, N303E, N303R, N303K, N303L, N303Q, I312F, I312C, I312A, I312L, I312T, I312V, I312G, I312M, F321H, F321R, F321N, F321Y, F321W, F321D, F321G, F321E, F321M, F321K, F321A, F321Q, V323I, V323L, V323T, V323M, V323A, V324N, V324A, V324C, V324I, V324L, V324T, V324K, V324Y, V324H, V324F, V324S, V324Q, V324M, V324G, A330K, A330V, A330P, A330S, A330C, A330T, A330L, Q333P, Q333T, Q333M, Q333H, Q333S, P337W, P337E, P337H, P337I, P337A, P337M, P337N, P337D, P337K, P337Q, P337G, P337S, P337C, P337L, P337V, F368Y, L373C, L373V, L373I, L373S, L373T, V389I, V389M, V389T, V389L, V389A, R394H, R394K, R394T, R394P, R394M, R394A, Q395P, Q395F, Q395E, Q395C, Q395V, Q395A, Q395H, Q395S, Q395Y, S399N, S399E, S399K, S399H, S399D, S399Y, S399G, S399Q, S399R, S399T, S399A, S399V, S399M, R402Y, R402K, R402D, R402F, R402G, R402N, R402E, R402M, R402S, R402Q, R402T, R402C, R402L, R402V, T403W, T403A, T403V, T403F, T403L, T403Y, T403N, T403G, T403C, T403I, T403S, T403M, T403Q, T403K, T403E, D404I, D404S, D404E, D404N, D404H, D404C, D404M, D404G, D404A, D404Q, D404L, D404P, D404V, D404W, D404F, N408F, N408I, N408A, N408E, N408M, N408S, N408D, N408Y, N408H, N408C, N408Q, N408V, N408W, N408L, N408P, N408K, S409H, S409Y, S409N, S409I, S409D, S409F, S409T, S409C, S409Q, N441F, N441R, N441M, N441G, N441C, N441D, N441L, N441A, N441V, N441W, G448W, G448Y, G448H, G448C, G448T, G448V, G448N, G448Q, E449A, E449P, E449T, E449L, E449H, E449G, E449C, E449I, V469T, V469A, V469H, V469C, V469L, L472K, L472Q, L472M, C473G, C473Q, C473T, C473I, C473M, R484H, R484K, T507R, T507D, T507S, T507G, T507K, T507I, T507M, T507E, T507C, T507L, T507V, G523Q, G523T, G523A, G523M, G523S, G523C, G523I, G523L, I527M, I527V, Y528N, Y528W, Y528M, Y528Q, Y528K, Y528V, Y528I, Y528G, Y528D, Y528A, Y528E, Y528R, Y543C, Y543W, Y543I, Y543M, Y543Q, Y543A, Y543R, Y543H, E549K, E549C, E549I, E549Q, E549A, E549H, E549C, E549M, E549S, E549F, E549L, K550R, K550M, K550Q, S556G, S556V, S556I, P557W, P557T, P557S, P557A, P557Q, P557K, P557D, P557G, P557N, P557L, P557V, H559K, H559S, H559C, H559I, H559W, V560F, V560P, V560I, V560H, V560Y, V560K, N561P, N561Q, N561G, N561A, V562Y, V562I, V562S, V562M, V567I, V567H, V567N, S583M, E601V, E601F, E601Q, E601W, E605R, E605W, E605K, E605M, E605P, E605Y, E605C, E605H, E605A, E605Q, E605S, E605V, E605I, E605G, D607V, D607Y, D607C, D607N, D607W, D607T, D607A, D607H, D607Q, D607E, D607L, D607K, D607G, S609R, S609W, S609H, S609V, S609Q, S609G, S609T, S609K, S609N, S609Y, L610T, L610I, L610K, L610G, L610A, L610W, L610D, L610Q, L610S, L610F or L610N.

Another exemplary piggyBac-like transposon for modifying the genome of a cell is a piggyBat transposon which comprises an ITR with the sequence of SEQ ID NO:107, a heterologous nucleic acid to be transposed and a second ITR with the sequence of SEQ ID NO:108. The transposon may further be flanked by a copy of the tetranucleotide 5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:109 on one side of the heterologous nucleic acid, preferably the left side, and a sequence immediately adjacent to the ITR and proximal to the heterologous nucleic acid that is at least 95% or 100% identical to SEQ ID NO:110 on the other side of the heterologous nucleic acid, preferably the right side. This transposon may be transposed by a corresponding piggyBat transposase comprising a sequence at least 90% or 100% identical to SEQ ID NO:111. Preferably the transposase is a hyperactive variant of a naturally occurring transposase. Preferably the hyperactive variant transposase comprises one or more of the following amino acid changes, relative to the sequence of SEQ ID NO:111: A14V, D475G, P491Q, A561T, T546T, T300A, T294A, A520T, G239S, S5P, S8F, S54N, D9N, D9G, I345V. M481V, E11G, K130T, G9G, R427H, S8P, S36G, D1OG, S36G.

Another exemplary piggyBac-like transposon for modifying the genome of a cell comprises an ITR with the sequence of SEQ ID NO:112, a heterologous nucleic acid to be transposed and a second ITR with the sequence of SEQ ID NO:113. The transposon may further be flanked by a copy of the tetranucleotide 5'-TTAA-3' on each side, immediately adjacent to the ITRs and distal to the heterologous nucleic acid. The transposon may further comprise a sequence immediately adjacent to the ITR and proximal to the heterologous nucleic acid that is at least 95% or 100% identical to SEQ ID NO:114 on one side of the heterologous nucleic acid, preferably the left side, and a sequence immediately adjacent to the ITR and proximal to the heterologous nucleic acid that is at least 95% or 100% identical to SEQ ID NO:115 on the other side of the heterologous nucleic acid preferably the right side. This transposon may be transposed by a corresponding piggyBac transposase comprising a sequence at least 90% or 100% identical to SEQ ID NO:116. Preferably the transposase is a hyperactive variant of a naturally occurring transposase. Preferably the hyperactive variant transposase comprises one or more of the following amino acid changes, relative to the sequence of SEQ ID NO:116: G2C, Q40R, I30V, G1655, T43A, S61R, S103P, S103T, M194V, R281G, M282V, G316E, I426V, Q497L, N505D, Q573L, S509G, N570S, N538K, Q591P, Q591R, F594L, M194V, I30V, S103P, G165S, M282V, S509G, N538K, N571S, C41T, A1424G, C1472A, G1681A, T150C, A351G, A279G, T1638C, A898G, A880G, G1558A, A687G, G715A, T13C, C23T, G161A, G25A, T1050C, A1356G, A26G, A1033G, A1441G, A32G, A389C, A32G, A389C, A32G, T1572A, G456A, T1641C, TI 155C, G1280A, T22C, A106G, A29G, C137T, A14V, D475G, P491Q, A561T, T546T, T300A, T294A, A520T, G239S, SSP, SBF, S54N, D9N, D9G, I345V, M481V, E11G, K130T, G9G, R427H, S8P, S36G, DI0G, S36G, A51T, C153A, C277T, G201A, G202A, T236A, A103T, A104C, T140C, G138T, T118A, C74T, A179C, S3N, I30V, A46S, A46T, I82W, S103P, R119P, C125A, C125L, G165S, Y177K, Y177H, F180L, F180I, F180V, M185L, A187G, F200W, V207P, V209F, M226F, L235R, V240K, F241L, P243K, N258S, M282Q, L296W, L296Y, L296F, M298V, M298A, M298L, P311V, P311I, R315K, T319G, Y327R, Y328V, C340G, C340L, D421H, V436I, M456Y, L470F, S486K, M503I, M503L, V552K, A570T, Q591P, Q591R, R65A, R65E, R95A, R95E, R97A, R97E, R135A, R135E, R161A, R161E, R192A, R192E, R208A, R208E, K176A, K176E, K195A, K195E, S171E, M14V, D270N, I30V, G165S, M282L, M282I, M282V or M282A.

Another example of a piggyBac-like transposon for modifying the genome of a cell is an *Amyelois* transposon comprising an ITR with the sequence of SEQ ID NO:117, a heterologous nucleic acid, and a second ITR with the sequence of SEQ ID NO:118. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:119 on one side of the heterologous nucleic acid, and a sequence that is at least 95% or 100% identical to SEQ ID NO:120 on the other side of the heterologous nucleic acid. This transposon may be transposed by a corresponding *Amyelois* transposase comprising a sequence at least 90% identical to SEQ ID NO:121. Preferably the transposase is a hyperactive variant of a naturally occurring transposase. Preferably the hyperactive variant transposase comprises one or more of the following amino acid changes, relative to the sequence of SEQ ID NO:121: P65E, P65D, R95S, R95T, V100I, V100L, V100M, L115D, L115E, E116P, H121Q, H121N, K139E, K139D, T159N, T159Q, V166F, V166Y, V166W, G179N, G179Q, W187F, W187Y, P198R, P198K, L203R, L203K, I209L, I209V, I209M, N211R, N211K, E238D, L273I, L273V, L273M, D304K, D304R, I323L, I323M, I323V, Q329G, Q329R, Q329K, T345L, T345I, T345V, T345M, K362R, T366R, T366K, T380S, L408M, L408I, L408V, E413S, E413T, S416E, S416D, I426M, I426L, I426V, S435G, L458M, L458I, L458V, A472S, A472T, V475I, V475L, V475M, N483K, N483R, I491M, I491V, I491L, A529P, K540R, S560K, S560R, T562K, T562R, S563K, S563R.

Another exemplary piggyBac-like transposon for modifying the genome of a cell is a *Heliothis* transposon comprising an ITR with the sequence of SEQ ID NO:122, a heterologous nucleic acid and a second ITR with the sequence of SEQ ID NO:123. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:124 on one side of the heterologous nucleic acid, and a sequence that is at least 95% or 100% identical to SEQ ID NO: 125 on the other side of the heterologous nucleic acid. This transposon may be transposed by a corresponding *Heliothis* transposase comprising a sequence at least 90% or 100% identical to SEQ ID NO:126. Preferably the transposase is a hyperactive variant of a naturally occurring transposase. Preferably the hyperactive variant transposase comprises one or more of the following amino acid changes, relative to the sequence of SEQ ID NO:126: S41V, 5411, S41L, L43S, L43T, V81E, V81D, D83S, D83T, V85L, V851, V85M, P125S, P125T, Q126S, Q126T, Q131R, Q131K, Q131T, Q131S, S136V, S136I, S136L, S136M, E140C, E140A, N151Q, K169E, K169D, N212S, I239L, I239V, I239M, H241N, H241Q, T268D, T268E, T297C, M300R, M300K, M305N, M305Q, L312I, C316A, C316M, L321V, L321M, N322T, N322S, P351G, H357R, H357K, H357D, H357E, K360Q, K360N, E379P, K397S, K397T, Y421F, Y421W, V450I, V450L, V450M, Y495F, Y495W, A447N, A447D, A449S, A449V, K476L, V492A, I500M, L585K and T595K.

An advantageous piggyBac-like transposon for modifying the genome of a cultured mammalian cell is an Oryzias transposon comprising an ITR with the sequence of SEQ ID NO:127, a heterologous nucleic acid and a second ITR with the sequence of SEQ ID NO:128. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:129 on one side of the heterologous nucleic acid, and a sequence that is at least 95% or 100% identical to SEQ ID NO:130 on the other side of the heterologous nucleic acid. This transposon may be transposed by a corresponding Oryzias transposase comprising a sequence at least 90% or 100% identical to SEQ ID NO:131. Preferably the transposase is a hyperactive variant of a naturally occurring transposase. Preferably the hyperactive variant transposase comprises one or more of the following amino acid changes, relative to the sequence of SEQ ID NO:131: E22D, A124C, Q131D, Q131E, L138V, L138I, L138M, D160E, Y164F, Y164W, I167L, I167V, I167M, T202R, T202K, I206L, I206V, I206M, I210L, I210V, I210M, N214D, N214E, V253I, V253L, V253M, V258L, V258I, V258M, A284L, A284I, A284M, A284V, V386I, V386M, V386L, M400L, M400I, M400V, S408E, S408D, L409I, L409V, L409M, V458L, V458M, V458I, V467I, V467M, V467L, L468I, L468V, L468M, A514R, A514K, V515I, V515M, V515L, R548K, D549K, D549R, D550R, D550K, S551K and S551R Another exemplary piggyBac-like transposon for modifying the genome of a cell is an *Agrotis* transposon comprising an ITR with the sequence of SEQ ID NO:132, a heterologous nucleic acid, and a second ITR with the sequence of SEQ ID NO:133. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:134 on one side of the heterologous nucleic acid, and a sequence that is at least 95% or 100% identical to SEQ ID NO:135 on the other side of the heterologous nucleic acid. This transposon may be transposed by a corresponding *Agrotis* transposase comprising a sequence at least 90% or 100% identical to SEQ ID NO:136. Preferably the transposase is a hyperactive variant of a naturally occurring transposase.

Another piggyBac-like transposon for modifying the genome of a cell is a *Helicoverpa* transposon comprising an ITR with the sequence of SEQ ID NO:137, a heterologous nucleic acid and a second ITR with the sequence of SEQ ID NO:138. The transposon may further be flanked by a copy of the tetranucleotide 5'-TTAA-3' on each side, immediately adjacent to the ITRs and distal to the heterologous nucleic acid. The transposon may further comprise a sequence that is at least 95% or 100% identical to SEQ ID NO:139 on one side of the heterologous nucleic acid, and a sequence that is at least 95% or 100% identical to SEQ ID NO:140 on the other side of the heterologous nucleic acid. This transposon may be transposed by a corresponding *Helicoverpa* transposase comprising a sequence at least 90% or 100% identical to SEQ ID NO:141. Preferably the transposase is a hyperactive variant of a naturally occurring transposase.

Another exemplary transposon for modifying the genome of cell is a Sleeping Beauty transposon from the Mariner family of transposons, for example one that comprises an ITR with the sequence of SEQ ID NO:142, a heterologous nucleic acid and a second ITR with the sequence of SEQ ID NO:143. Such a transposon can comprise a first transposon end with at least 90% or 100% sequence identity to SEQ ID NO:144, and a second transposon end with at least 90% or 100% sequence identity to SEQ ID NO:145. This transposon may be transposed by a corresponding Sleeping Beauty transposase comprising a sequence at least 90% or 100% identical to SEQ ID NO:146, including hyperactive variants thereof.

Another example transposon for modifying the genome of a mammalian cell is a TcBuster transposon, from the hAT family of transposons, for example one that comprises an ITR with the sequence of SEQ ID NO:147, a heterologous nucleic acid and a second ITR with the sequence of SEQ ID NO:148. Such a transposon can comprise a first transposon end with at least 90% or 100% sequence identity to SEQ ID NO:149, and a second transposon end with at least 90% or 100% sequence identity to SEQ ID NO:150. This transposon may be transposed by a corresponding TcBuster transposase comprising a sequence at least 90% or 100% identical to SEQ ID NO:151, including hyperactive variants thereof.

VII. Cells and Transgenic Animals

Nucleic acids comprising one or more transcriptional units as further described herein and gene transfer systems including the nucleic acids can be introduced into various cells and transgenic non-human animals. Cells into which nucleic acids are introduced are sometimes referred to as host cells or target cells or target host cells. Cells can be prokaryotic or eukaryotic. Mammalian cells, such as human, primate, or rodent are preferred. Insect cells can also be used. Cells can be a cell line of substantially identical cells obtained by expansion of a single cell or a mixed population of cells. Cells can be an immortal cell line or cells of finite life span. Some exemplary cell lines include CHO cell lines, various COS cell lines, HeLa cells, COS cells, 293 cells, U20S, HEK293 cells, L cells, and non-antibody-producing myelomas including Sp2/0 and NS0. Examples of cell types include hepatocytes, neural cells, muscle cells, blood cells, lymphocytes (B cells, natural killer cells and T cells), embryonic stem cells, somatic stem cells, hematopoietic cells, embryos, zygotes and sperm cells (some of which are open to be manipulated in an in vitro setting). Cells can be totipotent (i.e., a cell whose descendants can become any cell type in an organism, e.g., embryonic stem cells), pluripotent (cells whose descendants can differentiate into several restricted cell types, such as hematopoietic stem cells or other stem cells). Nucleic acid introduced into cells can also be used to generate transgenic nonhuman animals, e.g., rodents, such as mice, rats and rabbits, insects, fish, farm animals, such as goats, sheep, pigs, and cattle and non-human primates. Such transgenic animals typically incorporate an introduced heterologous nucleic acid into the genome of their germline and other cells. Such cells and transgenic animals can be used for production of proteins, e.g., therapeutic proteins or enzymes. Cells and transgenic animals can also be used for analyzing phenotypes conferred by expressed proteins, e.g., disease-associated phenotypes, and screening compounds for activity against such disease. Introduced nucleic acids can also be used to modify expression of genes of cells and transgenic animals, as for example, when the introduced nucleic acid encodes an inhibitor RNA to suppress expression of an endogenous gene. Suitable cells into which a nucleic acid has been introduced, particularly stem cells, can also be used for gene therapy. In some such application, the introduced nucleic acid includes a coding segment under inducible control, such that the coding segment encodes a polypeptide, which when expressed is lethal to the cell. Such a system allows an introduced cell to be eliminated by supplying an inducer of expression should the cell start undergoing inappropriate growth (e.g., becoming cancerous). After introduction of transcriptional units into cells, cells can be cultured and tetracycline or an analog be introduced into the culture medium to turn on or off expression of a coding segment. Likewise animals into which transcriptional units have been introduced can be contacted with tetracycline or an analog when a developmental stage is reached at which induction or suppression of expression of the coding segment on the first transcriptional unit is desired. Contacting can be by any conventional route including intravenous, intraperitoneal, subcutaneous, oral, transdermal, and intramuscular. Nucleic acid encoding one or more transcriptional units as described below can also be used in a coupled in vitro transcription and translation systems kits for which are commercially available from e.g., Thermo Fisher Scientific or New England Biolabs.

VIII. Inducible Systems

The invention provides several systems for placing a coding segment of interest under inducible control depending on the presence or absence of tetracycline, doxycycline or other analog. Such systems typically include two transcriptional units, one for expressing a coding segment of interest, the other for expressing a tet-repressor or modified tet-repressor to make expression of the first transcriptional unit dependent on the presence or absence of tetracycline or an analog thereof.

One expression system has a first transcriptional unit including in operable linkage and in order from 5' to 3', a promoter, one or more tet-operator sites, and a coding segment to be expressed. An exemplary transcriptional unit is shown in FIG. 2, which includes a promoter with a TATA box, and adjacent segment ending at a position upstream from the transcriptional start site, first and second tet-operators separated by a spacer, and a coding segment encoding a 5' UTR and an open reading frame to be expressed. The second tet-operator can be immediately adjacent to the first nucleotide of the 5' UTR as shown. When the first and second tet-operators replace a segment of the promoter immediately upstream from the transcription initiation site, transcription may initiate downstream of the remaining promoter within the first or second tet-operator or the 5' UTR. As shown, the promoter includes DNA between the TATA box and a position upstream of the promoter's normal transcriptional start site (the first transcribed nucleotide). It is preferred that the first tet operator sequence replaces a contiguous segment of the promoter including at least the first base pair upstream of the transcriptional start site. More preferably the first tet operator sequence replaces a contiguous segment of 1, 2, 3, 4, 5, 6, 7, 8, 9, 10, 11, 12, 13, 14 or 15 bp 5' of the promoter starting at the nucleotide immediately upstream of the transcriptional start site. Most preferably the first tet operator sequence replaces at least 6-bp 5' of the promoter starting at the nucleotide immediately upstream of the transcriptional start site. A preferred 5' UTR comprises the *Xenopus* globin UTR (SEQ ID NO:29).

Figure 3:
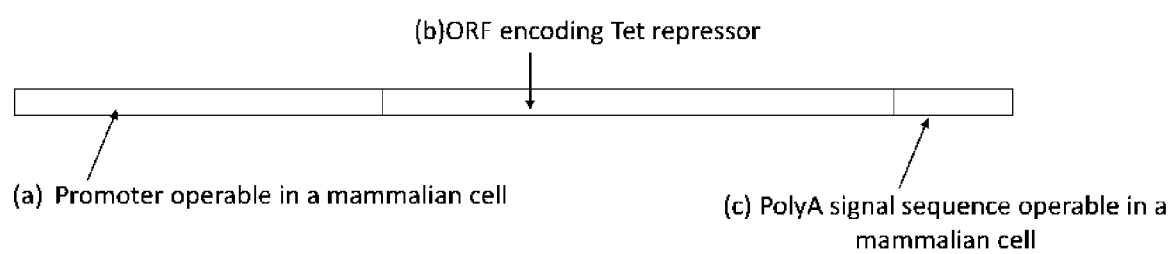

A second transcriptional unit includes a promoter operably linked to a segment encoding a tet-repressor. An exemplary transcriptional unit is shown in FIG. 3. In the system shown a promoter operable in a mammalian cell is operably linked to a coding segment including an open reading frame encoding a tet-repressor followed by a segment encoding a polyA tail. In the absence of tetracycline, doxycycline or other analog, expressed tet-repressor binds to the operator sites in the first transcriptional unit, hindering initiation of transcription and thereby inhibiting or eliminating expression of the coding segment. In the presence of tetracycline, doxycycline or other analog, the tet-repressor binds to the tetracycline or analog, inhibiting or eliminating binding of the tet-repressor to tet-operator(s) in the first transcriptional unit and removing inhibition of the coding segment. Thus, the coding segment is expressed in the presence of tetracycline or analog and not in the absence or at least expression in the presence is much greater than in the absence (e.g., by a factor of at least 2, 5, 10, 20, 50 or 100).

The invention further provides several systems for placing a coding segment of interest under inducible control depending on the presence or absence of cumate or other analog. Such systems typically include two transcriptional units, one for expressing a coding segment of interest, the other for expressing a cumate repressor or modified cumate repressor to make expression of the first transcriptional unit dependent on the presence or absence of cumate or an analog thereof.

Figure 5:
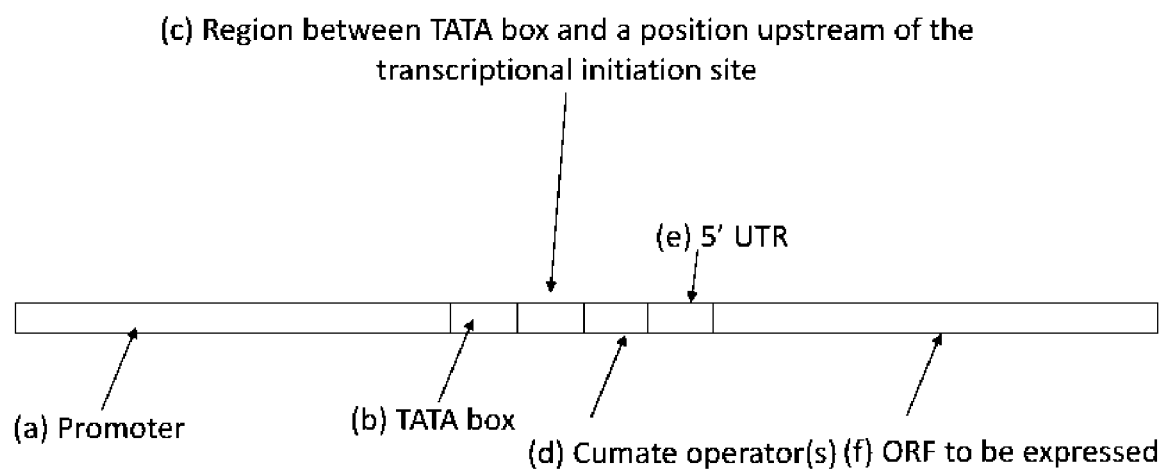
FIGS. 5 and 6 show first and second transcriptional units respectively for a system for cumate-inducible expression of an open reading frame ("cumate-off").

One expression system has a first transcriptional unit including in operable linkage and in order from 5' to 3', a promoter, one or more cumate operators, and a coding segment to be expressed. An exemplary transcriptional unit is shown in FIG. 5, which includes a promoter with a TATA box at least one cumate operator a coding segment encoding a 5' UTR and an open reading frame to be expressed. When the cumate operator(s) replace a segment of the promoter immediately upstream from the transcription initiation site, transcription may initiate downstream of the remaining promoter within the first or second cumate operator or the 5' UTR. Sequence of exemplary promoter-cumate operator fusions are provided as SEQ ID NOS:161-163. A preferred 5' UTR comprises the *Xenopus* globin UTR (SEQ ID NO:29).

Figure 6:
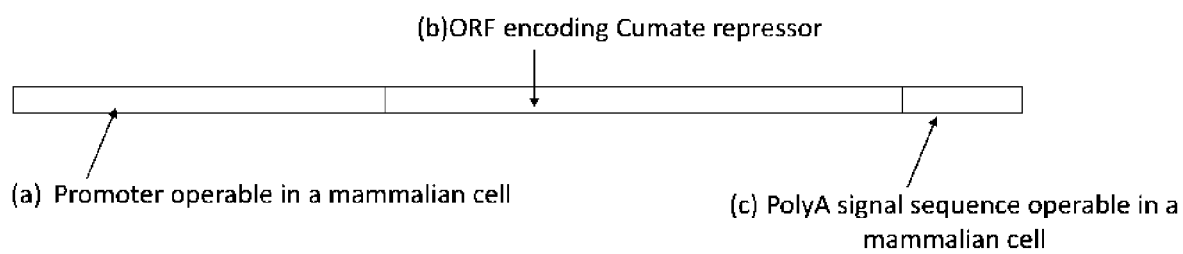

A second transcriptional unit includes a promoter operably linked to a segment encoding a cumate repressor. An exemplary transcriptional unit is shown in FIG. 6. In the system shown a promoter operable in a mammalian cell is operably linked to a coding segment including an open reading frame encoding a cumate repressor followed by a segment encoding a polyA tail. In the absence of cumate or other analog, expressed cumate repressor binds to the operator sites in the first transcriptional unit, hindering initiation of transcription and thereby inhibiting or eliminating expression of the coding segment. In the presence of cumate or analog, the cumate-repressor binds to the cumate or analog, inhibiting or eliminating binding of the cumate repressor to cumate operator(s) in the first transcriptional unit and removing inhibition of the coding segment. Thus, the coding segment is expressed in the presence of cumate or analog and not in the absence or at least expression in the presence is much greater than in the absence (e.g., by a factor of at least 2, 5, 10, 20, 50 or 100).

The promoter of the first transcriptional unit (tet and cumate systems) is preferably a strong promoter to increase expression of the coding sequence after induction. The promoter is preferably a chimeric mouse-human CMV promoter as described above. Such a promoter is a preferred promoter to a human CMV promoter, which has been used for tetracycline-inducible expression previously. This is because elimination of one or more CpG sites from the human CMV promoter reduces the silencing effects of CpG methylation.

The promoter for the second transcriptional unit (tet and cumate systems) is preferably a promoter of reduced strength compared with the chimeric mouse-human CMV promoter described above or even with the human CMV promoter used in some conventional systems. Use of a reduced strength promoter reduces the expression of the tet repressor and thus allows induction of expression from the first transcriptional unit at lower levels of tetracycline or analog than when the same or similar strength promoters are used for both transcriptional units.

The first and second transcriptional units of this system (tet and cumate systems) are preferably combined on the same contiguous nucleic acid for introduction into cells. The nucleic acid can then be part of a transposon or other vector or gene delivery system as described above. Incorporating both transcriptional units on the same nucleic acid facilitates introduction of both units into cells because only one transfection and identification of transformed cells is necessary, but also contributes to cells integrating the same number of copies of each of the transcriptional units. The presence of equal numbers of both transcriptional units allows reproducible control of the ratio of tet-repressor to the number of copies of the first transcriptional unit. This reproducible control, preferably in combination with appropriate promoter selection as described above, can result in any of high levels of inducible expression, greater differentiation between levels of expression in presence and absence of inducer and inducible expression using lower levels of inducer.

Figure 4:
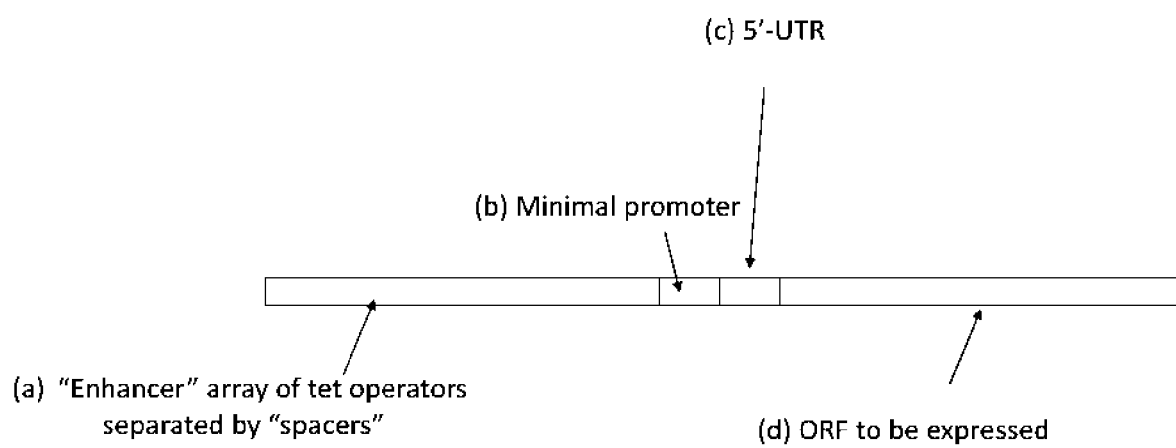
FIG. 4 shows a first transcriptional unit of a different system for tet-inducible expression of an open reading frame ("tet-on" }.

A second tet system for inducible expression has a first transcriptional unit comprising in operable linkage and in order from 5' to 3', one or more tet-operators, a minimal promoter and a coding segment to be expressed. FIG. 4 shows an exemplary form of this transcriptional unit with an array of tet-operators separated by spacers upstream of a minimal promoter, operably linked to a coding segment encoding a 5' UTR and open reading frame to be expressed. The 5' UTR preferably comprises *Xenopus* globin UTR of SEQ ID NO:29. Preferably 2-10 or 3-8, e.g., 2, 3, 4, 5, 6, 7, 9, or 10 operators are present in the array separated by spacers of 10-25 bp, optionally 15-20 bp. A second transcriptional unit includes in operable linkage a promoter and a segment encoding either a tet-repressor or a modified tet-repressor fused to a transcriptional activation domain, such as VP16. When the tet-repressor fused to the transcriptional activation domain is expressed from the second transcriptional unit, it binds to the array of tet-operators in the absence of tetracycline or analog. The transcriptional activation domain recruits polymerase and other transcription factors resulting in transcription from the minimal promoter and expression of the coding segment. In the presence of tetracycline or analog, the tet-repressor can no longer bind the tet-operator array or does so to a much-reduced extent, inhibiting or eliminating expression of the coding segment. Thus, the coding segment is placed under tetracycline or analog inducible control being expressed in the absence of tetracycline or analog.

The reverse form of induction occurs when the tet-repressor is replaced with a modified form of tet-repressor, which binds to tet-operators in the presence of tetracycline or analog. Here, in the absence of tetracycline or analog, the modified tet-repressor linked to transcriptional activation domain is expressed but does not bind significantly if at all to the tet-operators resulting in little or no recruitment of polymerase and other transcription factors, and little if any expression from the minimal promoter. When tetracycline or analog is supplied, the tetracycline or analog binds to the modified tet-repressor, which in turn binds to the tet-operators. The linked transcriptional activation domain then recruits polymerase and other transcriptional factor resulting in transcription of the coding segment from the minimal promoter. The coding segment is thus placed under inducible control of tetracycline or analog, being expressed in the presence of tetracycline and not expressed or expressed at much lower levels in the absence of tetracycline (e.g., least 2-, 5-, 10-, 20-, 50- or 100-fold increased expression on inductions).

Exemplary tet operator arrays can have a nucleotide sequence selected from SEQ ID NOS:8 and 9. An exemplary minimal human CMV promoter has SEQ ID NO:22. Exemplary 5' UTRs comprising the *Xenopus* globin 5' UTR can have a nucleotide sequence selected from SEQ ID NOS:29, 30 and 31. The exemplary arrays are linked in the order from 5' to 3': tet operator array, minimal human CMV promoter, 5' UTR. Any of the exemplified tet operator arrays, can be used with any exemplified minimal human CMV promoter, and any exemplified 5' UTR in the order specified. An exemplary tet operator array fused to the 5' end of a chimpanzee minimal CMV promoter has a nucleotide sequence SEQ ID NO:26. Preferably the 3' end of the minimal chimpanzee CMV promoter is joined to a 5' UTR comprising the *Xenopus* globin 5' UTR with nucleotide sequence SEQ ID NO:29. An exemplary sequence comprising the minimal chimpanzee CMV promoter joined to a 5' UTR comprising the *Xenopus* globin 5' UTR has nucleotide sequence SEQ ID NO:25. An exemplary sequence comprising a tet operator array fused to the minimal chimpanzee CMV promoter joined to a 5' UTR comprising the *Xenopus* globin 5' UTR has nucleotide sequence SEQ ID NO:27.

Figure 7:
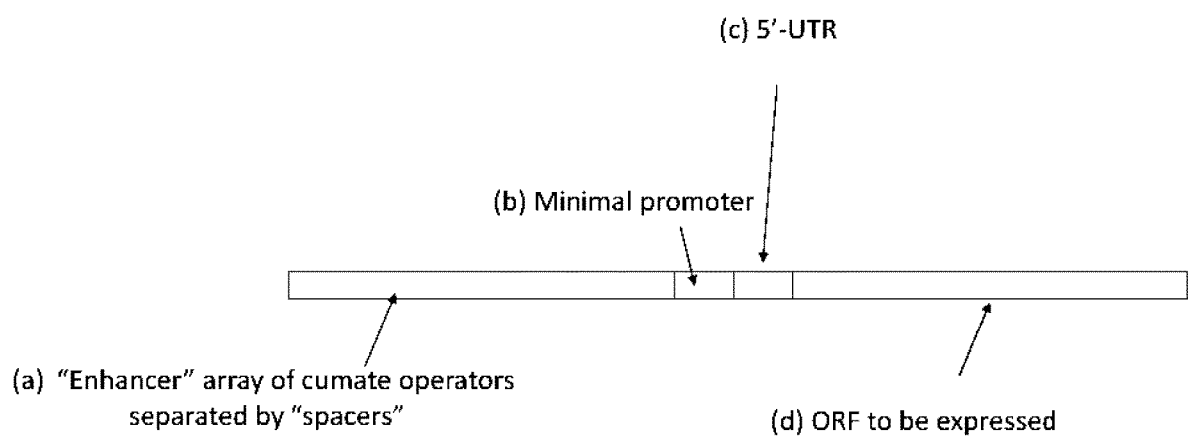
FIG. 7 shows a first transcriptional unit of a different system for cumate-inducible expression of an open reading frame ("cumate on").

A second cumate system for inducible expression has a first transcriptional unit comprising in operable linkage and in order from 5' to 3', one or more cumate-operators, a minimal promoter and a coding segment to be expressed. FIG. 7 shows an exemplary form of this transcriptional unit with an array of cumate operators separated by spacers upstream of a minimal promoter, operably linked to a coding segment encoding a 5' UTR and open reading frame to be expressed. The 5' UTR preferably comprises *Xenopus* globin UTR of SEQ ID NO:29. Preferably 2-10 or 3-8, e.g., 2, 3, 4, 5, 6, 7, 9, or 10 operators are present in the array, optionally separated by spacers of 1-25 bp. A second transcriptional unit includes in operable linkage a promoter and a segment encoding either a cumate repressor or a modified cumate repressor fused to a transcriptional activation domain, such as VP16. When the cumate repressor fused to the transcriptional activation domain is expressed from the second transcriptional unit, it binds to the array of cumate operators in the absence of cumate or analog. The transcriptional activation domain recruits polymerase and other transcription factors resulting in transcription from the minimal promoter and expression of the coding segment. In the presence of cumate or analog, the cumate repressor can no longer bind the cumate operator array or does so to a much-reduced extent, inhibiting or eliminating expression of the coding segment. Thus, the coding segment is placed under cumate or analog inducible control being expressed in the absence of cumate or analog.

The reverse form of induction occurs when the cumate repressor is replaced with a modified form of cumate repressor, which binds to cumate-operators in the presence of cumate or analog. Here, in the absence of cumate or analog, the modified cumate repressor linked to transcriptional activation domain is expressed but does not bind significantly if at all to the cumate operators resulting in little or no recruitment of polymerase and other transcription factors, and little if any expression from the minimal promoter. When cumate or analog is supplied, the cumate or analog binds to the modified cumate repressor, which in turn binds to the cumate operators. The linked transcriptional activation domain then recruits polymerase and other transcriptional factor resulting in transcription of the coding segment from the minimal promoter. The coding segment is thus placed under inducible control of cumate or analog, being expressed in the presence of cumate and not expressed or expressed at much lower levels in the absence of cumate (e.g., least 2-, 5-, 10-, 20-, 50- or 100-fold increased expression on inductions).

Exemplary cumate operator array-promoter fusions are SEQ ID NOS:164-166. Exemplary cumate operator promoter fusions including a 5' UTR are SEQ ID NOS:167-169.

Again (tet and cumate systems), selection of promoters for the first and second transcriptional units and combination of the units into the same contiguous molecule can improve the efficiency and reproducibility of inducible control. As already mentioned, the promoter for the first transcriptional unit is a minimal promoter. A preferred promoter is the minimal chimp CMV promoter described above, which results in higher level expression of a coding segment in the present systems than a minimal human CMV promoter used in conventional systems. The minimal chimp promoter, when activated by binding of a transcriptional activation domain as described above, is more active than a minimal human CMV promoter used in conventional tetracycline-inducible vectors. Preferred promoters for the second transcriptional unit are the intermediate strength promoters described above, although other promoters can also be used. Again, incorporation of both transcriptional units on the same nucleic acid for introduction into cells is advantageous for obtaining a cell that has integrated both transcription units and coordinating expression of the second transcriptional unit with the number of copies of the first transcriptional unit to be regulated. This reproducible control preferably in combination with appropriate promoter selection as described above can result in any of high levels of inducible expression, greater differentiation between levels of expression in presence and absence of inducer and inducible expression using lower levels of inducer.

IX EXAMPLES

1. Inducible Promoters Comprising Tet Binding Sites Between the Promoter and Transcription Start Site in Transiently Transfected HEK Cells.

We tested several embodiments of tet-inducible promoters for their ability to respond to increasing concentrations of doxycycline after transient transfection into (human) HEK 293 cells. Two promoters were constructed in which the 12 bp to the 5' of the transcriptional start site were removed and replaced by a pair of tet operators with nucleotide sequence SEQ ID NO:2. The first promoter was constructed by modification of the human CMV promoter with nucleotide sequence SEQ ID NO:14. Removal of the 12 bp to the 5' of the transcriptional start site produced nucleotide sequence SEQ ID NO:36. Addition of 2× tet operators to this truncated promoter produced nucleotide sequence SEQ ID NO:15. The second promoter constructed by modification of a chimeric murine-human CMV promoter comprising the first 161 bp of the murine CMV promoter with nucleotide sequence SEQ ID NO:16 fused to the last 127 bp of the human CMV promoter with nucleotide sequence SEQ ID NO:13: the junction between the two promoters comprised a 12 bp sequence common to both: 5'-ACGTCAATGGGA-3' (SEQ ID NO:173), and the sequence of the resulting chimeric promoter had nucleotide sequence SEQ ID NO:12. Removal of the 12 bp to the 5' of the transcriptional start site produced nucleotide sequence SEQ ID NO:10. Addition of 2× tet operators to this truncated promoter produced nucleotide sequence SEQ ID NO:11.

The 3' end of the second tet operator in each of the two promoters described above, was fused to a 5' UTR with nucleotide sequence SEQ ID NO:31, which comprised a *Xenopus* globin 5'UTR modified to include a Kozak sequence (the modified *Xenopus* globin 5'UTR has nucleotide sequence SEQ ID NO:29). The UTR was fused to an open reading frame encoding Dasher GFP with amino acid sequence of SEQ ID NO:32, such that transcription from the promoter would result in expression of the GFP.

Each of the two different tet-inducible promoter-GFP transcriptional units was cloned onto a plasmid comprising a second transcriptional unit. The second transcriptional unit comprised an open reading frame encoding a tet repressor with amino acid sequence of SEQ ID NO:5. The open reading frame encoding the repressor was linked to a promoter operable in mammalian cells. Promoters selected were a PGK promoter with nucleotide sequence SEQ ID NO:18, an EEF2 promoter with nucleotide sequence SEQ ID NO:17, a murine CMV promoter with nucleotide sequence SEQ ID NO:16, and a human CMV promoter with nucleotide sequence SEQ ID NO:13.

HEK293 suspension cells were grown in flasks in Expi293 media at 37° C. with 8% CO2, in an incubator with 25 mm throw at 125 RPM. The cells were passaged at a density of 2.5×106 cells/ml 24 hours prior to transfection. Cells were diluted to 3×106 cells/ml, and 700 ul were aliquoted into 96 deep well plates. Each DNA construct was transfected three independent times using ExpiFectamine™ 293 Transfection Reagent at a 1:2.7 DNA:Transfection reagent ratio. After transfection, the cells were placed in an incubator at 37° C. with 8% CO2, with a 3 mm throw shaking at 1,000 RPM. 24 hours post-transfection, the cultures were fed with ExpiFectamine™ 293 Transfection Enhancer 1 and ExpiFectamine™ 293 Transfection Enhancer 2. After this feeding, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 1.

Row 6 of Table 1 shows the behavior of a construct in which the human CMV promoter was modified by addition of tet operators to serve as the inducible promoter, and where the human CMV promoter was also used as the promoter from which the tet repressor was transcribed. Expression from this construct was induced only at the highest concentration of doxycycline tested (100 ng/ml). Similar performance was observed when the human-murine chimeric CMV promoter was modified by addition of tet operators to serve as the inducible promoter, and where the murine CMV promoter was also used as the promoter from which the tet repressor was transcribed (Table 1 row 5), except that the maximum inducible expression was about twice as high as obtained using the human CMV promoter. When weaker promoters EEF2 or PGK were used to drive expression of the tet repressor, induction of expression was seen at lower levels of doxycycline (rows 4 and 3 respectively). This shows that the threshold for doxycycline induction of expression can be modulated by choice of promoter used to express the tet repressor: weaker promoters express lower levels of tet repressor, so less doxycycline is required to bind to the tet repressor to prevent repressor binding to the operators and remove the block to transcriptional initiation.

2. Inducible Promoters Comprising Tet Binding Sites Between the Promoter and Transcription Start Site in Transiently Transfected CHO-S Cells.

We tested several embodiments of tet-inducible promoters for their ability to respond to increasing concentrations of doxycycline after transient transfection into CHO cells. The same DNA constructs were used as described in Example 1.

CHO-s cells were grown in flasks in ExpiCHO media at 37° C. with 5% CO2, in an incubator with 25 mm throw at 125 RPM. The cells were passaged at a density of 4.5×10⁶ cells/ml 24 hours prior to transfection. Cells were diluted to 6×10⁶ cells/ml, and 800 ul were aliquoted into 96 deep well plates. Each DNA construct was transfected three independent times using ExpiFectamine™ CHO Transfection Reagent at a 1:4 DNA:Transfection reagent ratio. After transfection, the cells were placed in an incubator at 37° C. with 5% CO2, with a 3 mm throw shaking at 1,000 RPM. 24 hours post-transfection, the cultures were fed with ExpiFectamine™ CHO Enhancer and ExpiCHO Feed. After feeding the cells, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 2.

Table 2 shows a similar pattern to inducible expression in transient HEK cells, except that the human and murine CMV constructs shown in rows 5 and 6 have reversed places. Expression from the construct in which the murine CMV promoter was used as the promoter from which the tet repressor was transcribed (Table 2 row 5) was induced only at the higher concentrations of doxycycline tested (a little at 30 ng/ml, more at 100 ng/ml). In contrast, higher expression at lower doxycycline concentrations was observed when the human CMV promoter was used as the promoter from which the tet repressor was transcribed (Table 2 row 6). This is consistent with the murine CMV promoter being stronger than the human CMV promoter in rodent cells and the human CMV promoter being stronger than the murine CMV promoter human cells. Again, when weaker promoters EEF2 or PGK were used to drive expression of the tet repressor, induction of expression was seen at lower levels of doxycycline (rows 4 and 3 respectively). Inducible expression was higher from the chimeric human murine CMV promoter than from the human CMV promoter. Again the threshold for doxycycline induction of expression can be modulated by choice of promoter used to express the tet repressor: weaker promoters express lower levels of tet repressor, so less doxycycline is required to bind to the tet repressor to prevent repressor binding to the operators and remove the block to transcriptional initiation.

3. Inducible Promoters Comprising Tet Binding Sites Between the Promoter and Transcription Start Site in Stably Transfected CHO-K1 Cells.

We tested several embodiments of tet-inducible promoters for their ability to respond to increasing concentrations of doxycycline when stably integrated into CHO-K1 cells. DNA constructs were used as described in Example 1. Each construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA'3' target integration sequence, immediately followed by a first ITR with nucleotide sequence SEQ ID NO:41 immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures for each selected cell pool were then grown in EX-CELL™ Advanced™ CHO Fed-batch Medium media at 37° C. with 5% CO2, in an incubator with 25 mm throw at 120 RPM. The cells were passaged at a density of 2×10⁶ cells/ml 24 hours prior to induction. Cells were diluted to 6×10⁶ cells/ml, and 800 ul were aliquoted into 96 deep well plates. Cultures were induced by the addition doxycycline at either 10, 30, 100, 300, 1000 or 3000 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24 and 48 hours post-induction. The average fluorescence at 525 nm for each set of 3 replicates was divided by optical density at 600 nm for each set of 3 replicates to provide an average measure of fluorescence normalized by cell number. Results are shown in Table 3.

Table 3 shows a similar pattern to inducible expression in transiently transfected CHO cells, except that the overall induction levels were substantially lower. Lowest inducible expression was seen where the tet repressor was transcribed from the very active human or murine CMV promoters (Table 3 rows 5 and 6). The constructs in which tet repressor was transcribed from the more weakly active promoters showed expression that was induced at lower levels of doxycycline (expression started at 30 ng/ml when the tet repressor was transcribed from EEF2 or PGK promoters, while 300 ng/ml doxycycline) and reached 1.7-fold higher levels at high concentrations of doxycycline than constructs where the tet repressor was transcribed from a CMV promoter.

4. Inducible Promoters Comprising Tet Binding Sites Between the Promoter and Transcription Start Site in Stably Transfected CHO-K1 Cells.

We tested several embodiments of tet-inducible promoters for their ability to respond to increasing concentrations of doxycycline when stably integrated into CHO-K1 cells. DNA transposon constructs were similar to those described in Example 3, except that additional versions were made with other promoters driving expression of the tet repressor. Transposon compositions are indicated in Table 4.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures of each stably selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ml, and 800 ul were aliquoted into 96 deep well plates. Cultures were induced by the addition doxycycline at either 10, 30, 100, 300 or 1000 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24 and 48 hours post-induction. The average fluorescence at 525 nm for each set of 3 replicates was divided by optical density at 600 nm for each set of 3 replicates to provide an average measure of fluorescence normalized by cell number. Results are shown in Table 4.

Table 4 shows a similar pattern to the inducible expression in stably transfected CHO cells shown in Table 3. Most notably, two constructs whose inducible expression is shown in Table 4 differed only in the 6 nucleotides preceding the tet repressor open reading frame (Table 4 rows 6 and 7). The construct shown in row 6 had an optimal Kozak sequence (5'-GCCGCCACC-3'), while the construct shown in row 7 had a de-optimized Kozak (5'-GCCT11TTT-3'). The de-optimized Kozak results in reduced translational initiation and thus in less tet repressor being present. The consequence of this was that this inducible promoter was induced at only 10 ng/ml doxycycline, and was fully induced at 30 ng/ml doxycycline, whereas the otherwise identical construct with the optimal Kozak initiating translation of the tet repressor did not begin induction until 100 ng/ml doxycycline, and only became fully induced by 1,000 ng/ml doxycycline.

Tables 1, 2, 3 and 4 show that expression levels obtained from tet-inducible promoters, and the amount of inducer required to induce expression, differ depending on the level of expression of the tet repressor. The benefit of combining the transcriptional unit expressing the tet repressor onto the same transposon as the inducible transcriptional unit, is that it minimizes the potential variation in relative expression of tet repressor compared with the number of copies of the inducible promoter in the cell. This improves the predictability of the performance of the system.

5. Inducible Promoters Comprising Tet Binding Sites 5' of the Promoter in Transiently Transfected HEK 293 Cells.

We tested several embodiments of tet-inducible promoters for their ability to respond to increasing concentrations of doxycycline after transient transfection into HEK 293 cells.

Three different minimal CMV promoters, from human, mouse and chimpanzee CMV (with nucleotide sequences SEQ ID NO:22, 23 and 24 respectively) were each fused, at their 5' ends, to an array of 8 tet operators with nucleotide sequence SEQ ID NO:3, to create 3 tet-inducible promoters. The 3' end of each minimal promoter was fused to a 5'UTR with nucleotide sequence SEQ ID NO:30. A control inducible promoter was also constructed by fusing a previously described array of 7 tet operators with nucleotide sequence SEQ ID NO:4 to the 5' end of a previously described modified minimal human CMV promoter with nucleotide sequence SEQ ID NO:38. The 3' end of this control minimal promoter was fused to a 5'UTR with nucleotide sequence SEQ ID NO:39. The 3' end of each 5'UTR was fused to an open reading frame encoding Dasher GFP with amino acid sequence SEQ ID NO:32.

Each of the different tet-inducible promoter-GFP transcriptional units was cloned onto a plasmid comprising a second transcriptional unit. The second transcriptional unit comprised an open reading frame encoding a transcriptional activator comprising a modified tet repressor with amino acid sequence of SEQ ID NO:6, fused to a VP16 transcriptional activator with amino acid sequence SEQ ID NO:7. In addition the control tet-inducible promoter GFP transcriptional unit was cloned onto a plasmid comprising a second transcriptional unit comprising an open reading frame encoding a transcriptional activator comprising a modified tet repressor with amino acid sequence of SEQ ID NO:6, fused to an alternative VP16 transcriptional activator with amino acid sequence SEQ ID NO:40. In each case the open reading frame encoding the transcriptional activator was linked to an SV40 promoter with nucleotide sequence SEQ ID NO:28, which promoter is operable in mammalian cells.

HEK293 suspension cells were grown in flasks in Expi293 media at 37° C. with 8% CO2, in an incubator with 25 mm throw at 125 RPM. The cells were passaged at a density of 2.5×106 cells/ml 24 hours prior to transfection. Cells were diluted to 3×106 cells/ml, and 700 ul were aliquoted into 96 deep well plates. Each DNA construct was transfected three independent times using ExpiFectamine™ 293 Transfection Reagent at a 1:2.7 DNA:Transfection reagent ratio. After transfection, the cells were placed in an incubator at 37° C. with 8% CO2, with a 3 mm throw shaking at 1,000 RPM. 24 hours post-transfection, the cultures were fed with ExpiFectamine™ 293 Transfection Enhancer 1 and ExpiFectamine™ 293 Transfection Enhancer 2. After this feeding, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 5.

Table 5 (rows 4 and 5) shows that the control tet-inducible minimal human CMV promoter resulted in similar induction profiles using either of the different transcriptional activators (with amino acid sequences SEQ ID NOS:8 and 9, which comprise the VP16-derived activation domains with amino acid sequences SEQ ID NOS:7 and 40 respectively). Table 5 also shows that the array of 8 tet operators joined to minimal human CMV promoter with nucleotide sequence SEQ ID NO:22 performs very comparably to the control tet-inducible minimal human CMV promoter (compare Table 5 row 6 with row 5). The minimal murine CMV promoter showed substantially lower levels of induced gene expression than the human minimal CMV promoter sequences (Table 5 row 7). However the inducible promoter comprising the chimpanzee minimal CMV promoter resulted in consistently higher levels of expression than any of the other inducible promoters (Table 5 row 8).

Thus a tet operator array fused to the 5' end of a chimpanzee minimal CMV promoter with nucleotide sequence SEQ ID NO:24 produces a highly effective tet-inducible promoter.

6. Inducible Promoters Comprising Tet Binding Sites 5' of the Promoter in Transiently Transfected CHO-S Cells.

We tested several embodiments of tet-inducible promoters for their ability to respond to increasing concentrations of doxycycline after transient transfection into CHO-S cells.

Constructs were as described in Example 5. CHO-s cells were grown in flasks in ExpiCHO media at 37° C. with 5% CO2, in an incubator with 25 mm throw at 125 RPM. The cells were passaged at a density of 4.5×106 cells/ml 24 hours prior to transfection. Cells were diluted to 6×106 cells/ml, and 800 ul were aliquoted into 96 deep well plates. Each DNA construct was transfected three independent times using ExpiFectamine™ CHO Transfection Reagent at a 1:4 DNA:Transfection reagent ratio. After transfection, the cells were placed in an incubator at 37° C. with 5% CO2, with a 3 mm throw shaking at 1,000 RPM. 24 hours post-transfection, the cultures were fed with ExpiFectamine™ CHO Enhancer and ExpiCHO Feed. After feeding the cells, the cultures were induced by the addition doxycycline at either 10, 30, or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48, and 72 hours post-induction. The average fluorescence at 525 nm for each set of 3 replicates was divided by optical density at 600 nm for each set of 3 replicates to provide an average measure of fluorescence normalized by cell number. Results are shown in Table 6.

Table 6 shows that the tet-inducible promoters performed similarly in transiently transfected CHO cells as they did in transiently transfected HEK 293 cells. The inducible promoter comprising the chimpanzee minimal CMV promoter resulted in consistently higher levels of expression than any of the other inducible promoters (Table 6 row 8). 7. Inducible promoters comprising tet binding sites 5' of the promoter in stably transfected CHO-K1 cells.

We tested several embodiments of tet-inducible promoters for their ability to respond to increasing concentrations of doxycycline after stable integration into CHO-K1 cells.

DNA constructs were used as described in Example 5. Each construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA'3' target integration sequence, immediately followed by a first ITR with nucleotide sequence SEQ ID NO:41, immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures for each selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ml, and 800 ul were aliquoted into 96 deep well plates. Cultures were induced by the addition doxycycline at either 10, 30 or 100 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24 and 48 hours post-induction. The average fluorescence at 525 nm for each set of 3 replicates was divided by optical density at 600 nm for each set of 3 replicates to provide an average measure of fluorescence normalized by cell number. Results are shown in Table 7. Table 7 shows that the minimal chimpanzee CMV tet-inducible promoter shows very good inducible expression when stably integrated into the genome of a host cell. 8. Inducible promoters comprising different numbers of tet binding sites 5' of the promoter in stably transfected CHO-K1 cells.

We tested three embodiments of tet-inducible promoters with different numbers of tet operators for their ability to respond to increasing concentrations of doxycycline after stable integration into CHO-K1 cells.

A minimal CMV promoter from chimpanzee CMV (with nucleotide sequence SEQ ID NO:24) was fused at its 5' end, to an array of 3, 6 or 8 tet operators (with nucleotide sequences SEQ ID NOs: 153, 152 and 3 respectively), to create 3 tet-inducible promoters. The 3' end of each minimal promoter was fused to a 5'UTR with nucleotide sequence SEQ ID NO:30. The 3' end of each 5'UTR was fused to an open reading frame encoding Dasher GFP with amino acid sequence SEQ ID NO:32.

Each of the different tet-inducible promoter-GFP transcriptional units was cloned onto a plasmid comprising a second transcriptional unit. The second transcriptional unit comprised an open reading frame encoding a transcriptional activator comprising a modified tet repressor with amino acid sequence of SEQ ID NO:6, fused to a VP16 transcriptional activator with amino acid sequence SEQ ID NO:7. In each case the open reading frame encoding the transcriptional activator was linked to an SV40 promoter with nucleotide sequence SEQ ID NO:28, which promoter is operable in mammalian cells. Each construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA'3' target integration sequence, immediately followed by a first ITR with nucleotide sequence SEQ ID NO:41, immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Three cultures for each selected cell pool were then grown in EX-CELL® Advanced™ CHO Fed-batch Medium media at 37° C. with 5% CO2, in an incubator with 25 mm throw at 120 RPM. The cells were passaged at a density of 2×106 cells/ml 24 hours prior to induction. Cells were diluted to 6×106 cells/ml, and 800 ul were aliquoted into 96 deep well plates. Cultures were induced by the addition doxycycline at either 10, 30, 100 or 300 ng/ml, with a control to which no doxycycline was added. After doxycycline addition, 100 ul of culture was taken and diluted with 100 ul of PBS. Expression was measured using a SpectroMax M2. OD600 was measured in a flat-bottom, clear-well plate. Green fluorescent protein expression was measured in a black-well plate, with excitation at 485 nm and emission at 525 nm. Sampling was repeated 24, 48 and 72 hours post-induction. The average fluorescence at 525 nm for each set of 3 replicates was divided by optical density at 600 nm for each set of 3 replicates to provide an average measure of fluorescence normalized by cell number. Results are shown in Table 8. Table 8 shows that the minimal chimpanzee CMV tet-inducible promoter, operably linked to 3, 6 or 8 repeats of the tet operator, shows very good inducible expression when stably integrated into the genome of a host cell. It also shows that a smaller number of repeats resulted in a higher level of expression in the absence of doxycycline (compare Table 8 columns B, G, L and Q for row 3 with 8 tet operator repeats, row 4 with 6 tet operator repeats, and row 5 with 3 tet operator repeats. As a control, Table 8 row 6 shows the average fluorescence in cells with no integrated inducible transposon). 9. A hybrid human-mouse CMV promoter is advantageous for expression in stably transfected mammalian cells.

We tested a hybrid human-mouse promoter comprising a segment of a mouse CMV promoter of SEQ ID NO:16 upstream from a segment of a human CMV promoter of SEQ ID NO:13, wherein the hybrid promoter lacks a CG motif at positions corresponding to positions 42 and 43 of SEQ ID NO:13. The junction between contiguous segments is within the sequence ACGTCAATGGGA (SEQ ID NO:173), which is common to the mouse and human CMV promoter sequences. The promoter has nucleotide sequence SEQ ID NO: 12, which comprises SEQ ID NO: 10 plus 13 bases (5'-GTTTAGTGAACCG-3') (SEQ ID NO:176) immediately 5' of the transcriptional start site.

The hybrid promoter was operably linked to an open reading frame encoding an antibody heavy chain with amino acid sequence SEQ ID NO: 154. The construct further comprised a mouse CMV promoter with nucleotide sequence SEQ ID NO: 16 operably linked to an open reading frame with amino acid sequence SEQ ID NO: 155. The construct further comprised a third transcriptional unit expressing glutamine synthetase. The three transcriptional units were flanked by a pair of insulators: an HS4 insulator on one side and a D4Z4 core insulator on the other side. The three transcriptional units and the insulators were all placed into a *Xenopus* piggyBac-like transposon. On one side of the transposon was a 5'-TTAA'3' target integration sequence, immediately followed by a first ITR with nucleotide sequence SEQ ID NO:41, immediately followed by a left transposon end with nucleotide sequence SEQ ID NO:44. On the other side of the transposon was a right transposon end with nucleotide sequence SEQ ID NO:45, immediately followed by a second ITR with nucleotide sequence SEQ ID NO:42, immediately followed by a 5'-TTAA'3' target integration sequence.

Two additional transposon constructs were prepared, in which the hybrid promoter operably linked to the antibody heavy chain was replaced by either a murine CMV promoter with nucleotide sequence SEQ ID NO: 16, or by a human CMV promoter with nucleotide sequence SEQ ID NO: 13.

Transposons were co-transfected with mRNA encoding transposase with amino acid sequence SEQ ID NO:54 into a CHO cell line with no functional glutamine synthetase gene. Cells were grown in the absence of glutamine added to the media until their viability reached 95%. Recovered pools were then grown in a 7-day fed-batch using Sigma Advanced Fed Batch media. Antibody titers were measured in culture supernatant using an Octet. Table 9 shows the titers measured at day 7, and the specific productivities (calculated as the amount of antibody produced per cell per day).

As shown in Table 9, the volumetric (Table 9 column D) and specific (Table 9 column C) productivities obtained using the hybrid promoter with nucleotide sequence comprising SEQ ID NO: 10 operably linked to the heavy chain open reading frame (Table 9 row 1) were higher than those obtained using either of the promoters from which the hybrid promoter was derived (Table 9 rows 2 and 3). We conclude that the hybrid human/murine CMV promoter comprising SEQ ID NO: 10 is advantageous for expression of heterologous proteins in CHO cells.

X TABLES DESCRIPTION

Table 1. DNA constructs comprising two transcriptional units were prepared as described in Example 3. Each construct comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each construct further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. Each construct was transfected into HEK 293 cells in 3 independent transfections, induced with doxycycline and cell numbers and fluorescence were measured as described in Example 1. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to U. Days post-induction are shown in row 1, doxycycline concentrations are shown in row 2.

Table 2. DNA constructs comprising two transcriptional units were prepared as described in Example 1. Each construct comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each construct further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. Each construct was transfected into CHO-s cells in 3 independent transfections, induced with doxycycline and cell numbers and fluorescence were measured as described in Example 2. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to U. Days post-induction are shown in row 1, doxycycline concentrations are shown in row 2.

Table 3. DNA transposons comprising two transcriptional units were prepared as described in Example 1. Each transposon comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each transposon further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. Transposons were stably transfected into CHO cells and selected, after recovery three separate cultures for each stable cell line were induced with doxycycline and cell numbers and fluorescence were measured as described in Example 3. Fluorescence was measured at 525 nm and cell density was measured as optical density at 600 nm. The average fluorescence at 525 nm for each set of 3 replicates was divided by optical density at 600 nm for each set of 3 replicates to provide an average measure of fluorescence normalized by cell number shown in columns F to Z. Days post-induction are shown in row 1, doxycycline concentrations are shown in row 2.

Table 4. DNA transposons comprising two transcriptional units were prepared as described in Example 4. Each transposon comprised a first transcriptional unit comprising an inducible promoter whose name is given in column A, operably linked to an open reading frame encoding a green fluorescent protein. The SEQ ID NO giving the nucleotide sequence of the inducible promoter, lacking the 12 bp before the transcriptional start site is shown in column B, and the SEQ ID NO giving the nucleotide sequence of the inducible promoter including the pair of tet operators is shown in column C. Each transposon further comprised a second transcriptional unit comprising a constitutive promoter operable in a mammalian cell, operably linked to an open reading frame encoding a tet repressor with amino acid sequence SEQ ID NO:5. This promoter name is shown in column D, and the SEQ ID NO giving the nucleotide sequence of the promoter linked to the tet repressor is shown in column E. The promoter sequences indicated in column E in rows 6 and 7 also include the 5'UTR including the Kozak sequence immediately before the translational initiation site for the tet repressor. Transposons were stably transfected into CHO cells and selected, after recovery three separate cultures for each stable cell line were induced with doxycycline and cell numbers and fluorescence were measured as described in Example 4. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number and is shown in columns F to W. Days post-induction are shown in row 1, doxycycline concentrations are shown in row 2.

Table 5. DNA constructs comprising two transcriptional units were prepared as described in Example 5. Each construct comprised a first transcriptional unit comprising a minimal promoter whose name is given in column A, with nucleotide sequence given by the SEQ ID NO shown in column C. The 5' of the minimal promoter was fused to an array of tet operators with nucleotide sequence given by the SEQ ID NO shown in column B. The 3' of the minimal promoter was fused to a 5' UTR with nucleotide sequence given by the SEQ ID NO shown in column D. The 5'UTR was joined to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Each construct was transfected into HEK 293 cells in 3 independent transfections, induced with doxycycline and cell numbers and fluorescence were measured as described in Example 5. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to U. Days post-induction are shown in row 1, doxycycline concentrations are shown in row 2.

Table 6. DNA constructs comprising two transcriptional units were prepared as described in Example 5. Each construct comprised a first transcriptional unit comprising a minimal promoter whose name is given in column A, with nucleotide sequence given by the SEQ ID NO shown in column C. The 5' of the minimal promoter was fused to an array of tet operators with nucleotide sequence given by the SEQ ID NO shown in column B. The 3' of the minimal promoter was fused to a 5' UTR with nucleotide sequence given by the SEQ ID NO shown in column D. The 5'UTR was joined to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Each construct was transfected into CHO-S cells in 3 independent transfections, induced with doxycycline and cell numbers and fluorescence were measured as described in Example 6. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to Q. Days post-induction are shown in row 1, doxycycline concentrations are shown in row 2.

Table 7. DNA transposons comprising two transcriptional units were prepared as described in Example 7. Each transposon comprised a first transcriptional unit comprising a minimal promoter whose name is given in column A, with nucleotide sequence given by the SEQ ID NO shown in column C. The 5' of the minimal promoter was fused to an array of tet operators with nucleotide sequence given by the SEQ ID NO shown in column B. The 3' of the minimal promoter was fused to a 5' UTR with nucleotide sequence given by the SEQ ID NO shown in column D. The 5'UTR was joined to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Transposons were stably transfected into CHO cells and selected, after recovery three separate cultures for each stable cell line were induced with doxycycline and cell numbers and fluorescence were measured as described in Example 7. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns F to Q. Days post-induction are shown in row 1, doxycycline concentrations are shown in row 2.

Table 8. DNA transposons comprising two transcriptional units were prepared as described in Example 8. Each transposon comprised a first transcriptional unit comprising a minimal chimpanzee promoter whose 5' end was fused to an array of tet operators with nucleotide sequence given by the SEQ ID NO shown in column A. The promoter was operably linked to an open reading frame encoding Dasher GFP, with amino acid sequence SEQ ID NO:32. Each construct further comprised a second transcriptional unit comprising a constitutive SV40 promoter operable in a mammalian cell, operably linked to an open reading frame encoding a modified tet repressor fused to a VP16 transcriptional activation domain, the amino acid sequence of the open reading frame given by the SEQ ID NO in column E. Transposons were stably transfected into CHO cells and selected, after recovery three separate cultures for each stable cell line were induced with doxycycline and cell numbers and fluorescence were measured as described in Example 8. Fluorescence was measured at 525 nm and cell density was measured as optical density at 600 nm, with each condition measured for 3 independent transfections. The average fluorescence at 525 nm for each set of 3 replicates was divided by optical density at 600 nm for each set of 3 replicates to provide an average measure of fluorescence normalized by cell number, shown in columns B to U. Days post-induction are shown in row 1, doxycycline concentrations are shown in row 2. Control cells with no integrated transposon are shown in row 6.

Table 9. DNA transposons comprising two transcriptional units were prepared as described in Example 9. Each transposon comprised a first transcriptional unit comprising a mouse CMV promoter operably linked to an open reading frame encoding an antibody light chain. Each transposon further comprised a second transcriptional unit comprising a promoter named in column A and with nucleotide given by the SEQ ID NO in column B, operably linked to an open reading frame encoding an antibody heavy chain. Transposons were stably transfected into CHO cells and selected as described in Example 9. The specific productivity of each CHO cell pool is shown in column C, the volumetric productivity is shown in column D.

TABLE 1

| | A inducible promoter name | B inducible promoter SEQ ID (excluding the operators) | C inducible promoter SEQ ID (including the operators) | D repressor promoter name | E repressor promoter SEQ ID | F | G | H GFP Fluorescence | I |
|---|---|---|---|---|---|---|---|---|---|
| 1 | day | | | | | 0 | 0 | 0 | 0 |
| 2 | dox concentration ng/ml | | | | | 0 | 10 | 30 | 100 |
| 3 | CMV Mm/Hs | 10 | 11 | PGK | 18 | 945 | 903 | 875 | 1,124 |
| 4 | CMV Mm/Hs | 10 | 11 | EEF2 | 17 | 835 | 963 | 903 | 944 |
| 5 | CMV Mm/Hs | 10 | 11 | CMV(Mm) | 16 | 752 | 875 | 877 | 936 |
| 6 | CMV(Hs) | 36 | 15 | CMV(Hs) | 13 | 689 | 659 | 650 | 786 |

| | J | K GFP Fluorescence | L | M | N | O GFP Fluorescence | P | Q | R | S GFP Fluorescence | T | U |
|---|---|---|---|---|---|---|---|---|---|---|---|---|
| 1 | day | 1 | 1 | 1 | 1 | 2 | 2 | 2 | 2 | 3 | 3 | 3 | 3 |
| 2 | dox concentration ng/ml | 0 | 10 | 30 | 100 | 0 | 10 | 30 | 100 | 0 | 10 | 30 | 100 |

TABLE 1-continued

| 3 | 849 | 6,482 | 9,699 | 8,401 | 854 | 6,622 | 19,504 | 21,008 | 838 | 7,107 | 19,038 | 22,871 |
| 4 | 662 | 1,491 | 3,831 | 11,368 | 755 | 1,562 | 4,399 | 17,795 | 699 | 1,400 | 4,199 | 16,295 |
| 5 | 723 | 864 | 1,532 | 9,319 | 672 | 880 | 1,632 | 22,690 | 685 | 889 | 1,595 | 21,029 |
| 6 | 557 | 734 | 993 | 12,312 | 510 | 623 | 903 | 11,250 | 517 | 604 | 829 | 11,212 |

TABLE 2

| | A inducible promoter name | B inducible promoter SEQ ID (excluding the operators) | C inducible promoter SEQ ID (including the operators) | D repressor promoter name | E repressor promoter SEQ ID | F | G | H GFP Fluorescence | | I |
|---|---|---|---|---|---|---|---|---|---|---|
| 1 day | | | | | | 0 | 0 | 0 | | 0 |
| 2 dox concentration ng/ml | | | | | | 0 | 10 | 30 | | 100 |
| 3 | CMV Mm/Hs | 10 | 11 | PGK | 18 | 897 | 1042 | 969 | | 1187 |
| 4 | CMV Mm/Hs | 10 | 11 | EEF2 | 17 | 832 | 945 | 998 | | 1096 |
| 5 | CMV Mm/Hs | 10 | 11 | CMV(Mm) | 16 | 654 | 741 | 701 | | 745 |
| 6 | CMV(Hs) | 36 | 15 | CMV(Hs) | 13 | 466 | 456 | 523 | | 487 |

| | J | K | L GFP Fluorescence | M | N | O | P | Q GFP Fluorescence | R | S | T | U GFP Fluorescence |
|---|---|---|---|---|---|---|---|---|---|---|---|---|
| 1 day | 1 | 1 | 1 | 1 | 2 | 2 | 2 | 2 | 3 | 3 | 3 | 3 |
| 2 dox concentration ng/ml | 0 | 10 | 30 | 100 | 0 | 10 | 30 | 100 | 0 | 10 | 30 | 100 |
| 3 | 1198 | 16964 | 16,09 | 17430 | 1341 | 41392 | 41037 | 37035 | 1277 | 54023 | 49654 | 49327 |
| 4 | 1071 | 15698 | 17,35 | 18772 | 1092 | 32485 | 40884 | 41047 | 1015 | 32201 | 54880 | 55860 |
| 5 | 667 | 890 | 2,13 | 13560 | 631 | 863 | 2267 | 16063 | 614 | 789 | 2038 | 14076 |
| 6 | 427 | 6091 | 9,04 | 8985 | 403 | 7373 | 27836 | 27938 | 369 | 6639 | 29770 | 35882 |

TABLE 3

| | A inducible promoter name | B inducible promoter SEQ ID (excluding the operators) | C inducible promoter SEQ ID (including the operators) | D repressor promoter name | E repressor promoter SEQ ID | F | G | H | I GFP Fluorescence | J | K | L |
|---|---|---|---|---|---|---|---|---|---|---|---|---|
| 1 day | | | | | | 0 | 0 | 0 | 0 | 0 | 0 | 0 |
| 2 dox concentration ng/ml | | | | | | 0 | 10 | 30 | 100 | 300 | 1,000 | 3,000 |
| 3 | CMV Mm/Hs | 10 | 11 | PGK | 18 | 932 | 946 | 958 | 936 | 981 | 1,102 | 1,211 |
| 4 | CMV Mm/Hs | 10 | 11 | EEF2 | 17 | 903 | 925 | 916 | 1,048 | 1,138 | 1,126 | 1,183 |
| 5 | CMV Mm/Hs | 10 | 11 | CMV(Mm) | 16 | 923 | 972 | 1,078 | 1,070 | 1,016 | 1,077 | 969 |
| 6 | CMV(Hs) | 36 | 15 | CMV(Hs) | 13 | 943 | 935 | 939 | 1,008 | 1,096 | 1,008 | 1,007 |

| | M | N | O | P GFP Fluorescence | Q | R | S | T | U | V | W | X GFP Fluorescence | Y | Z |
|---|---|---|---|---|---|---|---|---|---|---|---|---|---|---|
| 1 day | 1 | 1 | 1 | 1 | 1 | 1 | 1 | 2 | 2 | 2 | 2 | 2 | 2 | 2 |
| 2 dox concentration ng/ml | 0 | 10 | 30 | 100 | 300 | 1,000 | 3,000 | 0 | 10 | 30 | 100 | 300 | 1,000 | 3,000 |

TABLE 3-continued

| | | | | | | | | | | | | | | |
|---|---|---|---|---|---|---|---|---|---|---|---|---|---|---|
| 3 | 432 | 922 | 3,613 | 3,651 | 4,012 | 3,879 | 3,796 | 234 | 632 | 3,873 | 8,720 | 8,935 | 8,779 | 8,807 |
| 4 | 435 | 593 | 2,271 | 3,957 | 3,806 | 3,922 | 3,873 | 212 | 344 | 1,704 | 8,143 | 8,866 | 8,521 | 8,363 |
| 5 | 423 | 429 | 426 | 452 | 1,425 | 2,304 | 2,393 | 212 | 222 | 222 | 250 | 985 | 4,867 | 4,967 |
| 6 | 448 | 434 | 447 | 665 | 2,633 | 2,971 | 2,894 | 230 | 241 | 254 | 407 | 3,484 | 5,464 | 5,054 |

TABLE 4

| | A inducible promoter name | B inducible promoter SEQ ID (excluding the operators) | C inducible promoter SEQ ID (including the operators) | D repressor promoter name | E repressor promoter SEQ ID | F | G | H | I | J | K |
|---|---|---|---|---|---|---|---|---|---|---|---|
| | | | | | | | | GFP Fluorescence | | | |
| 1 day | | | | | | 0 | 0 | 0 | 0 | 0 | 0 |
| 2 dox concentration ng/ml | | | | | | 0 | 10 | 30 | 100 | 300 | 1,000 |
| 3 | none | 36 | 15 | none | none | 588 | 608 | 593 | 604 | 600 | 670 |
| 4 | CMV (Hs) | 36 | 15 | EEF2_50 (Rn) | 17 | 775 | 865 | 902 | 886 | 863 | 903 |
| 5 | CMV (Hs) | 36 | 15 | GADPH (Hs) | 19 | 794 | 822 | 885 | 808 | 870 | 867 |
| 6 | CMV (Hs) | 36 | 15 | PGK (Hs)_UTR | 37* | 765 | 827 | 842 | 836 | 893 | 949 |
| 7 | CMV (Hs) | 36 | 15 | PGK (Hs) 6T | 21* | 1,226 | 1,305 | 1,372 | 1,324 | 1,444 | 1,313 |

| | L | M | N | O | P | Q | R | S | T | U | V | W |
|---|---|---|---|---|---|---|---|---|---|---|---|---|
| | GFP Fluorescence | | | | | | GFP Fluorescence | | | | | |
| 1 day | 1 | 1 | 1 | 1 | 1 | 1 | 2 | 2 | 2 | 2 | 2 | 2 |
| 2 dox concentration ng/ml | 0 | 10 | 30 | 100 | 300 | 1,000 | 0 | 10 | 30 | 100 | 300 | 1,000 |
| 3 | 303 | 307 | 312 | 330 | 343 | 307 | 234 | 254 | 277 | 289 | 273 | 252 |
| 4 | 379 | 359 | 384 | 535 | 4,536 | 5,029 | 229 | 233 | 242 | 408 | 5,327 | 10,067 |
| 5 | 386 | 351 | 384 | 463 | 4,013 | 5,458 | 243 | 262 | 257 | 331 | 4,078 | 13,379 |
| 6 | 392 | 385 | 422 | 1,733 | 8,857 | 8,473 | 252 | 277 | 311 | 1,373 | 11,539 | 20,350 |
| 7 | 984 | 10,241 | 11,270 | 11,056 | 11,001 | 11,215 | 917 | 13,449 | 22,540 | 23,087 | 23,294 | 23,032 |

TABLE 5

| | A minimal promoter name | B tet operator array SEQ ID | C minimal promoter SEQ ID | D 5'UTR SEQ ID | E activator SEQ ID | F | G | H | I |
|---|---|---|---|---|---|---|---|---|---|
| | | | | | | | GFP Fluorescence | | |
| 1 day | | | | | | 0 | 0 | 0 | 0 |
| 2 dox concentration ng/ml | | | | | | 0 | 10 | 30 | 100 |
| 3 | none | none | none | -na- | none | 327 | 352 | 336 | 356 |
| 4 | CMV (human) | 4 | 38 | 39 | 9 | 319 | 364 | 405 | 385 |
| 5 | CMV (human) | 4 | 38 | 39 | 8 | 347 | 353 | 421 | 381 |
| 6 | CMV (human) | 3 | 22 | 30 | 8 | 340 | 405 | 423 | 438 |
| 7 | CMV (mouse) | 3 | 23 | 30 | 8 | 366 | 372 | 413 | 445 |
| 8 | CMV (chimp) | 3 | 24 | 30 | 8 | 382 | 381 | 455 | 409 |

| | J | K | L | M | N | O | P | Q | R | S | T | U |
|---|---|---|---|---|---|---|---|---|---|---|---|---|
| | GFP Fluorescence | | | | GFP Fluorescence | | | | GFP Fluorescence | | | |
| 1 day | 1 | 1 | 1 | 1 | 2 | 2 | 2 | 2 | 3 | 3 | 3 | 3 |
| 2 dox concentration ng/ml | 0 | 10 | 30 | 100 | 0 | 10 | 30 | 100 | 0 | 10 | 30 | 100 |
| 3 | 181 | 171 | 182 | 162 | 162 | 167 | 170 | 147 | 175 | 161 | 165 | 116 |
| 4 | 207 | 2,941 | 6,311 | 10,235 | 192 | 7,793 | 19,524 | 29,747 | 186 | 7,144 | 14,532 | 29,358 |
| 5 | 227 | 2,868 | 7,021 | 12,696 | 221 | 6,924 | 20,381 | 27,913 | 204 | 7,620 | 23,733 | 31,291 |
| 6 | 227 | 2,832 | 5,125 | 11,810 | 208 | 5,840 | 20,094 | 27,444 | 157 | 8,154 | 24,174 | 33,560 |

TABLE 5-continued

| | | | | | | | | | | | | |
|---|---|---|---|---|---|---|---|---|---|---|---|---|
| 7 | 213 | 1,228 | 2,375 | 3,584 | 187 | 3,096 | 6,866 | 12,462 | 165 | 3,765 | 8,315 | 14,273 |
| 8 | 219 | 5,430 | 10,049 | 14,957 | 191 | 7,203 | 23,939 | 35,555 | 181 | 10,699 | 24,578 | 40,111 |

TABLE 6

| | A<br>minimal<br>promoter<br>name | B<br>tet<br>operator<br>array<br>SEQ ID | C<br>minimal<br>promoter<br>SEQ ID | D<br>5'UTR<br>SEQ ID | E<br>activator<br>SEQ ID | F | G | H | I |
|---|---|---|---|---|---|---|---|---|---|
| | | | | | | \multicolumn{4}{c}{GFP Fluorescence} | | | |
| 1 | day | | | | | 0 | 0 | 0 | 0 |
| 2 | dox concentration ng/ml | | | | | 0 | 10 | 30 | 100 |
| 3 | none | none | none | -na- | none | 299 | 324 | 307 | 338 |
| 4 | CMV (human) | 4 | 38 | 39 | 9 | 321 | 308 | 341 | 377 |
| 5 | CMV (human) | 4 | 38 | 39 | 8 | 330 | 322 | 354 | 339 |
| 6 | CMV (human) | 3 | 22 | 30 | 8 | 328 | 350 | 343 | 347 |
| 7 | CMV (mouse) | 3 | 23 | 30 | 8 | 338 | 338 | 355 | 357 |
| 8 | CMV (chimp) | 3 | 24 | 30 | 8 | 318 | 350 | 343 | 344 |

| | J | K | L | M | N | O | P | Q |
|---|---|---|---|---|---|---|---|---|
| | \multicolumn{4}{c}{GFP Fluorescence} | | \multicolumn{3}{c}{GFP Fluorescence} | | | |
| 1 | day | 1 | 1 | 1 | 1 | 2 | 2 | 2 | 2 |
| 2 | dox concentration ng/ml | 0 | 10 | 30 | 100 | 0 | 10 | 30 | 100 |
| 3 | 279 | 280 | 285 | 332 | 221 | 250 | 248 | 251 |
| 4 | 329 | 3,309 | 4,478 | 6,296 | 284 | 8,452 | 10,291 | 12,820 |
| 5 | 333 | 3,621 | 5,740 | 8,261 | 305 | 8,336 | 13,034 | 15,582 |
| 6 | 315 | 4,160 | 5,731 | 8,761 | 252 | 10,583 | 14,017 | 18,621 |
| 7 | 325 | 2,015 | 2,258 | 2,426 | 297 | 3,432 | 3,997 | 4,214 |
| 8 | 314 | 6,875 | 11,122 | 12,640 | 265 | 14,610 | 22,281 | 25,388 |

TABLE 7

| | A<br>minimal<br>promoter<br>name | B<br>tet<br>operator<br>array<br>SEQ ID | C<br>minimal<br>promoter<br>SEQ ID | D<br>5'UTR<br>SEQ ID | E<br>activator<br>SEQ ID | F | G | H | I |
|---|---|---|---|---|---|---|---|---|---|
| | | | | | | \multicolumn{4}{c}{GFP Fluorescence} | | | |
| 1 | day | | | | | 0 | 0 | 0 | 0 |
| 2 | dox concentration ng/ml | | | | | 0 | 10 | 30 | 100 |
| 3 | CMV (human) | 4 | 38 | 39 | 9 | 680 | 729 | 771 | 769 |
| 4 | CMV (human) | 4 | 38 | 39 | 8 | 747 | 830 | 824 | 841 |
| 5 | CMV (human) | 3 | 22 | 30 | 8 | 696 | 681 | 719 | 772 |
| 6 | CMV (mouse) | 3 | 23 | 30 | 8 | 667 | 647 | 722 | 698 |
| 7 | CMV (chimp) | 3 | 24 | 30 | 8 | 616 | 591 | 651 | 680 |

| | J | K | L | M | N | O | P | Q |
|---|---|---|---|---|---|---|---|---|
| | \multicolumn{4}{c}{GFP Fluorescence} | | \multicolumn{3}{c}{GFP Fluorescence} | | | |
| 1 | day | 1 | 1 | 1 | 1 | 2 | 2 | 2 | 2 |
| 2 | dox concentration ng/ml | 0 | 10 | 30 | 100 | 0 | 10 | 30 | 100 |
| 3 | 518 | 5,741 | 21,530 | 32,702 | 455 | 4,950 | 26,641 | 59,550 |
| 4 | 540 | 5,725 | 25,107 | 37,497 | 441 | 4,473 | 28,432 | 73,749 |
| 5 | 443 | 8,913 | 30,944 | 39,670 | 314 | 7,247 | 34,490 | 76,695 |
| 6 | 479 | 4,009 | 15,993 | 20,063 | 364 | 3,060 | 19,759 | 36,385 |
| 7 | 435 | 9,141 | 27,396 | 31,841 | 304 | 7,046 | 38,680 | 75,416 |

TABLE 8

| | A tet operator array SEQ ID | B | C | D GFP Fluorescence | E | F | G | H | I GFP Fluorescence | J | K |
|---|---|---|---|---|---|---|---|---|---|---|---|
| 1 | day | 0 | 0 | 0 | 0 | 0 | 1 | 1 | 1 | 1 | 1 |
| 2 | dox concentration ng/ml | 0 | 10 | 30 | 100 | 300 | 0 | 10 | 30 | 100 | 300 |
| 3 | 3 | 987 | 1,056 | 1,037 | 1,115 | 1,007 | 587 | 8,625 | 28,451 | 38,463 | 36,978 |
| 4 | 152 | 1,184 | 1,229 | 1,179 | 1,147 | 1,227 | 840 | 13,360 | 41,155 | 43,771 | 45,851 |
| 5 | 153 | 1,851 | 1,772 | 1,690 | 1,947 | 1,735 | 1,371 | 7,789 | 25,179 | 34,587 | 35,641 |
| 6 | C129 none | 873 | 884 | 832 | 963 | 894 | 287 | 288 | 294 | 309 | 289 |

| | | L | M | N GFP Fluorescence | O | P | Q | R | S | T GFP Fluorescence | U |
|---|---|---|---|---|---|---|---|---|---|---|---|
| 1 | day | 2 | 2 | 2 | 2 | 2 | 3 | 3 | 3 | 3 | 3 |
| 2 | dox concentration ng/ml | 0 | 10 | 30 | 100 | 300 | 0 | 10 | 30 | 100 | 300 |
| 3 | | 454 | 6,811 | 37,624 | 69,761 | 84,619 | 383 | 5,801 | 30,114 | 59,567 | 85,327 |
| 4 | | 767 | 11,247 | 43,311 | 83,912 | 94,533 | 714 | 9,075 | 45,019 | 77,306 | 99,674 |
| 5 | | 1,384 | 7,076 | 30,440 | 56,861 | 73,496 | 1,397 | 5,778 | 25,860 | 52,691 | 81,195 |
| 6 | C129 | 202 | 212 | 227 | 218 | 222 | 162 | 160 | 167 | 170 | 171 |

TABLE 9

| | A HC promoter name | B HC promoter SEQ ID NO | C specific productivity (pg/cell/day) | D volumetric productivity (g/L) |
|---|---|---|---|---|
| 1 | hybrid | 12 | 23.00 | 1,617 |
| 2 | human | 13 | 19.30 | 1,491 |
| 3 | murine | 16 | 13.68 | 1,312 |

All publications, patents and patent applications, accession numbers, websites and the like mentioned in this specification are incorporated by reference to the same extent as if each individual publication, patent or patent application was so individually denoted. To the extent different content is associated with an accession number or other reference at different times, the content in effect as of the effective filing date of this application is meant. The effective filing date is the date of the earliest priority application disclosing the accession number in question. Unless otherwise apparent from the context any element, embodiment, step, feature or aspect of the invention can be performed in combination with any other.

What is claimed is:

1. A nucleic acid comprising a transcriptional unit comprising a hybrid mouse-human CMV promoter having a sequence comprising SEQ ID NO:10 in operable linkage with a coding segment.

2. The nucleic acid of claim 1, further comprising at least first and second tet-operators in operable linkage with the promoter and wherein the first and second tet-operators are situated 3' to the promoter, downstream of a TATA box and upstream of the coding segment and its transcription start site.

3. The nucleic acid of claim 2, wherein the promoter and tet-operators together form a sequence consisting of SEQ ID NO:11.

4. The nucleic acid of claim 1, further comprising at least one cumate operator in operable linkage with the promoter and wherein each cumate operator is situated 3' to the promoter, downstream of a TATA box and upstream of the coding segment and its transcription start site.

5. The nucleic acid of claim 4, wherein each cumate operator has a sequence selected independently from any of SEQ ID NOS:156-158.

6. The nucleic acid of claim 1, further comprising a second transcriptional unit comprising a second promoter operably linked to a segment encoding a tet-repressor effective to bind a tet-operator in the absence of tetracycline or doxycycline thereby inhibiting expression of the coding segment, and in the presence of tetracycline or doxycycline, the tet-repressor binds to the tetracycline or doxycycline, which inhibits its binding to the tet-operators, thereby increasing expression of the coding segment.

7. The nucleic acid of claim 6, wherein the second promoter is a weaker promoter than a human CMV promoter.

8. The nucleic acid of claim 6, wherein the second promoter is a eukaryotic translation elongation factor 2 (EEF2) or phosphoglycerate kinase (PGK) promoter.

9. The nucleic acid of claim 6, wherein the second promoter has a sequence selected from any of SEQ ID NOS:17-21, 33 and 34.

10. The nucleic acid of claim 6, wherein the tet-repressor has an amino acid sequence comprising SEQ ID NO:5.

11. The nucleic acid of claim 1, further comprising a second transcriptional unit comprising a second promoter operably linked to a segment encoding a cumate repressor effective to bind a cumate operator in the absence of cumate thereby inhibiting expression of the coding segment, and in the presence of cumate, the cumate repressor binds to the cumate, which inhibits its binding to the cumate operators, thereby increasing expression of the coding segment.

12. The nucleic acid of claim 11, wherein the promoter of the second transcriptional unit is a weaker promoter than a human CMV promoter.

13. The nucleic acid of claim 11, wherein the promoter of the second transcriptional unit is a eukaryotic translation elongation factor 2 (EEF2) or phosphoglycerate kinase (PGK) promoter.

14. The nucleic acid of claim 11, wherein the promoter is selected from any of SEQ ID NOS:17-21, 33 and 34.

15. The nucleic acid of claim 11, wherein the cumate repressor has an amino acid sequence comprising SEQ ID NO:170.

16. The nucleic acid of claim 1, wherein the coding segment encodes a protein.

17. A transposon comprising the nucleic acid of claim 1 flanked by inverted repeats of the transposon such that the nucleic acid is integrated into a cell with a transposase.

18. The transposon of claim 17, which is a piggyBac-like transposon.

19. An isolated cell transformed with the nucleic acid of claim 1.

20. The isolated cell of claim 19, which is mammalian.

21. A non-human animal transformed with the nucleic acid of claim 1.

22. A cultured cell or non-human transgenic animal having a genome comprising the nucleic acid of claim 1.

23. A method for inducible expression of a coding segment, the method comprising, (i) culturing a cell comprising a first transcriptional unit comprising in operable linkage with at least two tet-operators, a hybrid mouse-human CMV promoter having a sequence comprising SEQ ID NO:10 and a coding segment, and a second transcriptional unit comprising in operable linkage a promoter, and a segment encoding a tet-repressor, (a) in the absence of tetracycline, doxycycline, or other tetracycline analog, wherein the tet-repressor is expressed and binds to the at least two tet-operators, thereby inhibiting expression of the coding segment, and (b) in the presence of tetracycline, doxycycline or other tetracycline analog, wherein the tet-repressor binds to the tetracycline, doxycycline or other tetracycline analog, which inhibits its binding to the tet-operators, thereby increasing expression of the coding segment, or (ii) culturing a cell comprising a first transcriptional unit comprising in operable linkage with at least one cumate operator, a hybrid mouse-human CMV promoter having a sequence comprising SEQ ID NO:10, and a coding segment, and a second transcriptional unit comprising in operable linkage a promoter, and a segment encoding a cumate repressor, (a) in the absence of cumate or an analog thereof, wherein the cumate repressor is expressed and binds to the at least one cumate operator, thereby inhibiting expression of the coding segment, and (b) in the presence of cumate or an analog thereof, wherein the cumate repressor binds to the cumate or analog thereof, which inhibits its binding to the cumate operator and expression of the coding segment is increased.

24. The method of claim 23, wherein the first and second transcriptional units are components of the same contiguous DNA molecule.

25. The method of claim 24, further comprising introducing the contiguous DNA molecule into the cell.

26. The method of claim 25, wherein the cell is a mammalian cell, and wherein the first and second transcriptional units integrate into the genome of the cell.

27. The method of claim 23, wherein the first and second transcriptional units are components of a transposon.

28. The method of claim 27, wherein the transposon is a piggyBac-like transposon and wherein the transposon is integrated in the cell with a transposase.

29. A system for inducible expression comprising (i) a first transcriptional unit comprising in operable linkage with at least two tet-operators, a hybrid mouse-human CMV promoter having a sequence comprising SEQ ID NO:10, and a coding segment, and a second transcriptional unit comprising in operable linkage a promoter, and a segment encoding a tet-repressor, wherein the tet-repressor is expressed and binds to the at least two tet-operators in the absence of tetracycline or doxycycline, thereby inhibiting expression of the coding segment, and in the presence of tetracycline or doxycycline, the tet-repressor binds to the tetracycline or doxycycline, which inhibits its binding to the tet-operators, thereby increasing expression of the coding segment, or (ii) a first transcriptional unit comprising in operable linkage with at least one cumate operator, a hybrid mouse-human CMV promoter comprising SEQ ID NO:10, and a coding segment, and a second transcriptional unit comprising in operable linkage a promoter, and a segment encoding a cumate repressor, wherein the cumate repressor is expressed and binds to the at least one cumate operator in the absence of cumate, thereby inhibiting expression of the coding segment, and in the presence of cumate, the cumate repressor binds to the cumate, which inhibits its binding to the cumate operator and expression of the coding segment is increased.

* * * * *

```
                        SEQUENCE LISTING

Sequence total quantity: 176
SEQ ID NO: 1           moltype = DNA  length = 19
FEATURE                Location/Qualifiers
misc_feature           1..19
                       note = Synthetic
source                 1..19
                       mol_type = other DNA
                       organism = synthetic construct
SEQUENCE: 1
tccctatcag tgatagaga                                                 19

SEQ ID NO: 2           moltype = DNA  length = 40
FEATURE                Location/Qualifiers
misc_feature           1..40
                       note = Synthetic
misc_difference        20..21
                       note = n is a, c, g, or t
source                 1..40
                       mol_type = other DNA
                       organism = synthetic construct
SEQUENCE: 2
tccctatcag tgatagagan ntccctatca gtgatagaga                          40

SEQ ID NO: 3           moltype = DNA  length = 283
FEATURE                Location/Qualifiers
misc_feature           1..283
                       note = Synthetic
source                 1..283
                       mol_type = other DNA
                       organism = synthetic construct
```

```
SEQUENCE: 3
tccctatcag tgatagagat gcttctccac tcactatccc tatcagtgat agagagtaaa    60
ctcttcatag gttccctatc agtgatagag agtctagtct gcataccttc cctatcagtg   120
atagagagac aactccttat aggttcccta tcagtgatag agtaaaact ggtcatacct    180
tccctatcag tgatagagag taaactgtag ataccttccc tatcagtgat agagagtaaa   240
ctggatatag gttccctatc agtgatagag aaagcttata cct                     283

SEQ ID NO: 4              moltype = DNA  length = 247
FEATURE                   Location/Qualifiers
misc_feature              1..247
                          note = Synthetic
source                    1..247
                          mol_type = other DNA
                          organism = synthetic construct
SEQUENCE: 4
tccctatcag tgatagagaa cgtatgaaga gtttactccc tatcagtgat agagaacgta    60
tgcagacttt actccctatc agtgatagag aacgtataag gagtttactc cctatcagtg   120
atagagaacg tatgaccagt ttactcccta tcagtgatag agaacgtatc tacagtttac   180
tccctatcag tgatagagaa cgtatatcca gtttactccc tatcagtgat agagaacgta   240
taagctt                                                             247

SEQ ID NO: 5              moltype = AA   length = 207
FEATURE                   Location/Qualifiers
REGION                    1..207
                          note = Synthetic
source                    1..207
                          mol_type = protein
                          organism = synthetic construct
SEQUENCE: 5
MSRLDKSKVI NSALELLNEV GIEGLTTRKL AQKLGVEQPT LYWHVKNKRA LLDALAIEML    60
DRHHTHFCPL EGESWQDFLR NNAKSFRCAL LSHRDGAKVH LGTRPTEKQY ETLENQLAFL   120
CQQGFSLENA LYALSAVGHF TLGCVLEDQE HQVAKEERET PTTDSMPPLL RQAIELFDHQ   180
GAEPAFLFGL ELIICGLEKQ LKCESGS                                       207

SEQ ID NO: 6              moltype = AA   length = 206
FEATURE                   Location/Qualifiers
REGION                    1..206
                          note = Synthetic
source                    1..206
                          mol_type = protein
                          organism = synthetic construct
SEQUENCE: 6
MSRLDKSKVI NSALELLNGV GIEGLTTRKL AQKLGVEQPT LYWHVKNKRA LLDALPIEML    60
DRHHTHSCPL EGESWQDFLR NNAKSYRCAL LSHRDGAKVH LGTRPTEKQY ETLENQLAFL   120
CQQGFSLENA LYALSAVGHF TLGCVLEEQE HQVAKEERET PTTDSMPPLL KQAIELFDRQ   180
GAEPAFLFGL ELIICGLEKQ LKCESG                                        206

SEQ ID NO: 7              moltype = AA   length = 66
FEATURE                   Location/Qualifiers
REGION                    1..66
                          note = Synthetic
source                    1..66
                          mol_type = protein
                          organism = synthetic construct
SEQUENCE: 7
AYSRARTKNN YGSTIEGLLD LPDDDPTDAL DDFDLDMLPA DALDDFDLDM LPADALDDFD    60
LDMLPG                                                               66

SEQ ID NO: 8              moltype = AA   length = 272
FEATURE                   Location/Qualifiers
REGION                    1..272
                          note = Synthetic
source                    1..272
                          mol_type = protein
                          organism = synthetic construct
SEQUENCE: 8
MSRLDKSKVI NSALELLNGV GIEGLTTRKL AQKLGVEQPT LYWHVKNKRA LLDALPIEML    60
DRHHTHSCPL EGESWQDFLR NNAKSYRCAL LSHRDGAKVH LGTRPTEKQY ETLENQLAFL   120
CQQGFSLENA LYALSAVGHF TLGCVLEEQE HQVAKEERET PTTDSMPPLL KQAIELFDRQ   180
GAEPAFLFGL ELIICGLEKQ LKCESGAYSR ARTKNNYGST IEGLLDLPDD DPTDALDDFD   240
LDMLPADALD DFDLDMLPAD ALDDFDLDML PG                                 272

SEQ ID NO: 9              moltype = AA   length = 248
FEATURE                   Location/Qualifiers
REGION                    1..248
                          note = Synthetic
source                    1..248
                          mol_type = protein
                          organism = synthetic construct
```

```
SEQUENCE: 9
MSRLDKSKVI NSALELLNGV GIEGLTTRKL AQKLGVEQPT LYWHVKNKRA LLDALPIEML    60
DRHHTHSCPL EGESWQDFLR NNAKSYRCAL LSHRDGAKVH LGTRPTEKQY ETLENQLAFL   120
CQQGFSLENA LYALSAVGHF TLGCVLEEQE HQVAKEERET PTTDSMPPLL KQAIELFDRQ   180
GAEPAFLFGL ELIICGLEKQ LKCESGGPTD ALDDFDLDML PADALDDFDL DMLPADALDD   240
FDLDMLPG                                                            248

SEQ ID NO: 10             moltype = DNA   length = 275
FEATURE                   Location/Qualifiers
misc_feature              1..275
                          note = Synthetic
source                    1..275
                          mol_type = other DNA
                          organism = synthetic construct
SEQUENCE: 10
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctc                              275

SEQ ID NO: 11             moltype = DNA   length = 315
FEATURE                   Location/Qualifiers
misc_feature              1..315
                          note = Synthetic
source                    1..315
                          mol_type = other DNA
                          organism = synthetic construct
SEQUENCE: 11
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctctccct atcagtgata gagatctccc   300
tatcagtgat agaga                                                    315

SEQ ID NO: 12             moltype = DNA   length = 288
FEATURE                   Location/Qualifiers
misc_feature              1..288
                          note = Synthetic
source                    1..288
                          mol_type = other DNA
                          organism = synthetic construct
SEQUENCE: 12
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatggg agtttgtttt ggcaccaaaa   180
tcaacgggac tttccaaaat gtcgtaataa ccccgccccg ttgacgcaaa tgggcggtag   240
gcgtgtacgg tgggaggtct atataagcag agctcgttta gtgaaccg                288

SEQ ID NO: 13             moltype = DNA   length = 220
FEATURE                   Location/Qualifiers
misc_feature              1..220
                          note = Synthetic
source                    1..220
                          mol_type = other DNA
                          organism = synthetic construct
SEQUENCE: 13
tgctgatgcg gttttggcag tacaccaatg ggcgtggata gcggtttgac tcacggggat    60
ttccaagtct ccaccccatt gacgtcaatg ggagtttgtt ttggcaccaa aatcaacggg   120
actttccaaa atgtcgtaat aaccccgccc cgttgacgca aatgggcggt aggcgtgtac   180
ggtgggaggt ctatataagc agagctcgtt tagtgaaccg                         220

SEQ ID NO: 14             moltype = DNA   length = 220
FEATURE                   Location/Qualifiers
misc_feature              1..220
                          note = Synthetic
source                    1..220
                          mol_type = other DNA
                          organism = synthetic construct
SEQUENCE: 14
tggtgatgcg gttttggcag tacatcaatg ggcgtggata gcggtttgac tcacggggat    60
ttccaagtct ccaccccatt gacgtcaatg ggagtttgtt ttggcaccaa aatcaacggg   120
actttccaaa atgtcgtaac aactccgccc cattgacgca aatgggcggt aggcgtgtac   180
ggtgggaggt ctatataagc agagctcgtt tagtgaaccg                         220

SEQ ID NO: 15             moltype = DNA   length = 247
FEATURE                   Location/Qualifiers
misc_feature              1..247
```

```
                        note = Synthetic
source                  1..247
                        mol_type = other DNA
                        organism = synthetic construct
SEQUENCE: 15
tggtgatgcg gttttggcag tacatcaatg ggcgtggata gcggtttgac tcacggggat    60
ttccaagtct ccaccccatt gacgtcaatg ggagtttgtt ttggcaccaa aatcaacggg   120
actttccaaa atgtcgtaac aactccgccc cattgacgca aatgggcggt aggcgtgtac   180
ggtgggaggt ctatataagc agagctctcc ctatcagtga tagagatctc cctatcagtg   240
atagaga                                                             247

SEQ ID NO: 16           moltype = DNA   length = 286
FEATURE                 Location/Qualifiers
misc_feature            1..286
                        note = Synthetic
source                  1..286
                        mol_type = other DNA
                        organism = synthetic construct
SEQUENCE: 16
agtcattggg tttttccagc caatttataa aacgccatgt actttcccac cattgacgtc    60
aatgggctat tgaaactaat gcaacgtgac ctttaaacgg tactttccca tagctgatta   120
atgggaaagt accgttctcg agccaataca cgtcaatgga aagtgaaagg gcagccaaaa   180
cgtaacaccg ccccggtttt ccctggaaaa ttccatattg gcacgcattc tattggctga   240
gctgcgttct acgtgggtat aagaggcgcg accagcgtcg gtaccg                  286

SEQ ID NO: 17           moltype = DNA   length = 329
FEATURE                 Location/Qualifiers
misc_feature            1..329
                        note = Synthetic
source                  1..329
                        mol_type = other DNA
                        organism = synthetic construct
SEQUENCE: 17
cggtccgaat ttcaaagtct ttttcctatt gacctacaag gttttcaaga atcatgttgt    60
aagcaactgt gttctgagga atctatgttt aaaaacccat ccgtggatct tggcccaggg   120
tccagagact gagctagcca cgccccggcc gcgccgcagc cactcccacg gcagttcaag   180
tgttaagtcc caaagaccgc gctctgtgca tgcgcagacc cgtccacagc tggctcctag   240
ccaacccggc cggacgagca cccggcgccg tcacgtgacg cacccaaccg gcgtcgacct   300
ataaaaggcc gggcgttgac gtcagcgtt                                     329

SEQ ID NO: 18           moltype = DNA   length = 466
FEATURE                 Location/Qualifiers
misc_feature            1..466
                        note = Synthetic
source                  1..466
                        mol_type = other DNA
                        organism = synthetic construct
SEQUENCE: 18
cggggttggg gttgcgcctt ttccaaggca gccctgggtt tgcgcaggga cgcggctgct    60
ctgggcgtgt tccgggaaa cgcagcggcg ccgaccctgg gcctcgcaca ttcttcacgt    120
ccgttcgcag cgtcacccgg atcttcgccc tacccttgtg ggccccccg gcgacgcttc    180
ctcgtccgcc cctaagtcgg gaaggttcct tgcggttcgc ggcgtgccgg acgtgacaaa   240
cggaagccgc acgtctcact agtaccctcg cagacggaca cgccaggga gcaatggcag   300
cgcgccgacc gcgatgggct gtggccaata gcggctgctc agcagggcgc gccgagagca   360
gcggccggga aggggcggtg cgggaggcgg ggtgtgggc ggtagtgtgg gccctgttcc    420
tgcccgcgcg gtgttccgca ttctgcaagc ctccggagcc cacgtc                  466

SEQ ID NO: 19           moltype = DNA   length = 494
FEATURE                 Location/Qualifiers
misc_feature            1..494
                        note = Synthetic
source                  1..494
                        mol_type = other DNA
                        organism = synthetic construct
SEQUENCE: 19
atgacgtcga ggagaagttc cccaactttc ccgcctctca gcctttgaaa gaaagaaagg    60
ggaggggca ggccgcgtgc agccgcgagc ggtgctgggc tccggctcca attcccatc    120
tcagtcgttc ccaaagtcct cctgtttcat ccaagcgtgt aagggtcccc gtccttgact   180
ccctagtgtc ctgctgccca cagtccagtc tgggaacca gcaccgatca cctcccatcg   240
ggccaatctc agtccttcc cccctacgtc ggggcccaca cgctcggtgc gtgcccagtt   300
gaaccaggcg gctgcggaaa aaaaaaagcg gggagaaagt aggcccggc tactagcggt    360
tttacgggcg cacgtagctc aggcctcaag accttgggct gggactggct gagcctggcg   420
ggaggcgggg tccgagtcac cgcctgccgc gcgcccccg gtttctataa attgagcccg   480
cagcctcccg cttc                                                     494

SEQ ID NO: 20           moltype = DNA   length = 80
FEATURE                 Location/Qualifiers
misc_feature            1..80
                        note = Synthetic
```

```
source                        1..80
                              mol_type = other DNA
                              organism = synthetic construct
SEQUENCE: 20
ggccggagga gcacccgcgc cgtcacgtga cgtgcccaac cggcgtcgac ctataaaagg    60
ccgggcgttg acgtcagcgg                                                80

SEQ ID NO: 21                 moltype = DNA   length = 503
FEATURE                       Location/Qualifiers
misc_feature                  1..503
                              note = Synthetic
source                        1..503
                              mol_type = other DNA
                              organism = synthetic construct
SEQUENCE: 21
cggggttggg gttgcgcctt ttccaaggca gccctgggtt tgcgcaggga cgcggctgct    60
ctgggcgtgt ttccgggaaa cgcagcggcg ccgaccctgg gcctcgcaca ttcttcacgt   120
ccgttcgcag cgtcacccgg atcttcgccg ctacccttgt gggcccccg gcgacgcttc   180
ctcgtccgcc cctaagtcgg gaaggttcct tgcggttcgc ggcgtgccgg acgtgacaaa   240
cggaagccgc acgactcact agtaccctcg cagacggaca gcgccaggga gcaatggcag   300
cgcgccgacc gcgatgggct gtggccaata gcggctgctc agcagggcgc gccgagagca   360
gcggccggga aggggcggtg cgggaggcgg ggtgtgggc ggtagtgtgg gccctgttcc   420
tgcccgcgcg gtgttccgca ttctgcaagc ctccggagcg cacgtcctct cagggacac   480
ccaagctgtc tagagccttt ttt                                            503

SEQ ID NO: 22                 moltype = DNA   length = 51
FEATURE                       Location/Qualifiers
misc_feature                  1..51
                              note = Synthetic
source                        1..51
                              mol_type = other DNA
                              organism = synthetic construct
SEQUENCE: 22
taggcgtgta cggtgggagg tctatataag cagagctcgt ttagtgaacc g              51

SEQ ID NO: 23                 moltype = DNA   length = 52
FEATURE                       Location/Qualifiers
misc_feature                  1..52
                              note = Synthetic
source                        1..52
                              mol_type = other DNA
                              organism = synthetic construct
SEQUENCE: 23
ggctgagctg cgttctacgt gggtataaga ggcgcgacca gcgtcggtac cg             52

SEQ ID NO: 24                 moltype = DNA   length = 51
FEATURE                       Location/Qualifiers
misc_feature                  1..51
                              note = Synthetic
source                        1..51
                              mol_type = other DNA
                              organism = synthetic construct
SEQUENCE: 24
taggcgtgcc ctatgggcgg tctatataag cagagcccgt ttagtgaacc g              51

SEQ ID NO: 25                 moltype = DNA   length = 151
FEATURE                       Location/Qualifiers
misc_feature                  1..151
                              note = Synthetic
source                        1..151
                              mol_type = other DNA
                              organism = synthetic construct
SEQUENCE: 25
taggcgtgcc ctatgggcgg tctatataag cagagcccgt ttagtgaacc gtcagatcgc    60
ctggagaggc catccaacgt ctctggggtg agacagcttg cttgttcttt ttgcagaagc   120
tcagaataaa cgctcaactt tggccgccac c                                  151

SEQ ID NO: 26                 moltype = DNA   length = 334
FEATURE                       Location/Qualifiers
misc_feature                  1..334
                              note = Synthetic
source                        1..334
                              mol_type = other DNA
                              organism = synthetic construct
SEQUENCE: 26
tccctatcag tgatagagat gcttctccac tcactatccc tatcagtgat agagagtaaa    60
ctcttcatag gttccctatc agtgatagag agtctagtct gcataccttc cctatcagtg   120
atagagagac aactccttat aggttcccta tcagtgatag agagtaaact ggtcatacct   180
tccctatcag tgatagagag taaactgtag atacctccc tatcagtgat agagagtaaa   240
```

```
ctggatatag gttcccatc agtgatagag aaagcttata ccttaggcgt gccctatggg   300
cggtctatat aagcagagcc cgtttagtga accg                              334

SEQ ID NO: 27              moltype = DNA   length = 434
FEATURE                    Location/Qualifiers
misc_feature               1..434
                           note = Synthetic
source                     1..434
                           mol_type = other DNA
                           organism = synthetic construct
SEQUENCE: 27
tccctatcag tgatagagat gcttctccac tcactatccc tatcagtgat agagagtaaa   60
ctcttcatag gttcccatc agtgatagag agtctagtct gcataccttc cctatcagtg   120
atagagagac aactcctat aggttcccta tcagtgatag agagtaaact ggtcatacct   180
tccctatcag tgatagagag taaactgtag ataccttccc tatcagtgat agagagtaaa   240
ctggatatag gttcccatc agtgatagag aaagcttata ccttaggcgt gccctatggg   300
cggtctatat aagcagagcc cgtttagtga accgtcagat cgcctggaga ggccatccaa   360
cgtctctggg gtgagacagc ttgcttgttc ttttgcaga agctcagaat aaacgctcaa   420
ctttggccgc cacc                                                    434

SEQ ID NO: 28              moltype = DNA   length = 173
FEATURE                    Location/Qualifiers
misc_feature               1..173
                           note = Synthetic
source                     1..173
                           mol_type = other DNA
                           organism = synthetic construct
SEQUENCE: 28
tagtcccgcc cctaactccg cccatcccgc cctaactcc gcccagttcc gcccattctc    60
cgccccatcg ctgactaatt tttttattt atgcagaggc cgaggccgcc tcggcctctg    120
agctattcca gaagtagtga ggaggctttt tggaggcct aggcttttgc aaa           173

SEQ ID NO: 29              moltype = DNA   length = 57
FEATURE                    Location/Qualifiers
misc_feature               1..57
                           note = Synthetic
source                     1..57
                           mol_type = other DNA
                           organism = synthetic construct
SEQUENCE: 29
agcttgcttg ttcttttgc agaagctcag aataaacgct caactttggc cgccacc       57

SEQ ID NO: 30              moltype = DNA   length = 100
FEATURE                    Location/Qualifiers
misc_feature               1..100
                           note = Synthetic
source                     1..100
                           mol_type = other DNA
                           organism = synthetic construct
SEQUENCE: 30
tcagatcgcc tggagaggcc atccaacgtc tctggggtga cacagcttgc ttgttctttt   60
tgcagaagct cagaataaac gctcaacttt ggccgccacc                         100

SEQ ID NO: 31              moltype = DNA   length = 110
FEATURE                    Location/Qualifiers
misc_feature               1..110
                           note = Synthetic
source                     1..110
                           mol_type = other DNA
                           organism = synthetic construct
SEQUENCE: 31
tcgtcgacga gctcgtttag tgaaccgtca gatcgccgtc tctggggtga cacagcttgc   60
ttgttctttt tgcagaagct cagaataaac gctcaacttt ggccgccacc              110

SEQ ID NO: 32              moltype = AA    length = 236
FEATURE                    Location/Qualifiers
REGION                     1..236
                           note = Synthetic
source                     1..236
                           mol_type = protein
                           organism = synthetic construct
SEQUENCE: 32
MTALTEGAKL FEKEIPYITE LEGDVEGMKF IIKGEGTGDA TTGTIKAKYI CTTGDLPVPW    60
ATLVSTLSYG VQCFAKYPSH IKDFFKSAMP EGYTQERTIS FEGDGVYKTR AMVTYERGSI   120
YNRVTLTGEN FKKDGHILRK NVAFQCPPSI LYILPDTVNN GIRVEFNQAY DIEGVTEKLV   180
TKCSQMNRPL AGSAAVHIPR YHHITYHTKL SKDRDERRDH MCLVEVVKAV DLDTYQ       236

SEQ ID NO: 33              moltype = DNA   length = 503
FEATURE                    Location/Qualifiers
```

```
misc_feature          1..503
                      note = Synthetic
source                1..503
                      mol_type = other DNA
                      organism = synthetic construct
SEQUENCE: 33
cggggttggg gttgcgcctt ttccaaggca gccctgggtt tgcgcaggga cgcggctgct    60
ctgggcgtgg ttccgggaaa cgcagcggcg ccgaccctgg gcctcgcaca ttcttcacgt   120
ccgttcgcag cgtcacccgg atcttcgccg ctacccttgt gggcccccg gcgacgcttc    180
ctcgtccgcc cctaagtcgg aaggttcct tgcggttcgc ggcgtgccgg acgtgacaaa    240
cggaagccgc acgactcact agtaccctcg cagacggaca cgccaggga gcaatggcag   300
cgcgccgacc gcgatgggct gtggccaata gcggctgctc agcagggcgc gccgagagca   360
gcggccggga aggggcggtg cgggaggcgg ggtgtggggc ggtagtgtgg gccctgttcc   420
tgcccgcgcg gtgttccgca ttctgcaagc ctccggagcg cacgtcctct caggggacac   480
ccaagctgtc tagagccttc tat                                           503

SEQ ID NO: 34         moltype = DNA  length = 503
FEATURE               Location/Qualifiers
misc_feature          1..503
                      note = Synthetic
source                1..503
                      mol_type = other DNA
                      organism = synthetic construct
SEQUENCE: 34
cggggttggg gttgcgcctt ttccaaggca gccctgggtt tgcgcaggga cgcggctgct    60
ctgggcgtgg ttccgggaaa cgcagcggcg ccgaccctgg gcctcgcaca ttcttcacgt   120
ccgttcgcag cgtcacccgg atcttcgccg ctacccttgt gggcccccg gcgacgcttc    180
ctcgtccgcc cctaagtcgg aaggttcct tgcggttcgc ggcgtgccgg acgtgacaaa    240
cggaagccgc acgactcact agtaccctcg cagacggaca cgccaggga gcaatggcag   300
cgcgccgacc gcgatgggct gtggccaata gcggctgctc agcagggcgc gccgagagca   360
gcggccggga aggggcggtg cgggaggcgg ggtgtggggc ggtagtgtgg gccctgttcc   420
tgcccgcgcg gtgttccgca ttctgcaagc ctccggagcg cacgtcctct caggggacac   480
ccaagctgtc tagagcctcc ttt                                           503

SEQ ID NO: 35         moltype = DNA  length = 13
FEATURE               Location/Qualifiers
misc_feature          1..13
                      note = Synthetic
source                1..13
                      mol_type = other DNA
                      organism = synthetic construct
SEQUENCE: 35
gtttagtgaa ccg                                                       13

SEQ ID NO: 36         moltype = DNA  length = 207
FEATURE               Location/Qualifiers
misc_feature          1..207
                      note = Synthetic
source                1..207
                      mol_type = other DNA
                      organism = synthetic construct
SEQUENCE: 36
tggtgatgcg gttttggcag tacatcaatg ggcgtggata gcggtttgac tcacggggat    60
ttccaagtct ccacccatt gacgtcaatg ggagtttgtt ttggcaccaa aatcaacggg   120
actttccaaa atgtcgtaac aactccgccc cattgacgca aatgggcggt aggcgtgtac   180
ggtgggaggt ctatataagc agagctc                                       207

SEQ ID NO: 37         moltype = DNA  length = 503
FEATURE               Location/Qualifiers
misc_feature          1..503
                      note = Synthetic
source                1..503
                      mol_type = other DNA
                      organism = synthetic construct
SEQUENCE: 37
cggggttggg gttgcgcctt ttccaaggca gccctgggtt tgcgcaggga cgcggctgct    60
ctgggcgtgg ttccgggaaa cgcagcggcg ccgaccctgg gcctcgcaca ttcttcacgt   120
ccgttcgcag cgtcacccgg atcttcgccg ctacccttgt gggcccccg gcgacgcttc    180
ctcgtccgcc cctaagtcgg aaggttcct tgcggttcgc ggcgtgccgg acgtgacaaa    240
cggaagccgc acgtctcact agtaccctcg cagacggaca cgccaggga gcaatggcag   300
cgcgccgacc gcgatgggct gtggccaata gcggctgctc agcagggcgc gccgagagca   360
gcggccggga aggggcggtg cgggaggcgg ggtgtggggc ggtagtgtgg gccctgttcc   420
tgcccgcgcg gtgttccgca ttctgcaagc ctccggagcg cacgtcctct caggggacac   480
ccaagctgtc tagagccgcc acc                                           503

SEQ ID NO: 38         moltype = DNA  length = 50
FEATURE               Location/Qualifiers
misc_feature          1..50
                      note = Synthetic
```

```
                   source          1..50
                                   mol_type = other DNA
                                   organism = synthetic construct
SEQUENCE: 38
taggcgtgta cggtgggcgc ctataaaagc agagctcgtt tagtgaaccg              50

SEQ ID NO: 39                      moltype = DNA   length = 144
FEATURE                            Location/Qualifiers
misc_feature                       1..144
                                   note = Synthetic
source                             1..144
                                   mol_type = other DNA
                                   organism = synthetic construct
SEQUENCE: 39
tcagatcgcc tggagaggcc atccacgctg ttttgacctc catagtggac accgggaccg    60
atccagcctc cgtctctggg gtgagacagc ttgcttgttc ttttttgcaga agctcagaat  120
aaacgctcaa ctttggccgc cacc                                         144

SEQ ID NO: 40                      moltype = AA   length = 42
FEATURE                            Location/Qualifiers
REGION                             1..42
                                   note = Synthetic
source                             1..42
                                   mol_type = protein
                                   organism = synthetic construct
SEQUENCE: 40
GPTDALDDFD LDMLPADALD DFDLDMLPAD ALDDFDLDML PG                      42

SEQ ID NO: 41                      moltype = DNA   length = 14
FEATURE                            Location/Qualifiers
misc_feature                       1..14
                                   note = Synthetic
source                             1..14
                                   mol_type = other DNA
                                   organism = synthetic construct
SEQUENCE: 41
ccytttbmct gcca                                                     14

SEQ ID NO: 42                      moltype = DNA   length = 14
FEATURE                            Location/Qualifiers
misc_feature                       1..14
                                   note = Synthetic
source                             1..14
                                   mol_type = other DNA
                                   organism = synthetic construct
SEQUENCE: 42
tggcagkvaa argg                                                     14

SEQ ID NO: 43                      moltype = DNA   length = 64
FEATURE                            Location/Qualifiers
misc_feature                       1..64
                                   note = Synthetic
source                             1..64
                                   mol_type = other DNA
                                   organism = synthetic construct
SEQUENCE: 43
atcacgcatg ggatacgtcg tggcagtaaa agggcttaaa tgccaacgac gcgtcccata    60
cgtt                                                                64

SEQ ID NO: 44                      moltype = DNA   length = 82
FEATURE                            Location/Qualifiers
misc_feature                       1..82
                                   note = Synthetic
source                             1..82
                                   mol_type = other DNA
                                   organism = synthetic construct
SEQUENCE: 44
atgacgcatg ggatacgtcg tggcagtaaa agggcttaaa tgccaacgac gcgtcccata    60
cgttgttggc attttaagtc tt                                            82

SEQ ID NO: 45                      moltype = DNA   length = 106
FEATURE                            Location/Qualifiers
misc_feature                       1..106
                                   note = Synthetic
source                             1..106
                                   mol_type = other DNA
                                   organism = synthetic construct
SEQUENCE: 45
cctgggtaaa ctaaaagtcc cctcgaggaa aggcccctaa agtgaaacag tgcaaaacgt    60
```

-continued

```
tcaaaaactg tctggcaata caagttccac tttgggacaa atcggc            106

SEQ ID NO: 46          moltype = DNA   length = 105
FEATURE                Location/Qualifiers
misc_feature           1..105
                       note = Synthetic
source                 1..105
                       mol_type = other DNA
                       organism = synthetic construct
SEQUENCE: 46
cctgggtaaa ctaaaagtcc cctcgaggaa aggcccctaa agtgaaacag tgcaaaacgt 60
tcaaaaactg tctggcaata caagttccac tttgaccaaa acggc              105

SEQ ID NO: 47          moltype = AA   length = 589
FEATURE                Location/Qualifiers
REGION                 1..589
                       note = Synthetic
source                 1..589
                       mol_type = protein
                       organism = synthetic construct
SEQUENCE: 47
MAKRFYSAEE AAAHCMASSS EEFSGSDSEY VPPASESDSS TEESWCSSST VSALEEPMEV 60
DEDVDDLEDQ EAGDRADAAA GGEPAWGPPC NFPPEIPPFT TVPGVKVDTS NFEPINFFQL 120
FMTEAILQDM VLYTNVYAEQ YLTQNPLPRY ARAHAWHPTD IAEMKRFVGL TLAMGLIKAN 180
SLESYWDTTT VLSIPVFSAT MSRNRYQLLL RFLHFNNNAT AVPPDQPGHD RLHKLRPLID 240
SLSERFAAVY TPCQNICIDE SLLLFKGRLQ FRQYIPSKRA RYGIKFYKLC ESSSGYTSYF 300
LIYEGKDSKL DPPGCPPDLT VSGKIVWELI SPLLGQGFHL YVDNFYSSIP LFTALYCLDT 360
PACGTINRNR KGLPRALLDK KLNRGETYAL RKNELLAIKF FDKKNVFMLT SIHDESVIRE 420
QRVGRPPKNK PLCSKEYSKY MGGVDRTDQL QHYYNATRKT RAWYKKVGIY LIQMALRNSY 480
IVYKAAVPGP KLSYYKYQLQ ILPALLFGGV EEQTVPEMPP SDNVARLIGK HFIDTLPPTP 540
GKQRPQKGCK VCRKRGIRRD TRYYCPKCPR NPGLCFKPCF EIYHTQLHY            589

SEQ ID NO: 48          moltype = AA   length = 589
FEATURE                Location/Qualifiers
REGION                 1..589
                       note = Synthetic
source                 1..589
                       mol_type = protein
                       organism = synthetic construct
SEQUENCE: 48
MAKRFYSAEE AAAHCMAPSS EEFSGSDSEY VPPASESDSS TEESWCSSST VSALEEPMEV 60
DEDVDDLEDQ EAGDRADAAA GGEPAWGPPC NFPPEIPPFT TVPGVKVDTS NFEPINFFQL 120
FMTEAILQDM VLYTNVYAEQ YLTQNPLPRY ARAHAWHPTD IAEMKRFVGL TLAMGLIKAN 180
SLESYWNTTT VLSIPVFSAT MSRNRYQLLL RFLHFNNNAT AVPPDQPHD RLHKLRPLID 240
SLSERFAAVY TPCQNICIDE SLLLFKGRLR FRQYIPSKRA RYGIKFYKLC ESSSGYTSYF 300
LIYEGKDSKL DPPGCPPDLT VSGKIVWELI SPLLGQGFHL YVDNFYSSIP LFTALYCLDT 360
PACGTINRTR KGLPRALLDK KLNRGETYAL RKNELLAIKF FDKKNVFMLT SIHDESVIRE 420
QRVGRPPKNK PLCSKEYSKY MGGVDRTDQL QHYYNATRKT SAWYKKVGIY LIQMALRNSY 480
IVYKAAVPGP KLSYYKYQLQ ILPALLFGGV EEQTVPEMLP SDNVARLIGK HFIDTLPPTP 540
GKQRPQKGCK VCRKRGIRRD TRYYCPKCPR NPGLCFKPCF EIYHTQLHY            589

SEQ ID NO: 49          moltype = AA   length = 589
FEATURE                Location/Qualifiers
REGION                 1..589
                       note = Synthetic
source                 1..589
                       mol_type = protein
                       organism = synthetic construct
SEQUENCE: 49
MAKRFYSAEE AAAHCMASSS EEFSGSDSEY VPPASESDSS TEESWCSSST VSALEEPMEV 60
DEDVDDLEDQ EAGDRADAAA GGEPAWGPPC NFPPEIPPFT TVPGVKVDTS NYEPINFFQL 120
FMTEAILQDM VLYTNVYAEQ YLTQNPLPRY ARAHAWHPTD IAEMKRFVGL TLAMGLIKAN 180
SLESYWDTTT VLSIPVFSAT MSRNRYQLLL RFLHFNNNAT AVPPDQPGHD RLHKLRPLID 240
SLSERFAAVY TPCQNICIDE SLLLFKGRLQ FRQYIPSKRA RYGIKFYKLC ESSSGYTSYF 300
LIYEGKDSKL DPPGCPPDLT VSGKIVWELI SPLLGQGFHL YVDNFYSSIP LFTALYCLDT 360
PACGTINRNR KGLPRALLDK KLNRGETYAL RKNELLAIKF FDKKNVFMLT SIHDESVIRE 420
QRVGRPPKNK PLCSKEYSKY MGGVDRTDQL QHYYNATRKT RAWYKKVGIY LIQMALRNSY 480
IVYKAAVPGP KLSYYKYQLQ ILPALLFGGV EEQTVPEMPP SDNVARLIGK HFIDTLPPTP 540
GKQRPQKGCK VCRKRGIRRD TRYYCPKCPR NPGLCFKPCF EIYHTQLHY            589

SEQ ID NO: 50          moltype = AA   length = 589
FEATURE                Location/Qualifiers
REGION                 1..589
                       note = Synthetic
source                 1..589
                       mol_type = protein
                       organism = synthetic construct
SEQUENCE: 50
MAKRFYSAEE AAAHCMASSS EEFSGSDSEY VPPASESDSS TEESWCSSST VSALEEPMEV 60
```

```
DEDVDDLEDQ EAGDRADAAA GGEPAWGPPC NFPPEIPPFT TVPGVKVDTS NFEPINFFQL   120
FMTEAILQDM VLYTNVYAEQ YLTQVPLPRY ARAHAWHPTD IAEMKRFVGL TLAMGLIKAN   180
SLESYWDTTT VLNIPVFSAT MSRNRYQLLL RFLEFNNEAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHY              589

SEQ ID NO: 51             moltype = AA  length = 589
FEATURE                   Location/Qualifiers
REGION                    1..589
                          note = Synthetic
source                    1..589
                          mol_type = protein
                          organism = synthetic construct
SEQUENCE: 51
MAKRFYSAEE AAAHCMASSQ EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLLLFKGRLQ FKQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGVY LIQMALRNSY   480
IVYKAAVPGP KLSYYKYQLQ ILPALLFGGV EEQTVPEMPD SDNVARLIGK HFIDTLPPTP   540
GKQRPQKGCK VCRKRGIRRD TRYYCPKCPR NPGLCRKPCF EIYHTQLHY              589

SEQ ID NO: 52             moltype = AA  length = 589
FEATURE                   Location/Qualifiers
REGION                    1..589
                          note = Synthetic
source                    1..589
                          mol_type = protein
                          organism = synthetic construct
SEQUENCE: 52
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD ICEMKRFVGL TLAMGLIKAN   180
SLESYWDTTT VLSIPVFGAT MSRNRYQLLL RFLHFNNNAT AVPPDQPGHD RLHKLRPLID   240
SLSERFANVY TPCQNICIDE SLLLFKGRLQ FRQYIPSKRA RYGIKFYKLC ESSTGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RHWYKKVGVY LIQMALRNSY   480
IVYKAAVPGP KLSYYKYQLQ ILPALLFGGV EEQTVPEMPD SDNVARLIGK HFIDTLPPTP   540
GKQRPQKGCK VCRKRGIRRD TRYYCPKCPR NPGLCRKPCF EIYHTQLHY              589

SEQ ID NO: 53             moltype = AA  length = 589
FEATURE                   Location/Qualifiers
REGION                    1..589
                          note = Synthetic
source                    1..589
                          mol_type = protein
                          organism = synthetic construct
SEQUENCE: 53
MAKRFYSAEE AAAHCMASSS EQTSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRY ARAHAWHPTD IAEMKRFVGL TLAMGLIKAN   180
SIESYWDTTT VLSIPVFGAT MSRNRYQLLL RFLHFNNNAT AVPPDQPGHD RLHKLRPLID   240
SLSERFANVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLNT   360
PACGTINRNR KGLPRALLDK KLNRGETYAL RKNELLAIKF FDKKNVFMLT SIHDESVIRE   420
QRVGRPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCRKPCF EIYHTQLHY              589

SEQ ID NO: 54             moltype = AA  length = 589
FEATURE                   Location/Qualifiers
REGION                    1..589
                          note = Synthetic
source                    1..589
                          mol_type = protein
                          organism = synthetic construct
SEQUENCE: 54
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNPLTRG ARAHAWHPTD IAEMKRFVGL TLAMGLIKAN   180
SLESYWDTTT VLSIPVFGAT MSRNRYQLLL RFLHFNNNAT AVPPDQPGHD RLHKLRPLID   240
```

```
SLSERFANVY TPCQNICIDE SLMLFKGRLQ FRQYIPSKRA RYGIKFYKLC ESSTGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 55              moltype = AA  length = 589
FEATURE                    Location/Qualifiers
REGION                     1..589
                           note = Synthetic
source                     1..589
                           mol_type = protein
                           organism = synthetic construct
SEQUENCE: 55
MAKRFYSAEE AAAHCSASSS EEFSGSDSEY VPPASESDSS TEESWCSSST VSALEEPMEV  60
DEDVDDLEDQ EAHDRADAAA GGEPAWGPPC NFPPEIPPFT TVPGVKVDTS NFEPINFFQL  120
FMTEAILQDM VLYTNVYAEQ YLTQNPLTRG ARAHAWHPTD IAEMKRFVGL TLAMGLIKAN  180
SIESYWDTTT VLSIPVFGAT MSRNRYQLLH RFLHFNNNAT AVPPDQPGHD RLHKLRPLID  240
SLSERFANVY TPCQNICIDE SLMLFKGRLQ FRQYIPSKRA RYGIKFYKLC ESSTGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 56              moltype = AA  length = 589
FEATURE                    Location/Qualifiers
REGION                     1..589
                           note = Synthetic
source                     1..589
                           mol_type = protein
                           organism = synthetic construct
SEQUENCE: 56
MAKRFYSAEE AAAHCSASSS EEFSGSDSEY VPPASESDSS TEESWCSSST VSALEEPMEV  60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRG ARAHAWHPTD IAEMKRFVGL TLAMGLIKAN  180
SIESYWDTTT VLSIPVFGAT MSRNRYQLLL RFLHFNNNAT AVPPDQPGHD RLHKLRPLID  240
SLSERFANVY TPCQNICIDE SLMLFKGRLQ FRQYIPSKRA RYGIKFYKLC ESSTGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPD SDNVARLIGK HFIDTLPPTP  540
GKQRPQKGCK VCRKRGIRRD TRYYCPKCPR NPGLCRKPCF EIYHTQLHY             589

SEQ ID NO: 57              moltype = AA  length = 589
FEATURE                    Location/Qualifiers
REGION                     1..589
                           note = Synthetic
source                     1..589
                           mol_type = protein
                           organism = synthetic construct
SEQUENCE: 57
MAKRFYSAEE AAAHCSASSS EQFSGSDSEY VPPASESDSS TEESWCSSST VSALEEPMEV  60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRG ARAHAWYPTD IAEMKRFVGL TLAMGLIKAN  180
SIESYWDTTT VLSIPVFGAT MSRNRYQLLL RFLHFNNNAT AVPPDQPGHD RLHKLRPLID  240
SLSERFANVY TPCQNICIDE SLMLFKGRLQ FRQYIPSKRA RYGIKFYKLC ESSTGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRGDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 58              moltype = AA  length = 589
FEATURE                    Location/Qualifiers
REGION                     1..589
                           note = Synthetic
source                     1..589
                           mol_type = protein
                           organism = synthetic construct
SEQUENCE: 58
MAKRFYSAEE AAAHCSASSS EEFSGSDSEY VPPASESDSS TEESWCSSST VSALEEPMEV  60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRG ARAHAWHPTD IAEMKRFVGL TLAMGLIKAN  180
SIESYWDTTT VLSIPVFGAT MSRNRYQLLL RFLHFNNNAT AVPPDQPGHD RLHKLRPLID  240
SLSERFANVY TPCQNICIDE SLMLFKGRLQ FRQYIPSKRA RYGIKFYKLC ESSTGYMSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
```

```
QRVGRKPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDSVARLIGK HFIDTLPPTP    540
GKQRPQKGCK VCRKRGIRRD TRYYCPKCPR NPGLCRKPCF EIYHTQLHY                589

SEQ ID NO: 59           moltype = AA   length = 589
FEATURE                 Location/Qualifiers
REGION                  1..589
                        note = Synthetic
source                  1..589
                        mol_type = protein
                        organism = synthetic construct
SEQUENCE: 59
MAKRFYSAEE AAAHCMASSS EEFYGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRY ARAHAWHPTD IAEMKRFVGL TLAMGLIKAN    180
SLESYWDTTT VLSIPVFGAT MSRNRYQLLL RFLHFNNNAT AVPPDQPGHD RLHKLRPLID    240
SLSERFANVY TPCQNICIDE SLLLFKGRLQ FKQYIPSKRA RYGIKFYKLC ESSSGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPD SDNVARLIGK HFIDTLPPTP    540
GKQRPQKGCK VCRKRGIRRD TRYYCPKCPR NPGLCRIPCF EIYHTQLHY                589

SEQ ID NO: 60           moltype = AA   length = 589
FEATURE                 Location/Qualifiers
REGION                  1..589
                        note = Synthetic
source                  1..589
                        mol_type = protein
                        organism = synthetic construct
SEQUENCE: 60
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRY ARAHAWHPTD ICEMKRFVGL TLAMGLIKAN    180
SIESYWDTTT VLSIPVFGAT MSRNRYQLLL RFLHFNNNAT AVPPDQPGHD RLHKLRPLID    240
SLSERFANVY TPCQNICIDE SLMLFKGRLQ FRQYIPSKRA RYGIKFYKLC ESSTGYTSYF    300
LIYEGKDSKL DPPGCPPDLT VSGKIVWELI SPLLGQGFHL YVDNFYSSIP LFTALYVLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCRKPCF EIYHTQLHY                589

SEQ ID NO: 61           moltype = AA   length = 589
FEATURE                 Location/Qualifiers
REGION                  1..589
                        note = Synthetic
source                  1..589
                        mol_type = protein
                        organism = synthetic construct
SEQUENCE: 61
MAKRFYSAEE AAAHCSASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRY ARAHAWYPTD IAEMKRFVGL TLAMGLIKAN    180
SLESYWDTTT VLSIPVFGAT MSRNRYQLLL RFLHFNNNAT AVPPDQPGHD RLHKLRPLID    240
SLSERFANVY TPCQNICIDE SLMLFKGRLQ FRQYIPSKRA RYGIKFYKLC ESSTGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RHWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCRKPCF EIYHTQLHY                589

SEQ ID NO: 62           moltype = AA   length = 589
FEATURE                 Location/Qualifiers
REGION                  1..589
                        note = Synthetic
source                  1..589
                        mol_type = protein
                        organism = synthetic construct
SEQUENCE: 62
MAKRFYSAEE AAAHCSASSS DEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL    120
FMTEAILQDM VLYTNVYAEQ YLTQNPLTRG ARAHAWYPTD IAEMKRFVGL TLAMGLIKAN    180
SLESYWDTTT VLSIPVFGAT MSRNRYQLLL RFLHFNNNAT AVPPDQPGHD RLHKLRPLID    240
SLSERFANVY TPCQNICIDE SLMLFKGRLQ FRQYIPSKRA RYGIKFYKLC ESSTGYTSYF    300
LIYEGKDSKL DPPGCPPDLT VSGKIVWELI SPLLGQGFHL YVDNFYSSIP LFTALYCLNT    360
PACGTINRNR KGLPRALLDK KLNRGETYAL RKNELLAIKF FDKKNVFMLT SIHDESVIRE    420
QRVGRPKPKNK PLCSKEYSKY MGGVDRTDQL QHYYNATRKT RHWYKKVGIY LIQMALRNSY   480
IVYKAAVPGP KLSYYKYQLQ ILPALLFGGV EEQTVPEMPP SDSVARLIGK HFIDTLPPTP    540
GKQRPQKGCK VCRKRGIRRD TRYYCPKCPR NPGLCRKPCF EIYHTQLHY                589
```

```
SEQ ID NO: 63              moltype = AA   length = 589
FEATURE                    Location/Qualifiers
REGION                     1..589
                           note = Synthetic
source                     1..589
                           mol_type = protein
                           organism = synthetic construct
SEQUENCE: 63
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRY ARAHAWHPTD IAEMKRFVGL TLAMGLIKAN  180
SLESYWDTTT VLSIPVFGAT MSRNRYQLLL RFLHFNNNAT AVPPDQPGHD RLHKLRPLID  240
SLSERFANVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 64              moltype = AA   length = 589
FEATURE                    Location/Qualifiers
REGION                     1..589
                           note = Synthetic
source                     1..589
                           mol_type = protein
                           organism = synthetic construct
SEQUENCE: 64
MAKRFYSAEE AAAHCMASSS EETSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRY ARAHAWHPTD IAEMKRFVGL TLAMGLIKAN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRHGRPPKNK PLCSKEYSKY MGGVDRADQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 65              moltype = AA   length = 589
FEATURE                    Location/Qualifiers
REGION                     1..589
                           note = Synthetic
source                     1..589
                           mol_type = protein
                           organism = synthetic construct
SEQUENCE: 65
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRY ARAHAWHPTD IAEMKRFVGL TLAMGLIKAN  180
SLESYWDTTT VLSIPVFSAT MSRNRYQLLL RFLHFNNEAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 66              moltype = AA   length = 589
FEATURE                    Location/Qualifiers
REGION                     1..589
                           note = Synthetic
source                     1..589
                           mol_type = protein
                           organism = synthetic construct
SEQUENCE: 66
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRY ARAHAWHPTD IAEMKRFVGL TLAMGLIKAN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 67              moltype = AA   length = 589
FEATURE                    Location/Qualifiers
```

```
REGION                      1..589
                            note = Synthetic
source                      1..589
                            mol_type = protein
                            organism = synthetic construct
SEQUENCE: 67
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRY ARAHAWHPTD IAEMKRFVGL TLAMGLIKAN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCRKPCF EIYHTQLHY             589

SEQ ID NO: 68               moltype = AA  length = 589
FEATURE                     Location/Qualifiers
REGION                      1..589
                            note = Synthetic
source                      1..589
                            mol_type = protein
                            organism = synthetic construct
SEQUENCE: 68
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLPRY ARAHAWHPTD IAEMKRFVGL TLAMGLIKAN  180
SLESYWDTTT VLKIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLNT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RHWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQLHY             589

SEQ ID NO: 69               moltype = AA  length = 589
FEATURE                     Location/Qualifiers
REGION                      1..589
                            note = Synthetic
source                      1..589
                            mol_type = protein
                            organism = synthetic construct
SEQUENCE: 69
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ QLTQNPLPRY ARAHAWHPTD IAEMKRFVGL TLAMGLIKAN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDRKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQYHY             589

SEQ ID NO: 70               moltype = AA  length = 589
FEATURE                     Location/Qualifiers
REGION                      1..589
                            note = Synthetic
source                      1..589
                            mol_type = protein
                            organism = synthetic construct
SEQUENCE: 70
MAKRFYSAEE AAAHCMASSS EEPSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLPRY ARAHAWHPTD IAEMKRFVGL TLAMGLIKAN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTHLYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQYHY             589

SEQ ID NO: 71               moltype = AA  length = 592
FEATURE                     Location/Qualifiers
REGION                      1..592
                            note = Synthetic
source                      1..592
```

```
                        mol_type = protein
                        organism = synthetic construct
SEQUENCE: 71
MAKRFYSAEE AAAHCMASSQ EEFSGSDSEY VPPASESDSS TEESWCSSST VSALEEPMEV   60
DEDVDDLEDQ EAGDRVDAAA GGEPAWGPPC NFPPEIPPFT TVPGVKVDTS NFEPINFFQL  120
FMTEAILQDM VLYTNVYAEQ YLTQNPLPRY ARAHAWHPTD IAEMKRFVGL TLAMGLIKKN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQLHYG RR          592

SEQ ID NO: 72           moltype = AA   length = 592
FEATURE                 Location/Qualifiers
REGION                  1..592
                        note = Synthetic
source                  1..592
                        mol_type = protein
                        organism = synthetic construct
SEQUENCE: 72
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNKLPRY ARAHAWHPTD IAEMKRFVGL TLAMGLIKAN  180
SLESYWDTGT VHSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQLHYG RR          592

SEQ ID NO: 73           moltype = AA   length = 592
FEATURE                 Location/Qualifiers
REGION                  1..592
                        note = Synthetic
source                  1..592
                        mol_type = protein
                        organism = synthetic construct
SEQUENCE: 73
MAKRFCSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQNPLTRY ARAHAWHPTD IAEMKRFVGL TLAMGLIKAN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIATLPPTP  540
GKQRPQKGCK VCRKRGIRRD TRYYCPKCPR NPGLCFKPCF EIYHTQLHYG RR          592

SEQ ID NO: 74           moltype = AA   length = 592
FEATURE                 Location/Qualifiers
REGION                  1..592
                        note = Synthetic
source                  1..592
                        mol_type = protein
                        organism = synthetic construct
SEQUENCE: 74
MAKRFYSAEE AAAHCMASSS EEFSGSDSEY VPPASESDSS TEESWCSSST VSALEEPMEV   60
DEDVDDLEDQ EAGDRADAAA GGEPAWGPPC NFPPEIPPFT TVPGVKVDTS NFEPINFFQL  120
FMTEAILQDM VLYTNVYAEQ YLTQVPLTRY ARAHAWHPTD IAEMKRFVGL TLAMGLIKKN  180
SLESYWDTTT VLSIPVFSAT MSRNRYQLLL RFLHFNNNAT AVPPDQPGHD RLHKLRPLID  240
SLSERFAAVY TPCQNICIDE SLLLFKGRLQ FRQYIPSKRA RYGIKFYKLC ESSSGYTSYF  300
LIYEGKDSKL DPPGCPPDLT VSGKIVWELI SPLLGQGFHL YVDNFYSSIP LFTALYCLDT  360
PACGTINRNR KGLPRALLDK KLNRGETYAL RKNELLAIKF FDKKNVFMLT SIHDESVIRE  420
QRVGRPPKNK PLCSKEYSKY MGGVDRTDQL QHYYNATRKT RAWYKKVGIY LIQMALRNSY  480
IVYKAAVPGP KLSYYKYQLQ ILPALLFGGV EEQTVPEMPP SDNVARLIGK HFIDTLPPTP  540
GKQRPQKGCK VCRKRGIRRD TRYYCPKCPR NPGLCFKPCF EIYHTQLHYG RR          592

SEQ ID NO: 75           moltype = AA   length = 592
FEATURE                 Location/Qualifiers
REGION                  1..592
                        note = Synthetic
source                  1..592
                        mol_type = protein
                        organism = synthetic construct
SEQUENCE: 75
```

```
MAKRFYSAEE AAAHCMASSS EEFSGSDQEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNKLTRY ARAHAWHPTD IAEMKRFVGL TLAMGLIKAN   180
SLESYWDTTT VLSIPVFSAT MSRNRYQLLL RFLHFNNNAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 76            moltype = AA  length = 592
FEATURE                  Location/Qualifiers
REGION                   1..592
                         note = Synthetic
source                   1..592
                         mol_type = protein
                         organism = synthetic construct
SEQUENCE: 76
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQNVLPRY ARAHAWHPTD IAEMKRFVGL TLAMGLIKAN   180
SLESYWDTTT VLSIPVFSAT MSRNRYQLLL RFLHFNNDAT AVPPDQPGHD RLHKLRPLID   240
SLTERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 77            moltype = AA  length = 592
FEATURE                  Location/Qualifiers
REGION                   1..592
                         note = Synthetic
source                   1..592
                         mol_type = protein
                         organism = synthetic construct
SEQUENCE: 77
MAKRFYSAEE AAAHCMASSS EEFSGSDSEY VPPASESDSS TEESWCSSST VSALEEPMEV    60
DEDVDDLEDQ EAGDRADAAP GGEPAWGPPC NFPPEIPPFT TVPGVKVDTS NFEPINFFQL   120
FMTEAILQDM VLYTNVYAEQ YLTQVPLPRY ARAHAWHPTD IAEMKRFVGL TLAMGLIKAN   180
SLESYWDTTT VLSIPVFSAT MSRNRYQLLL RFLHFNNEAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 78            moltype = AA  length = 592
FEATURE                  Location/Qualifiers
REGION                   1..592
                         note = Synthetic
source                   1..592
                         mol_type = protein
                         organism = synthetic construct
SEQUENCE: 78
MAKRFYSAEE AAAHCMASSS EEFSGSDSEY VPPASESDSS TEESWCSSST VSALEEPMEV    60
DEDVDDLEDQ EAGDRVDAAA GGEPAWGPPC NFPPEIPPFT TVPGVKVDTS NFEPINFFQL   120
FMTEAILQDM VLYTNVYAEQ YLTQNPLPRY ARAHAWHPTD IAEMKRFVGL TLAMGLIKAN   180
SLESYWDTTT VLSIPVFSAT MSRNRYQLLL KFLHFNNEAT AVPPDQPGHD RLHKLRPLID   240
SLSERFAAVY TPCQNICIDE SLLLFKGRLQ FRQYIPSKRA RYGIKFYKLC ESSSGYTSYF   300
LIYEGKDSKL DPPGCPPDLT VSGKIVWELI SPLLGQGFHL YVDNFYSSIP LFTALYCLDT   360
PACGTINRNR KGLPRALLDK KLNRGETYAL RKNELLAIKF FDKKNVFMLT SIHDESVIRE   420
QRVGRPPKNK PLCSKEYSKY MGGVDRTDQL QHYYNATRKT RAWYKKVGIY LIQMALRNSY   480
IVYKAAVPGP KLSYYKYQLQ ILPALLFGGV EEQTVPEMPP SDNVARLIGK HFIDTLPPTP   540
GKQRPQKGCK VCRKRGIRRD TRYYCPKCPR NPGLCFKPCF EIYHTQLHYG RR           592

SEQ ID NO: 79            moltype = AA  length = 592
FEATURE                  Location/Qualifiers
REGION                   1..592
                         note = Synthetic
source                   1..592
                         mol_type = protein
                         organism = synthetic construct
SEQUENCE: 79
MAKRFYSAEE AAAHCMASSS EEFSGSDSEY VPPASESDSS TEESWCSSST VSALEEPMEV    60
DEDVDDLEDQ EAGDRADAAA GGEPAWGPPC NFPPEIPPFT TVPGVKVDTS NFEPINFFQL   120
FMTEAILQDM VLYTNVYAEQ YLTQVPLPRY ARAHAWHPTD IAEMKRFVGL TLAMGLIKAN   180
```

```
SLESYWDTTT VLNIPVFSAT MSRNRYQLLL RFLEFNNNAT AVPPDQPGHD RLHKLRPLID    240
SLSERFAAVY TPCQNICIDE SLLLFKGRLQ FRQYIPSKRA RYGIKFYKLC ESSSGYTSYF    300
LIYEGKDSKL DPPGCPPDLT VSGKIVWELI SPLLGQGFHL YVDNFYSSIP LFTALYCLDT    360
PACGTINRNR KGLPRALLDK KLNRGETYAL RKNELLAIKF FDKKNVFMLT SIHDESVIRE    420
QRVGRPPKNK PLCSKEYSKY MGGVDRTDQL QHYYNATRKT RAWYKKVGIY LIQMALRNSY    480
IVYKAAVPGP KLSYYKYQLQ ILPALLFGGV EEQTVPEMPP SDNVARLIGK HFIDTLPPTP    540
GKQRPQKGCK VCRKRGIRRD TRYYCPKCPR NPGLCFKPCF EIYHTQLHYG RR            592

SEQ ID NO: 80              moltype = DNA   length = 16
FEATURE                    Location/Qualifiers
misc_feature               1..16
                           note = Synthetic
source                     1..16
                           mol_type = other DNA
                           organism = synthetic construct
SEQUENCE: 80
cccggcgagc atgagg                                                    16

SEQ ID NO: 81              moltype = DNA   length = 16
FEATURE                    Location/Qualifiers
misc_feature               1..16
                           note = Synthetic
source                     1..16
                           mol_type = other DNA
                           organism = synthetic construct
SEQUENCE: 81
cctcatgctc gccggg                                                    16

SEQ ID NO: 82              moltype = DNA   length = 205
FEATURE                    Location/Qualifiers
misc_feature               1..205
                           note = Synthetic
source                     1..205
                           mol_type = other DNA
                           organism = synthetic construct
SEQUENCE: 82
cagggtatct cataccctgg taaaattta aagttgtgta ttttataaaa ttttcgtctg      60
acaacactag cgcgctcagt agctggaggc aggagcgtgc gggaggggat agtggcgtga    120
tcgcagtgtg gcacgggaca ccggcgagat attcgtgtgc aaacctgttt cgggtatgtt    180
ataccctgcc tcattgttga cgtat                                         205

SEQ ID NO: 83              moltype = DNA   length = 192
FEATURE                    Location/Qualifiers
misc_feature               1..192
                           note = Synthetic
source                     1..192
                           mol_type = other DNA
                           organism = synthetic construct
SEQUENCE: 83
tttaagaaaa agattaataa ataataataa tttcataatt aaaaacttct ttcattgaat     60
gccattaaat aaaccattat tttacaaaat aagatcaaca taattgagta aataataata   120
agaacaatat tatagtacaa caaaatatgg gtatgtcata ccctgccaca ttcttgatgt   180
aactttttt ca                                                        192

SEQ ID NO: 84              moltype = AA    length = 610
FEATURE                    Location/Qualifiers
REGION                     1..610
                           note = Synthetic
source                     1..610
                           mol_type = protein
                           organism = synthetic construct
SEQUENCE: 84
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYL AGLIKSNRQS LKDLWRTDGT GVDIFRTTMS LQRFQFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                          610

SEQ ID NO: 85              moltype = AA    length = 610
FEATURE                    Location/Qualifiers
REGION                     1..610
                           note = Synthetic
source                     1..610
```

```
                        mol_type = protein
                        organism = synthetic construct
SEQUENCE: 85
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRWRQTKT AAENSSAETS  180
FYMQETTLCE LKALIGLLYI AGLIKSNRQS LKDLWRTDGT GVDIFRTTMS LQRFQFLLNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVHNLEVYA GKQPSGPYAV SNRPFEVVER LIQPVARSHR  360
NVTFDNWFTG YEVMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAHLDSSL                                                         610

SEQ ID NO: 86          moltype = AA  length = 610
FEATURE                Location/Qualifiers
REGION                 1..610
                        note = Synthetic
source                 1..610
                        mol_type = protein
                        organism = synthetic construct
SEQUENCE: 86
MDIERQEERI RAMLEEELSD YSDESSSEDE TDHCSEHEVN YDTEEERIDS VDVPSNSRQE   60
EANAIIANES DSDPDDDLPL SLVRERASAS RQVSGPFYTS KDGTKWYKNC QRPNVRLRSE  120
NIVTEQAQVK NIARDASTEY ECWNIFVTSD MLQEILTHTN SSIRWRQTKT AAENSSAETS  180
FYMQETTLCE LKALIGLLYI AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELQANYNVSR  480
NSKRWPMTLF YGVLNMAAIN ACIIYRTNKN VTIKRTEFIR SLGLSMIKEH LHSRNKKKNI  540
PTYLRQRIEK QLGEPSPRHV NVPGRYVRCQ DCPYKKDRKT KRSCNACAKP ICMEHAKFLC  600
ENCAELDSSI                                                         610

SEQ ID NO: 87          moltype = AA  length = 610
FEATURE                Location/Qualifiers
REGION                 1..610
                        note = Synthetic
source                 1..610
                        mol_type = protein
                        organism = synthetic construct
SEQUENCE: 87
MDIERQEERI RAMLEEELSD YSDESSSEDE TDHCSEHEVN YDTEEERIDS VDVPSNSRQE   60
EANAIIANES DSDPDDDLPL SLVRQRASAS RAVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYI AGLIKSNRQS LKDLWRTDGT GVDIFRTTMS LQRFQFLLNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRCNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                         610

SEQ ID NO: 88          moltype = AA  length = 610
FEATURE                Location/Qualifiers
REGION                 1..610
                        note = Synthetic
source                 1..610
                        mol_type = protein
                        organism = synthetic construct
SEQUENCE: 88
MDIERQEERI RAMLEEELSD YSDESSSEDE TDHCSEHEVN YDTEEERIDS VDVPSNSRQE   60
EANAIIANES DSDPDDDLPL SLVRQRASAS RQMSGPHYTS KDGTKWYKNC QRPNVRLRSE  120
NIVTEQAQVK NIARDASTEY ECWNIFVTSD MLQEILTHTN SSIRWRQTKT AAENSSASTS  180
FYMQETTLCE LKALIGLLYI AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSHL                                                         610

SEQ ID NO: 89          moltype = AA  length = 610
FEATURE                Location/Qualifiers
REGION                 1..610
                        note = Synthetic
```

```
source                    1..610
                          mol_type = protein
                          organism = synthetic construct
SEQUENCE: 89
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRWRQTKT AAENSSASTS    180
FYMQETTLCE LKALIGLLYI AGLIKSNRQS LKDLWRTDGT GVDIFRTTMS LQRFQFLLNN    240
IRFDDKSTRD ERKQTDNMAA FRSIFDQFVQ SCQNAYSPSE FLTIDEMLLS FRGRCLFRVY    300
IPNKPAKYGI KILALVDAKN FYVKNLEVYA GKQPSGPYAV SNRPFEVVER LIQPVARSHR    360
NVTFDNWFTG YELMLHLLNE YRLTSVGTVR KNKRQIPESF IRTDRQPNSS VFGFQKDITL    420
VSYAPKKNKV VVVMSTMHHD NSIDESTGEK QKPEMITFYN STKAGVDVVD ELCANYNVSR    480
NSKRWPMTLF YGVLNMAAIN ACIIYRTNKN VTIKRTEFIR SLGLSMIYEH LHSRNKKKNI    540
PTYLRQRIAM QLGEPSPRHV NVPGRYVRCQ DCPYKKDRKT KRSCNACAKP ICMEHAKFLC    600
ENCAELDSSL                                                          610

SEQ ID NO: 90             moltype = AA  length = 610
FEATURE                   Location/Qualifiers
REGION                    1..610
                          note = Synthetic
source                    1..610
                          mol_type = protein
                          organism = synthetic construct
SEQUENCE: 90
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRWRQTKT AAENSSAETS    180
FYMQETTLCE LKALIGLLYI AGLIKSNRQS LKDLWRTDGT GVDIFRTTMS LQRFQFLLNN    240
IRFDDKSTRD ERKQTDNMAA FRSIFDQFVQ SCQNAYSPSE FLTIDEMLLS FRGRCLFRVY    300
IPNKPAKYGI KILALVDAKN FYVKNLEVYA GKQPSGPYAV SNRPFEVVER LIQPVARSHR    360
NVTFDNWFTG YELMLHLLNE YRLTSVGTVR KNKTQIPENF IRTDRQPNSS VFGFQKDITL    420
VSYAPKKNKV VVVMSTMHHD NSIDESTGEK QKPEMITFYN STKAGVDVVD ELQANYNVSR    480
NSKRWPMTLF YGVLNMAAIN ACIIYRTNKN VTIKRTEFIR SLGLSMIYEH LHSRNKKKNI    540
PTYLRQRIEK QLGEPSPRHV NVPGRYVRCQ DCPYKKDRKT KRSCNACAKP ICMEHAKFLC    600
ENCAELDSSL                                                          610

SEQ ID NO: 91             moltype = AA  length = 610
FEATURE                   Location/Qualifiers
REGION                    1..610
                          note = Synthetic
source                    1..610
                          mol_type = protein
                          organism = synthetic construct
SEQUENCE: 91
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRWRQTKT AAENSSAETS    180
FYMQETTLCE LKALIGLLYL AGLIKSNRQS LKDLWRTDGT GVDIFRTTMS LQRFQFLQNN    240
IRFDDKSTRD ERKQTDNMAA FRSIFDQFVQ SCQNAYSPSE FLTIDEMLLS FRGRCLFRVY    300
IPNKPAKYGI KILALVDAKN FYVVNLEVYA GKQPSGPYAV SNRPFEVVER LIQPVARSHR    360
NVTFDNWFTG YELMLHLLNE YRLTSVGTVR KNKRQIPESF IRTDRQPNSS VFGFQKDITL    420
VSYAPKKNKV VVVMSTMHHD NSIDESTGEK QKPEMITFYN STKAGVDVVD ELQANYNVSR    480
NSKRWPMTLF YGVLNMAAIN ACIIYRTNKN VTIKRTEFIR SLGLSMIKEH LHSRNKKKNI    540
PTYLRQRIEK QLGEPSPRHV NYPGRYVRCQ DCPYKKDRKT KRSCNACAKP ICMEHAKFLC    600
ENCAELDSSL                                                          610

SEQ ID NO: 92             moltype = AA  length = 610
FEATURE                   Location/Qualifiers
REGION                    1..610
                          note = Synthetic
source                    1..610
                          mol_type = protein
                          organism = synthetic construct
SEQUENCE: 92
MDIERQEERI RAMLEEELSD YSDESSSEDE TDHCSEHEVN YDTEEERIDS VDVPSNSRQE     60
EANAIIANES DSDPDDDLPL SLVRQRASAS RQVSGPFYTS KDGTKWYKNC QRPNVRLRSE    120
NIVTEQAQVK NIARDASTEY ECWNIFVTSD MLQEILTHTN SSIRWRQTKT AAENSSAETS    180
FYMQETTLCE LKALIGLLYI AGLIKSNRQS LKDLWRTDGT GVDIFRTTMS LQRFQFLQNN    240
IRFDDKSTRD ERKQTDNMAA FRSIFDQFVQ SCQNAYSPSE FLTIDEMLLS FRGRCLFRVY    300
IPNKPAKYGI KILALVDAKN FYVKNLEVYA GKQPSGPYAV SNRPFEVVER LIQPVARSHR    360
NVTFDNWFTG YELMLHLLNE YRLTSVGTVR KNKRQIPESF IRTDRQPNSS VFGFQKDITL    420
VSYAPKKNKV VVVMSTMHHD NSIDESTGEK QKPEMITFYN STKAGVDVVD ELCANYNVSR    480
NSKRWPMTLF YGVLNMAAIN ACIIYRTNKN VTIKRTEFIR SLGLSMIYEH LHSRNKKKNI    540
PTYLRQRIEK QLGEPSPRHV NVPGRYVRCQ DCPYKKDRKT KRSCNACAKP ICMEHAKFLC    600
ENCAELDSSL                                                          610

SEQ ID NO: 93             moltype = AA  length = 610
FEATURE                   Location/Qualifiers
REGION                    1..610
```

```
                            note = Synthetic
source                      1..610
                            mol_type = protein
                            organism = synthetic construct
SEQUENCE: 93
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRWRQTKT AAENSSAETS  180
FYMQETTLCE LKALIGLLYL AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVVNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIKEH LHSRNKKKNI  540
PTYLRQRIEK QLGEPSPRHV NYPGRYVRCQ DCPYKKDRKT KRSCNACAKP ICMEHAKFLC  600
ENCAELHSSL                                                        610

SEQ ID NO: 94               moltype = AA   length = 610
FEATURE                     Location/Qualifiers
REGION                      1..610
                            note = Synthetic
source                      1..610
                            mol_type = protein
                            organism = synthetic construct
SEQUENCE: 94
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYL AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTSRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610

SEQ ID NO: 95               moltype = AA   length = 610
FEATURE                     Location/Qualifiers
REGION                      1..610
                            note = Synthetic
source                      1..610
                            mol_type = protein
                            organism = synthetic construct
SEQUENCE: 95
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYI AGLIKSNRQS LKDLWRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVKNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELCANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NVPGRYVRCQ DCPYKKDRKT KRSCNACAKP ICMEHAKFLC  600
ENCAELDSSL                                                        610

SEQ ID NO: 96               moltype = AA   length = 610
FEATURE                     Location/Qualifiers
REGION                      1..610
                            note = Synthetic
source                      1..610
                            mol_type = protein
                            organism = synthetic construct
SEQUENCE: 96
MDIERQEERI RAMLEEELSD YSDESSSEDE TDHCSEHEVN YDTEEERIDS VDVPSNSRQE   60
EANAIIANES DSDPDDDLPL SLVRQRASAS RQVSGPFYTS KDGTKWYKNC QRPNVRLRSE  120
NIVTEQAQVK NIARDASTEY ECWNIFVTSD MLQEILTHTN SSIRHRQTKT AAENSSAETS  180
FYMQETTLCE LKALIGLLYI AGLIKSNRQS LKDLYRTDGT GVDIFRTTMS LQRFQFLQNN  240
IRFDDKSTRD ERKQTDNMAA FRSIFDQFVQ SCQNAYSPSE FLTIDEMLLS FRGRCLFRVY  300
IPNKPAKYGI KILALVDAKN FYVVNLEVYA GKQPSGPYAV SNRPFEVVER LIQPVARSHR  360
NVTFDNWFTG YELMLHLLNE YRLTSVGTVR KNKRQIPESF IRTDRQPNSS VFGFQKDITL  420
VSYAPKKNKV VVVMSTMHHD NSIDESTGEK QKPEMITFYN STKAGVDVVD ELQANYNVSR  480
NSKRWPMTLF YGVLNMAAIN ACIIYRTNKN VTIKRTEFIR SLGLSMIYEH LHSRNKKKNI  540
PTYLRQRIEK QLGEPSPRHV NYPGRYVRCQ DCPYKKDRKT KRSCNACAKP ICMEHAKFLC  600
ENCAELDSSL                                                        610

SEQ ID NO: 97               moltype = AA   length = 610
FEATURE                     Location/Qualifiers
```

| REGION | 1..610 |
| --- | --- |
| | note = Synthetic |
| source | 1..610 |
| | mol_type = protein |
| | organism = synthetic construct |

SEQUENCE: 97

```
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYI AGLIKSNRQS LKDLWRKDGT GVDIFRTTMS LQRFQFLLNN   240
IRFDDISTRD ERKQTDNMAA FRSIFDQFVQ CCQNAYSPSE FLTIDEMLLS FGRCLFRVY    300
IPNKPAKYGI KILALVDAKN FYVHNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKKWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610
```

| SEQ ID NO: 98 | moltype = AA length = 610 |
| --- | --- |
| FEATURE | Location/Qualifiers |
| REGION | 1..610 |
| | note = Synthetic |
| source | 1..610 |
| | mol_type = protein |
| | organism = synthetic construct |

SEQUENCE: 98

```
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYI AGLIKSNRQS LKDLWRTDGT GVDIFRTTMS LQRFQFLINN   240
IRFDDKSTRD ERKQTDNMAA FRSIFDQFVQ CCQNAYSPSE FLTIDEMLLS FGRCLFRVY    300
IPNKPAKYGI KILALVDAKN WYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610
```

| SEQ ID NO: 99 | moltype = AA length = 610 |
| --- | --- |
| FEATURE | Location/Qualifiers |
| REGION | 1..610 |
| | note = Synthetic |
| source | 1..610 |
| | mol_type = protein |
| | organism = synthetic construct |

SEQUENCE: 99

```
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYL AGLIKSNRQS AKDLWRTDGT GVDIFRTTMS LQRFYFLQNN   240
IRFDDKSTRD ERKQTDNMAA FRSIFDQFVQ CCQNAYSPSE FLTIDEMLLS FGRCLFRVY    300
IPNKPAKYGI KILALVDAKN FYVKNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610
```

| SEQ ID NO: 100 | moltype = AA length = 610 |
| --- | --- |
| FEATURE | Location/Qualifiers |
| REGION | 1..610 |
| | note = Synthetic |
| source | 1..610 |
| | mol_type = protein |
| | organism = synthetic construct |

SEQUENCE: 100

```
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLPE LKALIALLYL AGLIKSNRQS LKDLWRTDGT GVDVFRTTMS LQRFQFLQNN   240
IRFDDKSTRD ERKQTDNMAA FRSIFDQFVQ CCQNAYSPSE FLTIDEMLLS FGRCLFRVY    300
IPNKPAKYGI KILALVDAKN FYVVNLEVYV GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610
```

| SEQ ID NO: 101 | moltype = AA length = 610 |
| --- | --- |

```
FEATURE                 Location/Qualifiers
REGION                  1..610
                        note = Synthetic
source                  1..610
                        mol_type = protein
                        organism = synthetic construct
SEQUENCE: 101
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRERQTKT AAENSSAETS   180
FYMQETTLCE LKALIALLYL AGLIKSNRQS LKDLWRTDGT GVDIFRTTMS LQRFQFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FYVKNLEVYV GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610

SEQ ID NO: 102          moltype = AA  length = 610
FEATURE                 Location/Qualifiers
REGION                  1..610
                        note = Synthetic
source                  1..610
                        mol_type = protein
                        organism = synthetic construct
SEQUENCE: 102
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIALLYL AGLIKSNRQS LKDLWRTDGT GVDIFRTTMS LQRFQFLQNN   240
IRFDDISTRD ERKQTDNMAA FRSIFDQFVQ CCQNAYSPSE FLTIDEMLLS FRGRCLFRVY   300
IPNKPAKYGI KILALVDAKN DYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NYPGRYVRCQ DCPYKKDRKT KRSCNACAKP ICMEHAKFLC   600
ENCAELDSSL                                                         610

SEQ ID NO: 103          moltype = AA  length = 610
FEATURE                 Location/Qualifiers
REGION                  1..610
                        note = Synthetic
source                  1..610
                        mol_type = protein
                        organism = synthetic construct
SEQUENCE: 103
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIGLLYL AGLIKSNRQS LKDLYRTDGT GVDIFRTTMS LQRFGFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NVPGRYVRCQ DCPYKKDRKT KRSCNACAKP ICMEHAKFLC   600
ENCAELDSSL                                                         610

SEQ ID NO: 104          moltype = AA  length = 610
FEATURE                 Location/Qualifiers
REGION                  1..610
                        note = Synthetic
source                  1..610
                        mol_type = protein
                        organism = synthetic construct
SEQUENCE: 104
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAQVK NIARDASTEY ECWNIFVTSD MLQEILTHTN SSIRHRQTKT AAENSSAETS   180
FYMQETTLCE LKALIGLLYL AGLIKSNRQS LKDLWRTDGT GVDIFRTTMS LQRFQFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTILRQRIEK QLGEPSPRHV NVPGRYVRCQ DCPYKKDRKT KRSCNACAKP ICMEHAKFLC   600
VNCAELDSSL                                                         610
```

```
SEQ ID NO: 105              moltype = AA   length = 610
FEATURE                     Location/Qualifiers
REGION                      1..610
                            note = Synthetic
source                      1..610
                            mol_type = protein
                            organism = synthetic construct
SEQUENCE: 105
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAVQK NIARDASTEY ECWNIFVTSD MLQEILTHTN SSIRHRQTKT AAENSSAETS   180
FYMQETTLCE LKALIGLLYL AGLIKSNRQS LKDLWRTDGT GVDIFRTTMS LQRFQFLQNN   240
IRFDDKSTRD ERKQTDNMAA FRSIFDQFVQ SCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YELMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEK QLGEPSPRHV NYPGRYVRCQ DCPYKKDRKT KRSCNACAKP ICMEHAKFLC   600
ENCAELDSSL                                                         610

SEQ ID NO: 106              moltype = AA   length = 610
FEATURE                     Location/Qualifiers
REGION                      1..610
                            note = Synthetic
source                      1..610
                            mol_type = protein
                            organism = synthetic construct
SEQUENCE: 106
MDIERQEERI RAMLEEELSD YSDESSSEDE TDHCSEHEVN YDTEEERIDS VDVPSNSRQE    60
EANAIIANES DSDPDDDLPL SLVRQRASAS RQVSGPFYTS KDGTKWYKNC QRPNVRLRSE   120
NIVTEQAVQK NIARDASTEY ECWNIFVTSD MLQEILTHTN SSIRHRQTKT AAENSSAETS   180
FYMQETTLCE LKALIALLYL AGLIKSNRQS LKDLWRTDGT GVDIFRTTMS LQRFQFLQNN   240
IRFDDKSTRD ERKQTDNMAA FRSIFDQFVQ CCQNAYSPSE FLTIDEMLLS FRGRCLFRVY   300
IPNKPAKYGI KILALVDAKN FYVVNLEVYA GKQPSGPYAV SNRPFEVVER LIQPVARSHR   360
NVTFDNWFTG YECMLHLLNE YRLTSVGTVR KNKRQIPESF IRTDRQPNSS VFGFQKDITL   420
VSYAPKKNKV VVVMSTMHHD NSIDESTGEK QKPEMITFYN STKAGVDVVD ELCANYNVSR   480
NSKRWPMTLF YGVLNMAAIN ACIIYRTNKN VTIKRTEFIR SLGLSMIYEH LHSRNKKKNI   540
PTYLRQRIEM QLGEPSPRHV NYPGRYVRCQ DCPYKKDRKT KRSCNACAKP ICMEHAKFLC   600
ENCAELKSSL                                                         610

SEQ ID NO: 107              moltype = DNA   length = 15
FEATURE                     Location/Qualifiers
misc_feature                1..15
                            note = Synthetic
source                      1..15
                            mol_type = other DNA
                            organism = synthetic construct
SEQUENCE: 107
cacttggatt gcggg                                                    15

SEQ ID NO: 108              moltype = DNA   length = 15
FEATURE                     Location/Qualifiers
misc_feature                1..15
                            note = Synthetic
source                      1..15
                            mol_type = other DNA
                            organism = synthetic construct
SEQUENCE: 108
cccgacaccg tagtg                                                    15

SEQ ID NO: 109              moltype = DNA   length = 262
FEATURE                     Location/Qualifiers
misc_feature                1..262
                            note = Synthetic
source                      1..262
                            mol_type = other DNA
                            organism = synthetic construct
SEQUENCE: 109
aaacgagtta agtcggctcg cgtgaattgc gcgtactccg cgggagccgt cttaactcgg    60
ttcatataga tttgcggtgg agtgcgggaa acgtgtaaac tcgggccgat tgtaactgcg   120
tattaccaaa tatttgtttc caagcttggt accgagctcg gatcccgtac gctgcaggtc   180
gacggatccc cggttaatt aaggcgcgcc agatctgttt agcttgcctc gtccccgccg   240
ggtcacccgg ccagcgacat gg                                           262

SEQ ID NO: 110              moltype = DNA   length = 227
FEATURE                     Location/Qualifiers
misc_feature                1..227
                            note = Synthetic
source                      1..227
```

-continued

```
                        mol_type = other DNA
                        organism = synthetic construct
SEQUENCE: 110
tgtcgaagaa ttcggcggcc gcatgcatct agagaattat ttatgtactg aatagataaa    60
aaaatgtctg tgattgaata aatttttcatt ttttacacaa gaaaccgaaa atttcatttc   120
aatcgaaccc atacttcaaa agatataggc attttaaact aactctgatt ttgcgcggga   180
aacctaaata attgcccgcg ccatcttata ttttggcggg aaattca                 227

SEQ ID NO: 111          moltype = AA   length = 567
FEATURE                 Location/Qualifiers
REGION                  1..567
                        note = Synthetic
source                  1..567
                        mol_type = protein
                        organism = synthetic construct
SEQUENCE: 111
MSQHSDYSDD EFCADKLSNY SCDSDLENAS TSDEDSSDDE VMVRPRTLRR RRISSSSSDS    60
ESDIEGGREE WSHVDNPPVL EDFLGHQGLN TDAVINNIED AVKLFIGDDF FEFLVEESNR   120
YYNQNRNNFK LSKKSLKWKD ITPQEMKKFL GLIVLMGQVR KDRRDDYWTT EPWTETPYFG   180
KTMTRDRFRQ IWKAWHFNNN ADIVNESDRL CKVRPVLDYF VPKFINIYKP HQQLSLDEGI   240
VPWRGRLFFR VYNAGKIVKY GILVRLLCES DTGYICNMEI YCGEGKRLLE TIQTWSPYTD   300
SWYHIYMDNY YNSVANCEAL MKNKFRICGT IRKNRGIPKD FQTISLKKGE TKFIRKNDIL   360
LQVWQSKKPV YLISSHSAEM EESQNIDRTS KKKIVKPNAL IDYNKHMKGV DRADQYLSYY   420
SILRRWKWTK RLAMYMINCA LFNSYAVYKS VRQRKMGFKM FLKQTAHWLT DDIPEDMDIV   480
PDLQPVPSTS GMRAKPPTSD PPCRLSMDMR KHTLQAIVGS GKKKNILRRC RVCSVHKLRS   540
ETRYMCKFCN IPLHKGACFE KYHTLKN                                      567

SEQ ID NO: 112          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 112
ccctagaaag ata                                                      13

SEQ ID NO: 113          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 113
tatctttcta ggg                                                      13

SEQ ID NO: 114          moltype = DNA   length = 296
FEATURE                 Location/Qualifiers
misc_feature            1..296
                        note = Synthetic
source                  1..296
                        mol_type = other DNA
                        organism = synthetic construct
SEQUENCE: 114
gtctgcgtaa aattgacgca tgcattcttg aaatattgct ctctctttct aaatagcgcg    60
aatccgtcgc tgtgcattta ggacatctca gtcgccgctt ggagctcccg tgaggcgtgc   120
ttgtcaatgc ggtaagtgtc actgattttg aactataacg accgcgtgag tcaaaatgac   180
gcatgattat cttttacgtg actttttaaga tttaactcat acgataatta tattgttatt   240
tcatgttcta cttacgtgat aacttattat atatatattt tcttgttata gatatc       296

SEQ ID NO: 115          moltype = DNA   length = 218
FEATURE                 Location/Qualifiers
misc_feature            1..218
                        note = Synthetic
source                  1..218
                        mol_type = other DNA
                        organism = synthetic construct
SEQUENCE: 115
tttgttactt tatagaagaa attttgagtt tttgttttttt tttaataaat aaataaacat    60
aaataaattg tttgttgaat ttattattag tatgtaagtg taaatataat aaaacttaat   120
atctattcaa attaataaat aaacctcgat atacagaccg ataaaacaca tgcgtcaatt   180
ttacgcatga ttatctttaa cgtacgtcac aaatatgat                         218

SEQ ID NO: 116          moltype = AA   length = 594
FEATURE                 Location/Qualifiers
REGION                  1..594
                        note = Synthetic
source                  1..594
```

```
                            mol_type = protein
                            organism = synthetic construct
SEQUENCE: 116
MGSSLDDEHI LSALLQSDDE LVGEDSDSEV SDHVSEDDVQ SDTEEAFIDE VHEVQPTSSG    60
SEILDEQNVI EQPGSSLASN RILTLPQRTI RGKNKHCWST SKSTRRSRVS ALNIVRSQRG   120
PTRMCRNIYD PLLCFKLFFT DEIISEIVKW TNAEISLKRR ESMTSATFRD TNEDEIYAFF   180
GILVMTAVRK DNHMSTDDLF DRSLSMVYVS VMSRDRFDPL IRCLRMDDKS IRPTLRENDV   240
FTPVRKIWDL FIHQCIQNYT PGAHLTIDEQ LLGFRGRCPF RVYIPNKPSK YGIKILMMCD   300
SGTKYMINGM PYLGRGTQTN GVPLGEYYVK ELSKPVHGSC RNITCDNWFT SIPLAKNLLQ   360
EPYKLTIVGT VRSNKREIPE VLKNSRSRPV GTSMFCFDGP LTLVSYKPKP AKMVYLLSSC   420
DEDASINEST GKPQMVMYYN QTKGGVDTLD QMCSVMTCSR KTNRWPMALL YGMINIACIN   480
SFIIYSHNVS SKGEKVQSRK KFMRNLYMSL TSSFMRKRLE APTLKRYLRD NISNILPKEV   540
PGTSDDSTEE PVMKKRTYCT YCPSKIRRKA NASCKKCKKV ICREHNIDMC QSCF         594

SEQ ID NO: 117              moltype = DNA  length = 18
FEATURE                     Location/Qualifiers
misc_feature                1..18
                            note = Synthetic
source                      1..18
                            mol_type = other DNA
                            organism = synthetic construct
SEQUENCE: 117
cccttgrcat gcctggta                                                  18

SEQ ID NO: 118              moltype = DNA  length = 18
FEATURE                     Location/Qualifiers
misc_feature                1..18
                            note = Synthetic
source                      1..18
                            mol_type = other DNA
                            organism = synthetic construct
SEQUENCE: 118
taccaggcat gycaaggg                                                  18

SEQ ID NO: 119              moltype = DNA  length = 297
FEATURE                     Location/Qualifiers
misc_feature                1..297
                            note = Synthetic
source                      1..297
                            mol_type = other DNA
                            organism = synthetic construct
SEQUENCE: 119
gggtttatta gacccaccac tttgaaaaac ctatgatatt tttttaaatt gaaggctatt    60
gttgacgtgt gttatagtag cttcgcgcaa taaaccggcg gccattttga cgagcgaact   120
tcagtctcac gtgagcgtgc gtgcgagtag cacgtgtgta aagtgcgcgc gggcccgtgg   180
gaccctacca ggcatacaac gtaacattct gtcggtaaga atattttctt tattttttgg   240
catttctttg tttaatgtgt taaattataa tacgaaaaaa atattgttgc agtagaa      297

SEQ ID NO: 120              moltype = DNA  length = 337
FEATURE                     Location/Qualifiers
misc_feature                1..337
                            note = Synthetic
source                      1..337
                            mol_type = other DNA
                            organism = synthetic construct
SEQUENCE: 120
atcttttcga ttatccaaag ataatagtat tttagttgat ttattagtgc cttaaattaa    60
tgaaagtctg acttcgatct ctgcattata tgtaagattg ttaattatag aactaagagt   120
ttaatttctg ttaattaaaa ttaagcgatt ttgaataatt gttaaataaa gatatttca   180
catacattta catattttat ttattatctg taataataat acattctaaa agacataaat   240
ataaaacaaa attttcctag cttgttcatt tgtgtaaaac atgtattttc aatatcgggt   300
ttgacagacc caccaggcat gccgtgtgat ttttatg                            337

SEQ ID NO: 121              moltype = AA  length = 588
FEATURE                     Location/Qualifiers
REGION                      1..588
                            note = Synthetic
source                      1..588
                            mol_type = protein
                            organism = synthetic construct
SEQUENCE: 121
MARGLTDLEI NQILELEDVE NDVIFDESGD ESDHVSIRVE SDTEEVEIPT LEPQQGSSDS    60
ENDQPLSNLA RRSFYKGKDN TIWNRAPPNP RVRTRSENIV TGTPGVKRQA KNALLELDCF   120
HLFVNESILS VILEHTNHKI RSERQGKNTS NEYAYSETTL TELRAVIGLL YLAGLFKSGR   180
QNLQDLWASD GTGIEIFPMT MSLRRFAFIV NCLRFDDSDT REERAAIDRL APIRQIYEEF   240
VKNCKDVYTP YENLTIDEEL VAFRGRCKFR QYLPNKPAKY GIKIIALVDA YTYYSLNMEI   300
YAGDQPDGPY KVSNKPHDVV DRIVQPISQT GRNVTMDNWF TSYPTYAHLL KNHKLTAVGT   360
MKSNKTCIPP KFERREINT SLFGFQDDFT IVSYIPKRNK NVFMLSSLHH DSEIDSETGE   420
QQKPSIITFY NKTKSGVDNV DKLIRTYDVS RNSRRWPLTI FFWILNTAGI NAKIVQMLNS   480
```

```
SDNTPTRRAF IKKLGMSLIA PHQAERKTNS KIPVSLRKRI GSHLGESSAS PAKIPNVGVK    540
KRCYICPVKK DRKSKYICIS CTSHICLEHA NFVCENCRRN EEENSDSS                 588

SEQ ID NO: 122           moltype = DNA  length = 19
FEATURE                  Location/Qualifiers
misc_feature             1..19
                         note = Synthetic
source                   1..19
                         mol_type = other DNA
                         organism = synthetic construct
SEQUENCE: 122
cctttarctr ctgaggtgg                                                 19

SEQ ID NO: 123           moltype = DNA  length = 19
FEATURE                  Location/Qualifiers
misc_feature             1..19
                         note = Synthetic
source                   1..19
                         mol_type = other DNA
                         organism = synthetic construct
SEQUENCE: 123
ccacctcagy agytaaagg                                                 19

SEQ ID NO: 124           moltype = DNA  length = 273
FEATURE                  Location/Qualifiers
misc_feature             1..273
                         note = Synthetic
source                   1..273
                         mol_type = other DNA
                         organism = synthetic construct
SEQUENCE: 124
gggcttttcg agcctagcga aagtgaaatt gttcccctcc tcccttcccc cgcgcgcgac    60
aaacccgtaa cttctagtag cttcgatgtt agttgcgcct aggccgtcag aagcttcgca   120
cgtgttttcg tgcgcaattc ggtaagtaaa ttcaatttga aatttgtcgc gggcttctta   180
ggccccacct cagtgtttac gtaacttttt tgtaaatagt ttcgattaag ttattgtgtt   240
tttttttgc agtagcttga aaacgtttga aaa                                 273

SEQ ID NO: 125           moltype = DNA  length = 370
FEATURE                  Location/Qualifiers
misc_feature             1..370
                         note = Synthetic
source                   1..370
                         mol_type = other DNA
                         organism = synthetic construct
SEQUENCE: 125
ttttggtgct tgtatttttt ttcttcccat aatacaaaga taattatgaa tgtgcctaat    60
gctaaaaaga ctgttaaaaa ttaatatttt atgtaagttt gttgattatt tctaatattt   120
taatgaatac tttgtgattt tgatctcat gtgattttgc caaaaatttt gctaagtgtt    180
ttttaaaaac actcaaaagt taattataaa taaaaaaatt aaacaaaaaa catttttattt  240
tatttaaaat ctatccacaa aagcttatta ttatacaata aaacctaaaa accccaaata   300
ttttaaaata tgaacattta tatacacggg ccgcggaggc ccccacgtca gtacttacgt   360
gaaaataatt                                                          370

SEQ ID NO: 126           moltype = AA  length = 613
FEATURE                  Location/Qualifiers
REGION                   1..613
                         note = Synthetic
source                   1..613
                         mol_type = protein
                         organism = synthetic construct
SEQUENCE: 126
MEPSTSSGRK RSIGNVHNQR AAKNRRAVVP GTRDFGTTLT SWLDNEDSSG SEVEDIGDNF    60
TPERHEIESD TISQSESEEQ VADHVTEEHN MSSDDDAPLS TRRSFYGKNR YKWACQPLSR   120
AVRVPQHNII QRTNVSNLTE DDPKDPFSIW NKLMDDEILQ ETLKWTNEKI IQYRSKFSDK   180
DRPELRNLDM VELHAFIGLL LFTAVFKSNH ENVNYLFATD GTGREIFRCV MSKNRFLVIL   240
HCLRFDNPDD REERRESDKI AAISYIFTKF VGNCQKIYNV CEYATVDEML VPFRGRTHLM   300
IYMPMKPAKY GLKLMCLCDA NNGYFYNCYI YTGRGSDGAG LTEEEKKFMV PTQSVIHLAK   360
PLFGSNRNIT CDNWFTSIEL IEYLKKKGLT CVGTMKKNKR EIPKEFLPSK QRDVGSSLYG   420
YAGQNTILSH VPKKNKAVIL LSSMHHAEAV DETTGKPEII GFYNKTKGGV DEIDKKCAIY   480
TSSRRTRRWP MVVFYRMLDI STVNSHLIYD IHHDKTTERG MFLKQLARTL VLPQMKRRAL   540
NERLPRELRL SLARVLGPDM PVPDPQEVDE TFKTRRRCHT CPLKLQRKST HTCYTCKKHV   600
CLQCAKQVCA DCV                                                      613

SEQ ID NO: 127           moltype = DNA  length = 15
FEATURE                  Location/Qualifiers
misc_feature             1..15
                         note = Synthetic
source                   1..15
                         mol_type = other DNA
```

```
                        organism = synthetic construct
SEQUENCE: 127
ccctcrtatt atgtt                                                        15

SEQ ID NO: 128          moltype = DNA   length = 15
FEATURE                 Location/Qualifiers
misc_feature            1..15
                        note = Synthetic
source                  1..15
                        mol_type = other DNA
                        organism = synthetic construct
SEQUENCE: 128
aacataatay gaggg                                                        15

SEQ ID NO: 129          moltype = DNA   length = 401
FEATURE                 Location/Qualifiers
misc_feature            1..401
                        note = Synthetic
source                  1..401
                        mol_type = other DNA
                        organism = synthetic construct
SEQUENCE: 129
aagggtcaat ttgacccatt tcagtttttg gtttgaccaa agaactggtt atcctttctt        60
tttcttcacg aaagttggtg acttttcctc atctagggtc atgaacttgt gtgtaaaatc       120
tggatactgt gaagtgtcgt ggaatgtctg tgaacagttt gtatacaaag atgatgttgc       180
gggtcatttt gacccacaca cttttgatgt gagcaagtgt tgtccagatc cgaaataaac       240
atgtctcttt tgatgcacttt attttgattg ctaaattatt tatattttga ctgtctctga      300
atagaccttc agatcagaga cccaggtgtg tgtgggggag gagctttctc tcccttgtcc       360
ttgtcactgt tctcgtgtca tctctttgag aaacagcaaa a                           401

SEQ ID NO: 130          moltype = DNA   length = 247
FEATURE                 Location/Qualifiers
misc_feature            1..247
                        note = Synthetic
source                  1..247
                        mol_type = other DNA
                        organism = synthetic construct
SEQUENCE: 130
agatactgaa tattgaaaat ctcagaaaat gtgacaagtt aaattacaaa aaaaaagtgt        60
ttgtgaagga aaaaaatatt aaatatagtg ttggaataaa aaaatagtat tgtttgtctc       120
tttcctaaat gttgaaatat tctaaaataa agttgatatc agtttaacct gttttttttat      180
tgttttgagt ggatttacac agtatgggtc aaaatgaccc gcaacataat caaggtaatt       240
tttttc                                                                  247

SEQ ID NO: 131          moltype = AA    length = 579
FEATURE                 Location/Qualifiers
REGION                  1..579
                        note = Synthetic
source                  1..579
                        mol_type = protein
                        organism = synthetic construct
SEQUENCE: 131
MSSRRFTAEE ALLLFFDSDA EEEISEIEDL SDAEDNDIDD PDFQFSDDEE DSEDESAVVS        60
PSDENLGMEQ SSSTEGTWAS KDGNIKWSTS PHQSRGRLSS SNIIKMTPGP TRFAVTRVDD       120
IQSAFQLFIS QPIERIILDM TNLEGRRVFQ EKWKSLDQTD LNAYIGILIL AGVYRSKGEA       180
TSSLWNEENG RPIFRATMSL ETFHMISRVI RFDNRDTRVG RRESDKLAAI RDVWDKWVEI       240
LPLLYNPGPH VTVDERLVPF RGRCPFRQYM PNKPAKYGIK IWAACDAKSS YAWKMQVYTG       300
KSPGGAPEKN QGMRVVLEMS EGLQGHNITC DNFFTSYRLG EELQKRKLTM LGTVRRNKPE       360
LPSEILKIQG RPMHSSIFAF TEKATVVSYC PKRNKNVLVM STMHTDASLS TRDDMKPQMI       420
LDYNSTKGGV DNLDKVTATY SCQRKTARWP MAIFFNIVDV SAYNAYVLWS EINQEWNAGK       480
LYRRRLFLEE LGKALITPKI QRRARPARSP AAAAVIEKIK FRTSNQFAMD PVDTDVKKRK       540
RCQVCPSRDD SKTSTSCVKC KNFICRKHTV TFCPSCGEH                              579

SEQ ID NO: 132          moltype = DNA   length = 16
FEATURE                 Location/Qualifiers
misc_feature            1..16
                        note = Synthetic
source                  1..16
                        mol_type = other DNA
                        organism = synthetic construct
SEQUENCE: 132
ccctagaagc ccaatc                                                       16

SEQ ID NO: 133          moltype = DNA   length = 16
FEATURE                 Location/Qualifiers
misc_feature            1..16
                        note = Synthetic
source                  1..16
                        mol_type = other DNA
```

```
                          organism = synthetic construct
SEQUENCE: 133
gattgggctt ctaggg                                                       16

SEQ ID NO: 134           moltype = DNA   length = 303
FEATURE                  Location/Qualifiers
misc_feature             1..303
                         note = Synthetic
source                   1..303
                         mol_type = other DNA
                         organism = synthetic construct
SEQUENCE: 134
tacgtaaatt tgacgtatac cgcggcgaaa tatatctgtc tctttcacgt ttaccgtcgg        60
attcccgcta acttcggaac caactcagta gccattgaga actcccagga cacagttcgg      120
tcatctcggt aagtgccgcc attttgttgt aatagacagg ttgcacgtca ttttgacgta      180
taattgggct ttgtgtaact tttgaaatta tttataattt ttattgatgt gatttatttg      240
agttaatcgt attgtttcgt tacattttc atatgatatt aatattttca gattgaatat       300
aaa                                                                    303

SEQ ID NO: 135           moltype = DNA   length = 347
FEATURE                  Location/Qualifiers
misc_feature             1..347
                         note = Synthetic
source                   1..347
                         mol_type = other DNA
                         organism = synthetic construct
SEQUENCE: 135
agactgtttt ttttaaaagg cttataaagt attactattg cgtgatttaa ttttataaaa       60
atatttaaaa ccagttgatt tttttaataa ttacctaatt ttaagaaaaa atgttagaag     120
cttgatattt ttgttgattt ttttctaaga tttgattaaa aggccataat tgtattaata     180
aagagtattt ttaacttcaa atttatttta tttattaatt aaaacttcaa ttatgataat     240
acatgcaaaa atatagttca tcaacagaaa aatataggaa aactctaata gttttatttt     300
tacacgtcat ttttacgtat gattgggctt tatagctagt caaatat                    347

SEQ ID NO: 136           moltype = AA   length = 598
FEATURE                  Location/Qualifiers
REGION                   1..598
                         note = Synthetic
source                   1..598
                         mol_type = protein
                         organism = synthetic construct
SEQUENCE: 136
MESRQRLNQD EIATILENDD DYSPLDSDSE AEDRVVEDDV WSDNEDAMID YVEDTSRQED        60
PDNNIASQES ANLEVTSLTS HRIISLPQRS ICGKNNHVWS TTKGRTTGRT SAINIIRTNR      120
GPTRMCRNIV DPLLCFQLFI TDEIIHEIVK WTNVEMIVKR QNLIDISASY RDTNTMEMWA      180
LVGILTLTAV MKDNHLSTDE LFDATFSGTR YVSVMSRERF EFLIRCMRMD DKTLRPTLRS      240
DDAFIPVRKL WEIFINQCRL NYVPGGNLTV DEQLLGFRGR CPFRMYIPNK PDKYGIRFPM      300
MCDAATKYMI DAIPYLGKST KTNGLPLGEF YVKELTKTVH GTNRNVTCDN WFTSIPLAKN      360
MLQAPYNLTI VGTIRSNKRE IPEEIKNSRS RPVGSSMFCF DGPLTLVSYK PKPSRMVFLL      420
SSCDENAVIN ESNGKPDMIL FYNQTKGGVD SFDQMCKSMS ANRKTNRWPM AVFYGMLNMA      480
FVNSYIIYCH NKINKQKKPI NRKEFMKNLS TDLTTPWMQE RLKAPTLKRT LRDNITNVLK      540
NVVPPSPANN SEEPGPKKRS YCGFCSYKKR RMTKTQFYKC KKAICGEHNI DVCQDCVG        598

SEQ ID NO: 137           moltype = DNA   length = 16
FEATURE                  Location/Qualifiers
misc_feature             1..16
                         note = Synthetic
source                   1..16
                         mol_type = other DNA
                         organism = synthetic construct
SEQUENCE: 137
ccctagaagc ccaatc                                                       16

SEQ ID NO: 138           moltype = DNA   length = 16
FEATURE                  Location/Qualifiers
misc_feature             1..16
                         note = Synthetic
source                   1..16
                         mol_type = other DNA
                         organism = synthetic construct
SEQUENCE: 138
gattgggctt ctaggg                                                       16

SEQ ID NO: 139           moltype = DNA   length = 304
FEATURE                  Location/Qualifiers
misc_feature             1..304
                         note = Synthetic
source                   1..304
                         mol_type = other DNA
```

```
                        organism = synthetic construct
SEQUENCE: 139
tacgtaaatt tgacgtatac cgcggcgaaa tatctctgtt actttcacgt ttaacgtcgg    60
atcgccgcta acttctgaac caactcagta gccattggga cctcgcagga cacagttgca   120
tcatctcggt aagtgccgcc attttgttgt aatagagagg ttgcacgtca ttttgacgta   180
taattgggct ttgtgtaact tttgaaattg tttaaatttt tttaaatttg tgatttattt   240
gagttaatcg tattgtttcg ttacatttta catgtaatat taatattttc aggttgaata   300
caaa                                                                304

SEQ ID NO: 140          moltype = DNA   length = 370
FEATURE                 Location/Qualifiers
misc_feature            1..370
                        note = Synthetic
source                  1..370
                        mol_type = other DNA
                        organism = synthetic construct
SEQUENCE: 140
tgtttgtcaa gactgtatat aaagactgtt ttttctaaag aaacttataa aatattatta    60
caagttgatt taattttatg aaaaaattta aaactagttg atttttttta taattacata   120
attttaagaa aaagtgttag aggcttgatt ttttgttt tttttttcta aggtttgatt    180
gaaatgccat aatagtatta ataaagagta tttttaact aaaatctat tttatttatt    240
aattaaaact tcaattatga taactcatgc aaaaatatag ttcattaaca gaaaaatctt   300
ggaaaactct gaagttttat ttttacacgt cattttacg tatgattggg ctttataact   360
agttaaaatat                                                         370

SEQ ID NO: 141          moltype = AA   length = 598
FEATURE                 Location/Qualifiers
REGION                  1..598
                        note = Synthetic
source                  1..598
                        mol_type = protein
                        organism = synthetic construct
SEQUENCE: 141
MASRQRLNHD EIATILENDD DYSPLDSESE KEDCVVEDDV WSDNEDAIVD FVEDTSAQED    60
PDNNIASRES PNLEVTSLTS HRIITLPQRS IRGKNNHVWS TTKGRTTGRT SAINIIRTNR   120
GPTRMCRNIV DPLLCFQLFI TDEIIHEIVK WTNVEIIVKR QNLKDISASY RDTNTMEIWA   180
LVGILTLTAV MKDNHLSTDE LFDATFSGTR YVSVMSRERF EFLIRCIRMD DKTLRPTLRS   240
DDAFLPVRKI WEIFINQCRQ NHVPGSNLTV DEQLLGFRGR CPFRMYIPNK PDKYGIKFPM   300
MCAAATKYMI DAIPYLGKST KTNGLPLGEF YVKDLTKTVH GTNRNITCDN WFTSIPLAKN   360
MLQAPYNLTI VGTIRSNKRE MPEEIKNSRS RPVGSSMFCF DGPLTLVSYK PKPSKMVFLL   420
SSCDENAVIN ESNGKPDMIL FYNQTKGGVD SFDQMCKSMS ANRKTNRWPM AVFYGMLNMA   480
FVNSYIIYCH NKINKQEKPI SRKEFMKKLS IQLTTPWMQE RLQAPTLKRT LRDNITNVLK   540
NVVPASSENI SNEPEPKKRR YCGVCSYKKR RMTKAQCCKC KKAICGEHNI DVCQDCIG    598

SEQ ID NO: 142          moltype = DNA   length = 32
FEATURE                 Location/Qualifiers
misc_feature            1..32
                        note = Synthetic
source                  1..32
                        mol_type = other DNA
                        organism = synthetic construct
SEQUENCE: 142
cagttgaagt cggaagttta catacactta ag                                  32

SEQ ID NO: 143          moltype = DNA   length = 32
FEATURE                 Location/Qualifiers
misc_feature            1..32
                        note = Synthetic
source                  1..32
                        mol_type = other DNA
                        organism = synthetic construct
SEQUENCE: 143
ctaaggtgta tgtaaacttc cgacttcaac tg                                  32

SEQ ID NO: 144          moltype = DNA   length = 227
FEATURE                 Location/Qualifiers
misc_feature            1..227
                        note = Synthetic
source                  1..227
                        mol_type = other DNA
                        organism = synthetic construct
SEQUENCE: 144
cagttgaagt cggaagttta catacactta agttggagtc attaaaactc gttttcaac    60
tacaccacaa atttcttgtt aacaaacaat agttttggca agtcagttag gacatctact   120
ttgtgcatga cacaagtcat ttttccaaca attgtttaca gacagattat ttcacttata   180
attcactgta tcacaattcc agtgggtcag aagtttacat acactaa                 227

SEQ ID NO: 145          moltype = DNA   length = 229
FEATURE                 Location/Qualifiers
```

```
misc_feature            1..229
                        note = Synthetic
source                  1..229
                        mol_type = other DNA
                        organism = synthetic construct
SEQUENCE: 145
ttgagtgtat gttaacttct gacccactgg gaatgtgatg aaagaaataa aagctgaaat   60
gaatcattct ctctactatt attctgatat ttcacattct taaaataaag tggtgatcct  120
aactgacctt aagacaggga atctttactc ggattaaatg tcaggaattg tgaaaaagtg  180
agtttaaatg tatttggcta aggtgtatgt aaacttccga cttcaactg              229

SEQ ID NO: 146          moltype = AA  length = 340
FEATURE                 Location/Qualifiers
REGION                  1..340
                        note = Synthetic
source                  1..340
                        mol_type = protein
                        organism = synthetic construct
SEQUENCE: 146
MGKSKEISQD LRKRIVDLHK SGSSLGAISK RLAVPRSSVQ TIVRKYKHHG TTQPSYRSGR   60
RRVLSPRDER TLVRKVQINP RTTAKDLVKM LEETGTKVSI STVKRVLYRH NLKGHSARKK  120
PLLQNRHKKA RLRFATAHGD KDRTFWRNVL WSDETKIELF GHNDHRYVWR KKGEACKPKN  180
TIPTVKHGGG SIMLWGCFAA GGTGALHKID GIMDKENYVD ILKQHLKTSV RKLKLGRKWV  240
FQHDNDPKHT SKVVAKWLKD NKVKVLEWPS QSPDLNPIEN LWAELKKRVR ARRPTNLTQL  300
HQLCQEEWAK IHPNYCGKLV EGYPKRLTQV KQFKGNATKY                       340

SEQ ID NO: 147          moltype = DNA  length = 16
FEATURE                 Location/Qualifiers
misc_feature            1..16
                        note = Synthetic
source                  1..16
                        mol_type = other DNA
                        organism = synthetic construct
SEQUENCE: 147
cagtgttctt caacct                                                   16

SEQ ID NO: 148          moltype = DNA  length = 16
FEATURE                 Location/Qualifiers
misc_feature            1..16
                        note = Synthetic
source                  1..16
                        mol_type = other DNA
                        organism = synthetic construct
SEQUENCE: 148
aggttgaaga acactg                                                   16

SEQ ID NO: 149          moltype = DNA  length = 328
FEATURE                 Location/Qualifiers
misc_feature            1..328
                        note = Synthetic
source                  1..328
                        mol_type = other DNA
                        organism = synthetic construct
SEQUENCE: 149
cagtgttctt caacctgtgt tccgcggaac cctagggttc cacccaaagg ctttcggggt   60
tccgcgagtc attgcttcaa ttcgagagac gtcggccgcg ccgctcttca gaatgcacat  120
gcgtcaatcg gagtttcatg ttgaaacatg ttatccattc gcatagttga cttacactgc  180
acttaacctt aattttcaaa aatatgtaac tgtacttgtg gtcgtagttt tgttgttgtt  240
ttaggtttag acaagcaaag gtaagttaac ttacagtttt aaaataaatt gtattttgtt  300
tgatcctaac ctagaatcgt tcagaaat                                     328

SEQ ID NO: 150          moltype = DNA  length = 145
FEATURE                 Location/Qualifiers
misc_feature            1..145
                        note = Synthetic
source                  1..145
                        mol_type = other DNA
                        organism = synthetic construct
SEQUENCE: 150
ccaaagcacg ggctcacctt gttcgtaaca agtcaacgca gctgtcccta aaatctcatc   60
tgggtgtatt actaaatgaa gggttccata aaaaaaaata tctcgacaaa gggttccgcc  120
ggatggcaaa ggttgaagaa cactg                                        145

SEQ ID NO: 151          moltype = AA  length = 636
FEATURE                 Location/Qualifiers
REGION                  1..636
                        note = Synthetic
source                  1..636
                        mol_type = protein
```

```
                        organism = synthetic construct
SEQUENCE: 151
MMLNWLKSGK LESQSQEQSS CYLENSNCLP PTLDSTDIIG EENKAGTTSR KKRKYDEDYL    60
NFGFTWTGDK DEPNGLCVIC EQVVNNSSLN PAKLKRHLDT KHPTLKGKSE YFKRKCNELN   120
QKKHTFERYV RDDNKNLLKA SYLVSLRIAK QGEAYTIAEK LIKPCTKDLT TCVFGEKFAS   180
KVDLVPLSDT TISRRIEDMS YFCEAVLVNR LKNAKCGFTL QMDESTDVAG LAILLVFVRY   240
IHESSFEEDM LFCKALPTQT TGEEIFNLLN AYFEKHSIPW NLCYHICTDG AKAMVGVIKG   300
VIARIKKLVP DIKASHCCLH RHALAVKRIP NALHEVLNDA VKMINFIKSR PLNARVFALL   360
CDDLGSLHKN LLLHTEVRWL SRGKVLTRFW ELRDEIRIFF NEREFAGKLN DTSWLQNLAY   420
IADIFSYLNE VNLSLQGPNS TIFKVNSRIN SIKSKLKLWE ECITKNNTEC FANLNDFLET   480
SNTALDPNLK SNILEHLNGL KNTFLEYFPP TCNNISWVEN PFNECGNVDT LPIKEREQLI   540
DIRTDTTLKS SFVPDGIGPF WIKLMDEFPE ISKRAVKELM PFVTTYLCEK SFSVYVATKT   600
KYRNRLDAED DMRLQLTTIH PDIDNLCNNK QAQKSH                            636

SEQ ID NO: 152          moltype = DNA   length = 211
FEATURE                 Location/Qualifiers
misc_feature            1..211
                        note = Synthetic
source                  1..211
                        mol_type = other DNA
                        organism = synthetic construct
SEQUENCE: 152
tccctatcag tgatagagag tctagtctgc ataccttccc tatcagtgat agagagacaa    60
ctccttatag gttccctatc agtgatagag agtaaactgg tcataccttc cctatcagtg   120
atagagagta aactgtagat accttcccta tcagtgatag agagtaaact ggatataggt   180
tccctatcag tgatagagaa agcttatacc t                                  211

SEQ ID NO: 153          moltype = DNA   length = 103
FEATURE                 Location/Qualifiers
misc_feature            1..103
                        note = Synthetic
source                  1..103
                        mol_type = other DNA
                        organism = synthetic construct
SEQUENCE: 153
tccctatcag tgatagagag taaactgtag ataccttccc tatcagtgat agagagtaaa    60
ctggatatag gttccctatc agtgatagag aaagcttata cct                    103

SEQ ID NO: 154          moltype = AA    length = 467
FEATURE                 Location/Qualifiers
REGION                  1..467
                        note = Synthetic
source                  1..467
                        mol_type = protein
                        organism = synthetic construct
SEQUENCE: 154
MGVKVLFALI CIAVAEAEVQ LVESGGGLVQ PGGSLRLSCA ASGFNIKDTY IHWVRQAPGK    60
GLEWVARIYP TNGYTRYADS VKGRFTISAD TSKNTAYLQM NSLRAEDTAV YYCSRWGGDG   120
FYAMDYWGQG TLVTVSSAST KGPSVFPLAP SSKSTSGGTA ALGCLVKDYF PEPVTVSWNS   180
GALTSGVHTF PAVLQSSGLY SLSSVVTVPS SSLGTQTYIC NVNHKPSNTK VDKKVEPKSC   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPGK                467

SEQ ID NO: 155          moltype = AA    length = 236
FEATURE                 Location/Qualifiers
REGION                  1..236
                        note = Synthetic
source                  1..236
                        mol_type = protein
                        organism = synthetic construct
SEQUENCE: 155
MDMRVPAQLL GLLLLWLPGA KCDIQMTQSP SSLSASVGDR VTITCRASQD VNTAVAWYQQ    60
KPGKAPKLLI YSASFLYSGV PSRFSGSRSG TDFTLTISSL QPEDFATYYC QQHYTTPPTF   120
GQGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236

SEQ ID NO: 156          moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 156
agaaacaaac caacctgtct gtatta                                        26

SEQ ID NO: 157          moltype = DNA   length = 28
```

```
FEATURE                 Location/Qualifiers
misc_feature            1..28
                        note = Synthetic
source                  1..28
                        mol_type = other DNA
                        organism = synthetic construct
SEQUENCE: 157
aacaaacaga caatctggtc tgtttgta                                          28

SEQ ID NO: 158          moltype = DNA  length = 43
FEATURE                 Location/Qualifiers
misc_feature            1..43
                        note = Synthetic
source                  1..43
                        mol_type = other DNA
                        organism = synthetic construct
SEQUENCE: 158
ttgaaaacaa acagacaatc tggtctgttt gtattataag taa                         43

SEQ ID NO: 159          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 159
aaagaaacaa accaacctgt ctgtattatc                                        30

SEQ ID NO: 160          moltype = DNA  length = 28
FEATURE                 Location/Qualifiers
misc_feature            1..28
                        note = Synthetic
source                  1..28
                        mol_type = other DNA
                        organism = synthetic construct
SEQUENCE: 160
aagaaacaaa ccaacctgtc tgtattat                                          28

SEQ ID NO: 161          moltype = DNA  length = 301
FEATURE                 Location/Qualifiers
misc_feature            1..301
                        note = Synthetic
source                  1..301
                        mol_type = other DNA
                        organism = synthetic construct
SEQUENCE: 161
agtcattggg ttttccagc caatttataa aacgccatgt actttcccac cattgacgtc        60
aatgggctat tgaaactaat gcaacgtgac ctttaaacgg tactttccca tagctgatta       120
atgggaaagt accgttctcg agccaataca cgtcaatggg agtttgtttt ggcaccaaaa       180
tcaacgggac tttccaaaat gtcgtaataa ccccgccccg ttgacgcaaa tgggcggtag       240
gcgtgtacgg tgggaggtct atataagcag agctcagaaa caaaccaacc tgtctgtatt       300
a                                                                       301

SEQ ID NO: 162          moltype = DNA  length = 303
FEATURE                 Location/Qualifiers
misc_feature            1..303
                        note = Synthetic
source                  1..303
                        mol_type = other DNA
                        organism = synthetic construct
SEQUENCE: 162
agtcattggg ttttccagc caatttataa aacgccatgt actttcccac cattgacgtc        60
aatgggctat tgaaactaat gcaacgtgac ctttaaacgg tactttccca tagctgatta       120
atgggaaagt accgttctcg agccaataca cgtcaatggg agtttgtttt ggcaccaaaa       180
tcaacgggac tttccaaaat gtcgtaataa ccccgccccg ttgacgcaaa tgggcggtag       240
gcgtgtacgg tgggaggtct atataagcag agctcaacaa acagacaatc tggtctgttt       300
gta                                                                     303

SEQ ID NO: 163          moltype = DNA  length = 303
FEATURE                 Location/Qualifiers
misc_feature            1..303
                        note = Synthetic
source                  1..303
                        mol_type = other DNA
                        organism = synthetic construct
SEQUENCE: 163
agtcattggg ttttccagc caatttataa aacgccatgt actttcccac cattgacgtc        60
aatgggctat tgaaactaat gcaacgtgac ctttaaacgg tactttccca tagctgatta       120
```

```
atgggaaagt accgttctcg agccaataca cgtcaatggg agtttgtttt ggcaccaaaa    180
tcaacgggac tttccaaaat gtcgtaataa ccccgccccg ttgacgcaaa tgggcggtag    240
gcgtgtacgg tgggaggtct atataagcag agctcaacaa acagacaatc tggtctgttt    300
gta                                                                  303

SEQ ID NO: 164           moltype = DNA   length = 231
FEATURE                  Location/Qualifiers
misc_feature             1..231
                         note = Synthetic
source                   1..231
                         mol_type = other DNA
                         organism = synthetic construct
SEQUENCE: 164
aaagaaacaa accaacctgt ctgtattatc aaagaaacaa accaacctgt ctgtattatc     60
aaagaaacaa accaacctgt ctgtattatc aaagaaacaa accaacctgt ctgtattatc    120
aaagaaacaa accaacctgt ctgtattatc aaagaaacaa accaacctgt ctgtattatc    180
taggcgtgcc ctatgggcgg tctatataag cagagcccgt ttagtgaacc g             231

SEQ ID NO: 165           moltype = DNA   length = 231
FEATURE                  Location/Qualifiers
misc_feature             1..231
                         note = Synthetic
source                   1..231
                         mol_type = other DNA
                         organism = synthetic construct
SEQUENCE: 165
aaacaaacag acaatctggt ctgtttgtat aaacaaacag acaatctggt ctgtttgtat     60
aaacaaacag acaatctggt ctgtttgtat aaacaaacag acaatctggt ctgtttgtat    120
aaacaaacag acaatctggt ctgtttgtat aaacaaacag acaatctggt ctgtttgtat    180
taggcgtgcc ctatgggcgg tctatataag cagagcccgt ttagtgaacc g             231

SEQ ID NO: 166           moltype = DNA   length = 309
FEATURE                  Location/Qualifiers
misc_feature             1..309
                         note = Synthetic
source                   1..309
                         mol_type = other DNA
                         organism = synthetic construct
SEQUENCE: 166
ttgaaaacaa acagacaatc tggtctgttt gtattataag taattgaaaa caaacagaca     60
atctggtctg tttgtattat aagtaattga aaacaaacag acaatctggt ctgtttgtat    120
tataagtaat tgaaaacaaa cagacaatct ggtctgtttg tattataagt aattgaaaac    180
aaacagacaa tctggtctgt ttgtattata agtaattgaa aacaaacaga caatctggtc    240
tgtttgtatt ataagtaata ggcgtgccct atgggcggtc tatataagca gagcccgttt    300
agtgaaccg                                                            309

SEQ ID NO: 167           moltype = DNA   length = 331
FEATURE                  Location/Qualifiers
misc_feature             1..331
                         note = Synthetic
source                   1..331
                         mol_type = other DNA
                         organism = synthetic construct
SEQUENCE: 167
aaagaaacaa accaacctgt ctgtattatc aaagaaacaa accaacctgt ctgtattatc     60
aaagaaacaa accaacctgt ctgtattatc aaagaaacaa accaacctgt ctgtattatc    120
aaagaaacaa accaacctgt ctgtattatc aaagaaacaa accaacctgt ctgtattatc    180
taggcgtgcc ctatgggcgg tctatataag cagagcccgt ttagtgaacc gtcagatcgc    240
ctggagaggc catccaacgt ctctggggtg agacagcttg cttgttcttt ttgcagaagc    300
tcagaataaa cgctcaactt tggccgccac c                                   331

SEQ ID NO: 168           moltype = DNA   length = 331
FEATURE                  Location/Qualifiers
misc_feature             1..331
                         note = Synthetic
source                   1..331
                         mol_type = other DNA
                         organism = synthetic construct
SEQUENCE: 168
aaacaaacag acaatctggt ctgtttgtat aaacaaacag acaatctggt ctgtttgtat     60
aaacaaacag acaatctggt ctgtttgtat aaacaaacag acaatctggt ctgtttgtat    120
aaacaaacag acaatctggt ctgtttgtat aaacaaacag acaatctggt ctgtttgtat    180
taggcgtgcc ctatgggcgg tctatataag cagagcccgt ttagtgaacc gtcagatcgc    240
ctggagaggc catccaacgt ctctggggtg agacagcttg cttgttcttt ttgcagaagc    300
tcagaataaa cgctcaactt tggccgccac c                                   331

SEQ ID NO: 169           moltype = DNA   length = 409
FEATURE                  Location/Qualifiers
misc_feature             1..409
```

```
                        note = Synthetic
source                  1..409
                        mol_type = other DNA
                        organism = synthetic construct
SEQUENCE: 169
ttgaaaacaa acagacaatc tggtctgttt gtattataag taattgaaaa caaacagaca    60
atctggtctg tttgtattat aagtaattga aaacaaacag acaatctggt ctgtttgtat   120
tataagtaat tgaaaacaaa cagacaatct ggtctgtttg tattataagt aattgaaaac   180
aaacagacaa tctggtctgt ttgtattata agtaattgaa aacaaacaga caatctggtc   240
tgtttgtatt ataagtaata ggcgtgccct atgggcggtc tatataagca gagcccgttt   300
agtgaaccgt cagatcgcct ggagaggcca tccaacgtct ctggggtgag acagcttgct   360
tgttcttttt gcagaagctc agaataaacg ctcaactttg ccgccacc                409

SEQ ID NO: 170          moltype = AA   length = 206
FEATURE                 Location/Qualifiers
REGION                  1..206
                        note = Synthetic
source                  1..206
                        mol_type = protein
                        organism = synthetic construct
SEQUENCE: 170
MVIMSPKRRT QAERAMETQG KLIAAALGVL REKGYAGFRI ADVPGAAGVS RGAQSHHFPT    60
KLELLLATFE WLYEQITERS RARLAKLKPE DDVIQQMLDD AAEFFLDDDF SISLDLIVAA   120
DRDPALREGI QRTVERNRFV VEDMWLGVLV SRGLSRDDAE DILWLIFNSV RGLAVRSLWQ   180
KDKERFERVR NSTLEIARER YAKFKR                                        206

SEQ ID NO: 171          moltype = AA   length = 206
FEATURE                 Location/Qualifiers
REGION                  1..206
                        note = Synthetic
source                  1..206
                        mol_type = protein
                        organism = synthetic construct
SEQUENCE: 171
MVIMSPKRRT QAERAMETQG KLIAAALGVL REKGYAGFRI ADVPGAAGVS RGAQSHHFPT    60
KLELLLATFE WLYEQITERS RARLAKLKPE DDVIQQMLDD AAEFFLDDDF SISLDLIVAA   120
DRDPVLREGI QRTVERNRFV VGDIWLGVLV SRGLSRDDAE DILWLIFNSV RGLAVRSLWQ   180
KDKERFERVR NSTLEIARER YAKFKR                                        206

SEQ ID NO: 172          moltype = AA   length = 272
FEATURE                 Location/Qualifiers
REGION                  1..272
                        note = Synthetic
source                  1..272
                        mol_type = protein
                        organism = synthetic construct
SEQUENCE: 172
MVIMSPKRRT QAERAMETQG KLIAAALGVL REKGYAGFRI ADVPGAAGVS RGAQSHHFPT    60
KLELLLATFE WLYEQITERS RARLAKLKPE DDVIQQMLDD AAEFFLDDDF SISLDLIVAA   120
DRDPVLREGI QRTVERNRFV VGDIWLGVLV SRGLSRDDAE DILWLIFNSV RGLAVRSLWQ   180
KDKERFERVR NSTLEIARER YAKFKRAYSR ARTKNNYGST IEGLLDLPDD DPTDALDDFD   240
LDMLPADALD DFDLDMLPAD ALDDFDLDML PG                                 272

SEQ ID NO: 173          moltype = DNA   length = 12
FEATURE                 Location/Qualifiers
source                  1..12
                        mol_type = other DNA
                        organism = synthetic construct
SEQUENCE: 173
acgtcaatgg ga                                                        12

SEQ ID NO: 174          moltype = DNA   length = 19
FEATURE                 Location/Qualifiers
source                  1..19
                        mol_type = other DNA
                        organism = synthetic construct
SEQUENCE: 174
tcgctatcag tgatagaga                                                 19

SEQ ID NO: 175          moltype = DNA   length = 19
FEATURE                 Location/Qualifiers
source                  1..19
                        mol_type = other DNA
                        organism = synthetic construct
SEQUENCE: 175
actctatcat tgatagagt                                                 19

SEQ ID NO: 176          moltype = DNA   length = 13
FEATURE                 Location/Qualifiers
```

```
source              1..13
                    mol_type = other DNA
                    organism = synthetic construct
SEQUENCE: 176
gtttagtgaa ccg                                                          13
```